US012668575B2

(12) United States Patent
Zhan et al.

(10) Patent No.: US 12,668,575 B2
(45) Date of Patent: Jun. 30, 2026

(54) N-(BENZOYL)-PHENYLALANINE COMPOUND, PHARMACEUTICAL COMPOSITION CONTAINING SAME, AND USE THEREOF

(71) Applicants: Hangzhou Apeloa Medicine Research Institute Co., Ltd., Zhejiang (CN); Apeloa Pharmaceutical Co., Ltd., Zhejiang (CN)

(72) Inventors: Weiqiang Zhan, Zhejiang (CN); Zhanguo Wang, Zhejiang (CN); Fanglei Chen, Zhejiang (CN); Fengming Yang, Zhejiang (CN); Jianbo Wu, Zhejiang (CN); Fangmeng Zhu, Zhejiang (CN)

(73) Assignees: HANGZHOU APELOA MEDICINE RESEARCH INSTITUTE CO., LTD., Zhejiang (CN); APELOA PHARMACEUTICAL CO., LTD., Zhejiang (CN)

( * ) Notice: Subject to any disclaimer, the term of this patent is extended or adjusted under 35 U.S.C. 154(b) by 370 days.

(21) Appl. No.: 18/273,502

(22) PCT Filed: Nov. 23, 2021

(86) PCT No.: PCT/CN2021/132456

§ 371 (c)(1),
(2) Date: Jul. 20, 2023

(87) PCT Pub. No.: WO2022/156351

PCT Pub. Date: Jul. 28, 2022

(65) Prior Publication Data

US 2024/0150287 A1 May 9, 2024

(30) Foreign Application Priority Data

Jan. 20, 2021 (CN) ......................... 202110075764.7

(51) Int. Cl.

| | |
|---|---|
| ***C07D 209/34*** | (2006.01) |
| ***C07D 235/26*** | (2006.01) |
| ***C07D 235/28*** | (2006.01) |
| ***C07D 401/04*** | (2006.01) |
| ***C07D 401/12*** | (2006.01) |
| ***C07D 405/04*** | (2006.01) |
| ***C07D 471/04*** | (2006.01) |
| ***C07D 498/18*** | (2006.01) |

(52) U.S. Cl.

CPC ......... *C07D 209/34* (2013.01); *C07D 235/26* (2013.01); *C07D 235/28* (2013.01); *C07D 401/04* (2013.01); *C07D 401/12* (2013.01); *C07D 405/04* (2013.01); *C07D 471/04* (2013.01); *C07D 498/18* (2013.01)

(58) Field of Classification Search

CPC .. C07D 209/34; C07D 235/26; C07D 235/28; C07D 401/04; C07D 401/12; C07D 405/04; C07D 471/04; C07D 498/18

See application file for complete search history.

(56) References Cited

U.S. PATENT DOCUMENTS 7,250,516 B2 7/2007 Okuzumi et al.

FOREIGN PATENT DOCUMENTS

| | | | |
|---|---|---|---|
| CN | 101300255 | A | 11/2008 |
| EP | 1881982 | B1 | 11/2013 |
| JP | 2008540686 | A | 1/2008 |
| JP | 2016037467 | * | 3/2016 |
| JP | 2016037467 | A | 3/2016 |
| WO | WO 2003/053926 | A1 | 4/2005 |
| WO | WO 2008064823 | A1 | 6/2008 |
| WO | WO 2022/156351 | A1 | 7/2022 |

OTHER PUBLICATIONS

Arrode, PLOS Pathogens, Jun. 2016, 1-27. (Year: 2016).*
Berlin, Cell, vol. 74, Jul. 1993, 185-195. (Year: 1993).*
Yu, Biomedicines, 2025, vol. 1, 2659, 1-29. (Year: 2025).*
Sircar et al., "Synthesis and SAR of N-benzoyl-L-biphenylalanine derivatives: discovery of TR-14035, a dual alpha(4)beta(7)/alpha(4)beta(1) integrin antagonist", Bioorg. Med. Chem., vol. 10, No. 6, pp. 2051-2066 (Jun. 2002).
International Search Report from International Application No. PCT/CN2021/132456, 2 pages, Mailed Feb. 24, 2022, Application now published as International Publication No. WO2022/156351 on Jul. 28, 2022.

* cited by examiner

*Primary Examiner* — D Margaret M Seaman
(74) *Attorney, Agent, or Firm* — McDermott Will & Schulte LLP; Brennen P. Baylor; Judy M. Mohr

(57) ABSTRACT

The present invention belongs to the field of pharmaceutical chemistry, and relates to an N-(benzoyl)-phenylalanine compound used as an α4β7 integrin antagonist, including the pharmaceutical composition and the use, and in particular to a compound represented by general formula (1). The compound exhibits good α4β7 integrin binding inhibitory activity, can be used as a high-efficiency α4β7 integrin antagonist, and used for preventing and/or treating α4β7 integrin-related diseases such as autoimmune diseases and inflammatory diseases.

(1)

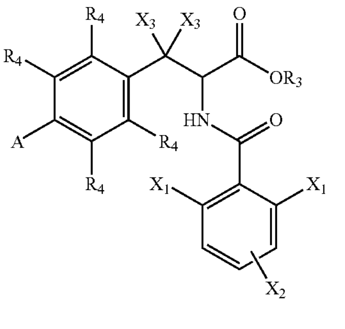

13 Claims, No Drawings

N-(BENZOYL)-PHENYLALANINE COMPOUND, PHARMACEUTICAL COMPOSITION CONTAINING SAME, AND USE THEREOF

CROSS-REFERENCE TO RELATED APPLICATIONS

This application is a U.S. National Stage Application under 35 U.S.C. § 371 which claims the benefit of priority to International Patent Application No. PCT/CN2021/132456, filed Nov. 23, 2021, which claims the benefit of priority to Chinese Patent Application No. 202110075764.7, filed Jan. 20, 2021, each of which is hereby incorporated by reference in its entirety.

TECHNICAL FIELD

The present invention relates to the field of pharmaceutical chemistry, and relates to a N-(benzoyl)-phenylalanine compound used as an α4β7 integrin antagonist, a pharmaceutical composition containing same as an active ingredient, and their uses for prevention and/or treatment of α4β7 integrin related diseases (such as autoimmune and inflammatory diseases).

TECHNOLOGY BACKGROUND

Integrin is a member of integral protein family. It is a kind of heterodimer cell surface protein that generally exists on the surface of vertebrate cells and depends on $Ca^{2+}$ or $Mg^{2+}$. It is used to mediate the mutual recognition and adhesion between cells and between cells and extracellular matrixes, and plays the role of connecting the external effects and the internal structure of cells.

Integrin is a transmembrane heterodimer composed of two non-covalently bound transmembrane subunits (i.e. α and β). The extracellular head can combine with extracellular matrix protein, and the intracellular tail can connect with actin. Both subunits of the integrin are glycosylated and bound together by a non-covalent bond.

Currently, there are a total of 18 known a subunits and 8 known β subunits. Among them, the α4β7 integrin is expressed on the surface of lymphocytes and recognizes the mucosal address in cell adhesion molecule-1 (MAdCAM-1) of the extracellular ligand, which is expressed in the high endothelial venules (HEV) of the intestinal mucosal venules and the gut-associated lymphoid tissues (GALT). α4β7 integrin control the transfer of lymphocytes to intestinal tissues and their retention in the intestine through their interaction with MAdCAM-1. Someone has proposed that inhibiting the interaction between integrin and its ligand is an effective method for treating various autoimmune and inflammatory diseases, and blocking the α4β7-MAdCAM-1 interaction has shown therapeutic effects on inflammatory bowel diseases, such as Crohn's disease (CD) and ulcerative colitis (UC).

Therefore, there is an urgent need to develop α4β7 integrin antagonists for the prevention and/or treatment of autoimmune and inflammatory diseases (especially inflammatory bowel diseases).

SUMMARY OF THE INVENTION

The purpose of the present invention is to provide a N-(benzoyl)-phenylalanine compound with a novel structure, which has high selectivity and inhibitory activity on α4β7 integrin, and can be administered orally.

In addition, the purpose of the present invention is to provide a pharmaceutical composition containing the aforementioned compound as an active ingredient for the drug.

In addition, the purpose of the present invention is to provide the intended use of aforementioned compound or pharmaceutical composition for the prevention and/or treatment of α4β7 integrin related diseases (such as autoimmune and inflammatory diseases).

Specifically, the aforementioned purposes of the present invention are achieved through the following solutions:

[1] Compounds as shown in general formula (1) or pharmaceutically acceptable salts, esters, solvates, optical isomers, tautomers, isotope markers, or prodrugs thereof.

(1)

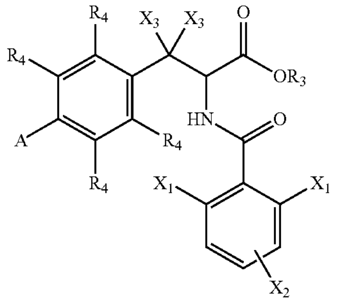

Where,

- $R_3$ is hydrogen, $C_{1-6}$ alkyl, $C_{1-6}$ haloalkyl, $C_{2-6}$ alkenyl, $C_{2-6}$ alkynyl, $C_{2-6}$ cycloalkyl, 3-7 membered heterocyclic alkyl, $C_{6-10}$ aryl, or 5-10 membered heteroaryl, which can be optionally substituted by at least one of the following substituents: halogen, $C_{1-6}$ alkyl, $C_{3-6}$ cycloalkyl, 3-7 membered heterocyclic alkyl, $C_{6-10}$ aryl, and 5-10 membered heteroaryl;
- Each $R_4$ is independently hydrogen or halogen;
- Each $X_1$ is independently hydrogen or halogen;
- $X_2$ is hydrogen, halogen, hydroxyl, amino, aldehyde, carboxyl, cyano, nitro, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$, alkylthio, $C_{1-6}$ haloalkythio, $C_{1-6}$ alkanoyl, $C_{1-6}$ alkylamino, di ($C_{1-6}$ alkyl) amino, $C_{1-6}$ alkoxycarbonyl, $C_{1-6}$ alkanoyloxy, $C_{1-6}$ alkyl amido, aminoformyl, $C_{1-6}$ alkyl aminoformyl, di ($C_{1-6}$ alkyl) carbamoyl, $C_{1-6}$ alkoxy sulfonyl, $C_{1-6}$ alkyl sulfonyloxy, $C_{1-6}$ alkyl sulfonyl amino, amino sulfonyl, $C_{1-6}$ alkyl amino sulfonyl, di ($C_{1-6}$ alkyl) amino sulfonyl, $C_{1-6}$ cycloalkyl, 3-7-membered heterocyclic alkyl, $C_{6-10}$ aryl, 5-10 membered heteroaryl, $C_{6-10}$ aryloxy, 5-10 membered heteroaryloxy, $C_{6-10}$ arylthio, 5-10 membered heteroaryl thio, $C_{6-10}$ arylamino, 5-10 membered heteroarylamino, $C_{6\sim10}$ arylcarbonyl, 5-10 membered heteroarylcarbonyl, $C_{6\sim10}$ aryloxycarbonyl, 5~10 membered heteroaryloxycarbonyl, $C_{6\sim10}$ arylformyloxy, 5~10 membered heteroarylformyloxy, $C_{6\sim10}$ arylformamido, 5~10 membered heteroarylformamido, $C_{6\sim10}$ arylaminoformyl, 5~10 membered heteroarylaminoformyl, $C_{6\sim10}$ aryloxy sulfonyl, 5~10 membered heteroaryloxy sulfonyl, $C_{6\sim10}$ arylsulfonyloxy, 5~10 membered heteroarylsulfonyloxy, $C_{6\sim10}$ arylsulfonylamino, 5~10 membered heteroarylsulfonylamino, $C_{6\sim10}$ arylaminosulfonyl or 5~10 membered heteroarylaminosulfonyl, which is optionally substituted by at least one of the following substituents: halogen, $C_{1\sim6}$ alkyl, $C_{3\sim6}$ cycloalkyl, 3~7 membered heterocyclic alkyl, $C_{6\sim10}$ aryl and 5~10 membered heteroaryl;

Each $X_3$ is independently hydrogen or halogen;

A is a group as shown in general formula (2-1), (2-2), or (2-3), (2-1)

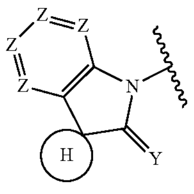

(2-2)

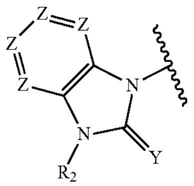

(2-3)

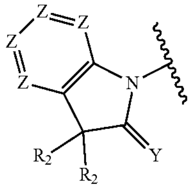

The ring H is a $C_{3-6}$ sub-cyclic alkyl or a 3-7 membered sub-heterocyclic alkyl, which can be optionally substituted by at least one of the following substituents: halogen. $C_{1-6}$ alkyl, $C_{3-6}$ cycloalkyl, 3-7 membered heterocyclic alkyl, $C_{6-10}$ aryl, and 5-10 membered heteroaryl;

Y is either O or S;

Each Z is independently $CR_1$ or N;

If it is present, each $R_1$ is independently hydrogen, halogen, hydroxyl, amino, aldehyde, carboxyl, cyano, nitro, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylthio, $C_{1-6}$ haloalkythio, $C_{1-6}$ alkanoyl, $C_{1-6}$ alkylamino, di ($C_{1-6}$ alkyl) amino. $C_{1-6}$ alkoxycarbonyl, $C_{1-6}$ alkanoyloxy, $C_{1-6}$ alkyl amido, aminoformyl, $C_{1-6}$ alkyl aminoformyl, di ($C_{1-6}$ alkyl) carbamoyl, $C_{1-6}$ alkoxy sulfonyl, $C_{1-6}$ alkyl sulfonyloxy, $C_{1-6}$ alkyl sulfonyl amino, amino sulfonyl, $C_{1-6}$ alkyl amino sulfonyl, di ($C_{1-6}$ alkyl) amino sulfonyl, $C_{3-6}$ cycloalkyl, 3-7-membered heterocyclic alkyl, $C_{6-10}$ aryl, 5-10 membered heteroaryl, $C_{6-10}$ aryloxy, 5-10 membered heteroaryloxy, $C_{6-10}$ arylthio, 5-10 membered heteroaryl thio, $C_{6-10}$ arylamino, 5-10 membered heteroarylamino, $C_{6\sim10}$ arylcarbonyl, 5-10 membered heteroarylcarbonyl, $C_{6\sim10}$ aryloxycarbonyl, 5~10 membered heteroaryloxycarbonyl, $C_{6\sim10}$ arylformyloxy, 5~10 membered heteroarylformyloxy, $C_{6\sim10}$ arylformamido, 5~10 membered heteroarylformamido, $C_{6\sim10}$ arylaminoformyl, 5~10 membered heteroarylaminoformyl, $C_{6\sim10}$ aryloxy sulfonyl, 5~10 membered heteroaryloxy sulfonyl, $C_{6\sim10}$ arylsulfonyloxy, 5~10 membered heteroarylsulfonyloxy, $C_{6\sim10}$ arylsulfonylamino, 5~10 membered heteroarylsulfonylamino, $C_{6\sim10}$ arylaminosulfonyl or 5~10 membered heteroarylaminosulfonyl, which is optionally substituted by at least one of the following substituents: halogen, $C_{1\sim6}$ alkyl, $C_{3\sim6}$ cycloalkyl, 3~7 membered heterocyclic alkyl, $C_{6\sim10}$ aryl and 5~10 membered heteroaryl;

If it is present, each $R_2$ is independently hydrogen, $C_{1-6}$ alkyl, $C_{1-6}$ haloalkyl, $C_{2-6}$ alkenyl, $C_{2-6}$ alkynyl, $C_{1-6}$ alkanoyl, $C_{1-6}$ alkoxycarbonyl, $C_{1-6}$ alkyl amido, aminoformyl, $C_{1-6}$ alkylaminoformyl, di ($C_{1-6}$ alkyl) aminoformyl, $C_{3-6}$ cycloalkyl, 3-7 membered heterocyclic alkyl, $C_{6-10}$ aryl, 5-10 membered heteroaryl, $C_{6-10}$ arylcarbonyl, 5-10 membered heteroarylcarbonyl, $C_{6-10}$ aryloxycarbonyl, 5-10 membered heteroaryloxycarbonyl, $C_{6\sim10}$ arylaminoformyl or 5~10 membered heteroarylaminoformyl, which can be optionally substituted by at least one of the following substituents: halogen, $C_{1-6}$ alkyl, $C_{3-6}$ cycloalkyl, 3-7 membered heterocycloalkyl, $C_{6-10}$ aryl, and 5-10 membered heteroaryl.

[2] The following compounds or their pharmaceutically acceptable salts, esters, solvates, optical isomers, tautomers, isotope markers, or prodrugs, including:

(1) (S)-2-(2-chloro-6-fluorobenzoylamino)-3-(4-(5',6'-difluoro-2'-oxospiro[cyclopropane-1,3'-indoline]-1'-yl)phenyl)propionic acid;

(2) (S)-3-(4-(7'-chloro-2'-oxospiro [cyclopropane-1,3'-indoline]-1'-yl)phenyl)-2-(2-chloro-6-fluorobenzoylamino) propionic acid;

(3) (S)-2-(2,6-dichlorobenzoylamino)-3-(4-(5',6'-difluoro-2'-oxospiro [cyclopropane-1,3'-indoline]-1'-yl) phenyl) propionic acid;

(4) (S)-2-(2,6-dichlorobenzoylamino)-3-(4-(7-methoxy-2'-oxospiro[cyclopropane-1,3'-indoline]-1'-yl) phenyl) propionic acid;

(5) (S)-3-(4-(6'-chloro-2'-oxospiro [cyclopropane-1,3'-indoline]-1-yl)phenyl)-2-(2,6-dichlorobenzoylamino) propionic acid;

(6) (S)-2-(2,6-dichlorobenzoylamino)-3-(4-(6'-fluoro-2'-oxospiro [cyclopropane-1,3'-indoline]-1'-yl) phenyl) propionic acid;

(7) (S)-2-(2,6-dichlorobenzoylamino)-3-(4-(7-fluoro-2'-oxospiro[cyclopropane-1,3'-indoline]-1'-yl) phenyl) propionic acid;

(8) (S)-2-(2,6-dichlorobenzoylamino)-3-(4-(2'-oxospiro [cyclopropane-1,3'-indoline]-1'-yl) phenyl) propionic acid;

(9) (S)-3-(4-(7-chloro-2-oxo-2',3',5',6'-tetrahydrospiro [indoline-3,4'-pyran]-1-yl) phenyl)-2-(2-chloro-6-fluorobenzoylamino) propionic acid;

(10) (S)-3-(4-(6'-chloro-5'-fluoro-2'-oxospiro [cyclopropane-1,3'-indoline]-1'-yl) phenyl)-2-(2-chloro-6-fluorobenzoylamino) propionic acid;

(11) (S)-2-(2-chloro-6-fluorobenzoylamino)-3-(4-(5'-fluoro-2-oxospiro [cyclopropane-1,3'-indoline]-1'-yl) phenyl) propionic acid;

(12) (S)-3-(4-(7-chloro-3,3-dimethyl-2-oxoindoline-1-yl) phenyl)-2-(2-chloro-6-fluorobenzoyl amino) propionic acid;

(13) (S)-3-(4-(5'-chloro-2'-oxospiro [cyclopropane-1,3'-indoline]-1'-yl) phenyl)-2-(2-chloro-6-fluorobenzoylamino) propionic acid;

(14) (S)-2-(2-chloro-6-fluorobenzoylamino)-3-(4-(6'-(dimethylamino)-5'-fluoro-2'-oxospiro [cyclopropane-1,3'-indoline]-1'-yl) phenyl) propionic acid;

(15) (S)-2-(2-chloro-6-fluorobenzoylamino)-3-(4-(5'-(dimethylamino)-2'-oxospiro [cyclopropane-1,3'-indoline]-1'-yl) phenyl) propionic acid;

(16) (S)-2-(2-chloro-6-fluorobenzoylamino)-3-(4-(6'-fluoro-2-oxospiro [cyclopropane-1,3'-indoline]-1'-yl) phenyl) propionic acid;

(17) (S)-2-(2-chloro-6-fluorobenzoylamino)-3-(4-(7-fluoro-2-oxospiro [cyclopropane-1,3'-indoline]-1'-yl) phenyl) propionic acid;
(18) (S)-2-(2-chloro-6-fluorobenzoylamino)-3-(4-(6',7'-difluoro-2'-oxospiro [cyclopropane-1,3'-indoline]-1'-yl) phenyl) propionic acid;
(19) (S)-2-(2,6-dichlorobenzoylamino)-3-(4-(2-Oxospiro [cyclopropane-1,3'-pyrrolo [2,3-b]pyridine]-1'(2'H)-yl) phenyl) propionic acid;
(20) (S)-3-(4-(7'-chloro-2'-oxospiro [cyclopropane-1,3'-indoline]-1'-yl) phenyl)-2-(2,4,6-trichlorobenzoylamino) propionic acid;
(21) (S)-3-(4-(7'-chloro-2'-oxospiro [cyclopropane-1,3'-indoline]-1'-yl) phenyl)-2-(2,6-dichloro-4-(diethylamino) benzoylamino) propionic acid;
(22) (S)-3-(4-(7'-chloro-2'-oxospiro [cyclopropane-1,3'-indoline]-1'-yl) phenyl)-2-(2,6-dichloro-4-morpholinylbenzoylamino) propionic acid;
(23) (2S)-2-(4-(2-oxa-5-azabicyclo [2.2.1] hept-5-yl)-2,6-dichlorobenzoylamino)-3-(4-(7'-chloro-2'-oxospiro [cyclopropane-1,3'-indoline]-1'-yl) phenyl) propionic acid;
(24) (S)-3-(4-(7-chloro-2-oxospiro [cyclopropane-1,3'-indoline]-1'-yl) phenyl)-2-(2,6-dichloro-4-(4-morpholinylpiperidin-1-yl) benzoylamino) propionic acid;
(25) (S)-3-(4-(7-chloro-3-methyl-2-oxo-2,3-dihydro-1H-benzo [d] imidazol-1-yl) phenyl)-2-(2-chloro-6-fluorobenzoylamino) propionic acid;
(26) (S)-3-(4-(5-chloro-3-cyclopropyl-2-oxo-2,3-dihydro-1H-benzo [d] imidazol-1-yl) phenyl)-2-(2,6-dichlorobenzoylamino) propionic acid;
(27) (S)-3-(4-(6-chloro-3-cyclopropyl-2-oxo-2,3-dihydro-1H-benzo[d] imidazol-1-yl) phenyl)-2-(2,6-dichlorobenzoylamino) propionic acid;
(28) (S)-3-(4-(7-chloro-3-cyclopropyl-2-oxo-2,3-dihydro-1H-benzo[d] imidazol-1-yl) phenyl)-2-(2,6-dichlorobenzoylamino) propionic acid;
(29) (S)-3-(4-(7-chloro-3-methyl-2-thio-2,3-dihydro-1H-benzo [d] imidazol-1-yl) phenyl)-2-(2-chloro-6-fluorobenzoylamino) propionic acid;
(30) (S)-2-(2-chloro-6-fluorobenzoylamino)-3-(4-(3-cyclopropyl-7-fluoro-2-oxo-2,3-dihydro-1H-benzo [d] imidazol-1-yl) phenyl) propionic acid;
(31) (S)-3-(4-(7-chloro-2-oxo-3-(tetrahydro-2H-pyran-4-yl)-2,3-dihydro-1H-benzo [d]imidazol-1-yl) phenyl)-2-(2-chloro-6-fluorobenzoylamino) propionic acid;
(32) (S)-3-(4-(7-chloro-3-(1-methylpiperidin-4-yl)-2-oxo-2,3-dihydro-1H-benzo [d]imidazol-1-yl) phenyl)-2-(2-chloro-6-fluorobenzoylamino) propionic acid;
(33) (S)-2-(2-chloro-4-fluorobenzoylamino)-3-(4-(7-fluoro-3-methyl-2-oxo-2,3-dihydro-1H-benzo [d] imidazol-1-yl) phenyl) propionic acid;
(34) (S)-2-(2-chloro-6-fluorobenzoylamino)-3-(4-(5,7-difluoro-3-methyl-2-oxo-2,3-dihydro-1H-benzo [d] imidazol-1-yl) phenyl) propionic acid;
(35) (S)-2-(2-chloro-6-fluorobenzoylamino)-3-(4-(5,6-dichloro-3-methyl-2-oxo-2,3-dihydro-1H-benzo [d] imidazol-1-yl) phenyl) propionic acid;
(36) (S)-2-(2-chloro-6-fluorobenzoylamino)-3-(4-(6,7-difluoro-3-methyl-2-oxo-2,3-dihydro-1H-benzo [d] imidazol-1-yl) phenyl) propionic acid;
(37) (S)-2-(2-chloro-6-fluorobenzoylamino)-3-(4-(4,5-difluoro-3-methyl-2-oxo-2,3-dihydro-1H-benzo [d] imidazol-1-yl) phenyl) propionic acid;
(38) (S)-2-(2-chloro-6-fluorobenzoylamino)-3-(4-(7-methoxy-3-methyl-2-oxo-2,3-dihydro-1H-benzo [d] imidazol-1-yl) phenyl) propionic acid;
(39) (S)-2-(2-chloro-6-fluorobenzoylamino)-3-(4-(6-(dimethylamino)-3-methyl-2-oxo-2,3-dihydro-1H-benzo [d] imidazol-1-yl) phenyl) propionic acid;
(40) (S)-2-(2-chloro-6-fluorobenzoylamino)-3-(4-(5-(dimethylamino)-3-methyl-2-oxo-2,3-dihydro-1H-benzo [d] imidazol-1-yl) phenyl) propionic acid;
(41) (S)-3-(4-(7-chloro-3-methyl-2-oxo-2,3-dihydro-1H-benzo [d] imidazol-1-yl) phenyl)-2-(2,4,6-trichlorobenzoylamino) propionic acid; and
(42) (S)-3-(4-(7-chloro-3-methyl-2-oxo-2,3-dihydro-1H-benzo [d] imidazol-1-yl) phenyl)-2-(2,6-dichloro-4-morpholinylbenzoylamino) propionic acid.

[3] A pharmaceutical composition comprising the aforementioned compounds or pharmaceutically acceptable salts, esters, solvates, optical isomers, tautomers, isotope markers, or prodrugs thereof.

[4] The use of the aforementioned compounds or pharmaceutically acceptable salts, esters, solvates, optical isomers, tautomers, isotope markers or prodrugs thereof, or pharmaceutical compositions thereof, used for preparation of drugs for prevention and/or treatment of diseases and/or symptoms at least partially mediated by α4β7 integrin.

[5] The aforementioned compounds or pharmaceutically acceptable salts, esters, solvates, optical isomers, tautomers, isotope markers or prodrugs thereof, or pharmaceutical compositions thereof, used for prevention and/or treatment of diseases and/or symptoms at least partially mediated by α4β7 integrin.

[6] A method for preventing and/or treating diseases and/or symptoms mediated at least partially by α4β7 integrin, which includes the following steps: administrating the aforementioned compounds or their pharmaceutically acceptable salts, esters, solvates, optical isomers, tautomers, isotope markers or prodrugs thereof, or the aforementioned drug compositions thereof, to individuals in need.

The novel N-(benzoyl)-phenylalanine compound of the present invention has excellent α4β7 integrin binding inhibitory activity, therefore, the novel N-(benzoyl)-phenylalanine compound of the present invention can provide α4β7 dependent therapeutic or preventive agents for autoimmune diseases and inflammatory bowel diseases (Krohn's disease and ulcerative colitis). The compound of the present invention has a high blood drug concentration or bioavailability when administered orally, making it very useful as an oral administration drug. In addition, the compound of the present invention has good stability in acidic and alkaline solutions and can be used for the development of various dosage forms.

SPECIFIC IMPLEMENTATION METHODS

Definition of Terms

Unless otherwise defined, the meanings of the terms used in this article are the same as those commonly understood by those skilled in the field. The technical intent used in this article refers to the commonly understood techniques in the field, including changes or equivalent replacements that are obvious to those skilled in the field. Although the following terms are easy to understand for those skilled in the field, they are still elaborated as follows to better explain the present invention.

The terms "including". "comprising", "having", or "involving" and their other variant forms in this article refer to inclusive or open set concepts, and do not exclude other elements or methods/steps that are not enumerated. Technicians in this field should understand that the aforementioned terms, such as "including", cover the meaning of "being . . . composed of".

The term "one or more" or similar expression "at least one" refers to, for example, 1, 2, 3, 4, 5, 6, 7, 8, 9, 10 or more.

When the lower and upper limits of a numerical range are disclosed, any numerical value or any sub-range that falls within that range indicates specific disclosure. Specifically, each numerical range of the parameters disclosed in this article (for example, in the form of "approximate a-b", or equivalent "approximate a-b", or equivalent "approximate a-b") should be understood to cover each numerical value and sub-range within it. For example, "$C_{1-6}$" refers to any sub-range and each point value that are covered in it, such as $C_{2-5}$, $C_{3-4}$, $C_{1-2}$, $C_{1-3}$, $C_{1-4}$, $C_{1-5}$, etc., as well as $C_1$, $C_2$, $C_3$, $C_4$, $C_5$, $C_6$, etc. For example, '3-6 membered' should be understood as covering any sub-range and each point value, such as 34 membered, 3-5 membered, 3-6 membered, 4-5 membered, 4-6 membered, 5-6 membered, etc., as well as 3, 4, 5, 6 membered, etc.

The term "pharmaceutically acceptable salts" refers to the salts of the compound of the present invention, which is basically non-toxic to organisms, and generally includes (but is not limited to) the salts generated by the reaction of the compound of the present invention with pharmaceutically acceptable inorganic acid/organic acid/acidic amino acid or inorganic base/organic base/basic amino acid. Such salts are also called acid addition salts or base addition salts. Suitable salts can be found in Stahl and Wermuth's "Handbook of Pharmaceutical Salts: Properties, Selection, and Use" (Wiley VCH, 2002). The pharmaceutically acceptable salts of the compound of the present invention include (but are not limited to) metal salts (such as sodium salts, potassium salts, ammonium salts, calcium salts, magnesium salts, zinc salts, and aluminum salts, etc.), organic amine salts (such as dimethylamine salts, trimethylamine salts, diethylamine salts, trimethylamine salts, and diisopropylethylamine salts, etc.), and basic amino acids (such as lysine salts, and arginine salts, etc.) formed by acidic groups (such as carboxyl); inorganic salts (e.g., hydrochlorides, sulfates, and phosphates, etc.) and organic salts (e.g., maleates, tartrates, succinates, citrates, and acetates, etc.) formed by basic groups (e.g., amino).

The term "esters" refers to the esters of the compound of the present invention, which is basically non-toxic to organisms, and generally includes (but is not limited to) the esters generated by the reaction of the hydroxyl of the compound of the present invention with pharmaceutically acceptable inorganic acid/organic acid/acidic amino acid or the reaction of the carboxyl with other pharmaceutically acceptable alcohols/phenols/compounds with hydroxyl.

The term "solvates" refers to complexes generated by the interaction of the compound of the present invention with pharmaceutically acceptable solvents, with specific spatial arrangements and solute/solvent molecular molar ratios. It typically includes (but is not limited to) solvates generated by the compound of the present invention with polar protic solvents/polar aprotic solvents/non-polar solvents, such as hydrates and alcohols, etc.

The term "optical isomers" refers to a plurality of isomers with different optical rotations due to the fact that the compound of the invention has chiral elements (such as chiral centers, chiral axes, and chiral planes, etc.), which generally include (but are not limited to) the enantiomer and non-enantiomer of the compound of the present invention.

The term 'tautomers' refers to multiple isomers with different structural formulas resulting from the tautomerism of the compound of the present invention, typically including (but not limited to) ketone-enol tautomerism, and amide-iminol tautomerism, etc.

The term "isotope markers" refers to compounds formed by replacing at least one atom in the compound of the present invention with its isotope atom, typically including (but not limited to) deuterium substituted compounds in which hydrogen atoms are substituted with deuterium atoms.

The term 'prodrugs' refers to derivative compounds of the compound of the present invention that can be directly or indirectly obtained after the drug is administrated to an individual (for example, the drug is converted into the compound of the present invention through the oxidation, reduction, and hydrolysis, etc. of enzymes or gastric acid under physiological conditions within the body). Specifically, derived compounds or prodrugs are compounds that can enhance the bioavailability (such as those that are more easily absorbed into the bloodstream) of the compound of the present invention when administrated to individuals, or compounds that promote the delivery of the parent compound to the site of action (such as the lymphatic system). For suitable prodrugs, see T Higuchi. V. Stella, Pro-drugs as Novel Drug Delivery Systems [J], American Chemical Society. Vol. 14, 1975. In addition, the present invention also covers the compound of the present invention containing protective groups. In any process of preparing the compound of the present invention, protecting sensitive or reactive groups on any relevant molecule may be necessary and/or desirable, thereby a form of chemical protection for the compound of the present invention is generated. For example, when the compound of the present invention has a carboxyl, the corresponding prodrugs can be prepared through esterification or amidation; when the compound of the present invention has an amino, the corresponding prodrugs can be prepared by amidation, phosphorylation, or alkylation; when the compound of the present invention has a hydroxyl, corresponding prodrugs can be prepared by esterification, phosphorylation, or alkylation. For suitable protective groups, see T. W. Greene, P. G. M. Wuts. Protective Groups in Organic Synthesis [M], John Wiley & Sons, 2006. By using methods known in this field, these protective groups can be removed at appropriate subsequent stages.

Unless otherwise specified, the term "halogen" used in this article refers to fluorine (F), chlorine (Cl), bromine (Br), and/or iodine (I).

Unless otherwise specified, the term "hydroxyl" used in this article refers to —OH.

Unless otherwise specified, the term "amino" used in this article refers to $—NH_2$, and the term "substituted amino" refers to the mono-substituted form of the amino-NHR or bi-substituted form —NRR'.

Unless otherwise specified, the term "aldehyde group" used in this article refers to —CH(═O).

Unless otherwise specified, the term "carboxyl" used in this article refers to —C(═O)OH.

Unless otherwise specified, the term "cyano" used in this article refers to —CN.

Unless otherwise specified, the term 'nitro' used in this article refers to $—N(═O)_2$.

Unless otherwise specified, the term "alkyl" used in this article refers to linear or branched saturated aliphatic hydrocarbonyl. For example, the term "$C_{1-6}$ alkyl" used in this article refers to linear or branched alkyl (such as methyl, ethyl, n-propyl, isopropyl, n-butyl, sec-butyl, isobutyl, tert butyl, n-amyl, isopentyl, neopentyl, and n-hexyl, etc.) with 1 to 6 carbon atoms (such as 1, 2, 3, 4, 5, or 6 carbon atoms). When it is optionally substituted by one or more (such as 1 to 3) substituents described in this article (for example, when it is substituted by halogens, the group is "$C_{1-6}$ haloalkyl", such as —$CF_3$, —$C_2F_5$, —$CHF_2$, —$CH_2F$, —$CH_2CF_3$, —$CH_2Cl$, and —$CH_2CH_2F_3$, etc.).

Unless otherwise specified, the term "alkenyl" used in this article refers to aliphatic hydrocarbonyl with one or more (such as 1 to 3) linear or branched carbon-carbon double bonds. For example, the term "$C_{2-6}$ alkenyl" used in this article refers to alkenyls with 2 to 6 carbon atoms and one, two, or three carbon-carbon double bonds (such as vinyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl, etc.), which can be optionally substituted by one or more (such as 1-3) substituents described in this article.

Unless otherwise specified, the term "alkoxy" used in this article refers to the aforementioned alkyl, namely —O-alkyl, which is connected to the parent molecule through oxygen atoms. For example, the term "$C_{1-6}$ alkoxy" used in this article refers to alkoxy (such as methoxy, ethoxy, isopropoxy, and tert butoxy, etc.) with 1 to 6 carbon atoms (such as 1, 2, 3, 4, 5, or 6 carbon atoms), which can be optionally substituted by one or more (such as 1-3) substituents described in this article (for example, when it is substituted by halogen, the group is "$C_{1-6}$ halogenated alkoxy", such as —$OCF_3$, —$OC_2F_5$, —$OCHF_2$, and —$OCH_2Cl$, etc.).

Unless otherwise specified, the term "alkylthio" used in this article refers to the aforementioned alkyl, i.e. —S-alkyl, which is connected to the parent molecule through sulfur atoms. For example, the term "$C_{1-6}$ alkylthio" used in this article refers to an alkylthio group (such as methylthio, ethylthio, isopropyl thio, and tert butylthio, etc.) with 1 to 6 carbon atoms (such as 1, 2, 3, 4, 5, or 6 carbon atoms), which is optionally substituted by one or more (such as 1-3) substituents described in this article (for example, when it is substituted by halogen, the group is "$C_{1-6}$ haloalkythio", such as —$SCF_3$, —$SC_2F_5$, —$SCHF_2$, and —$SCH_2Cl$, etc.).

Unless otherwise specified, the term "alkanoyl" used in this article refers to the aforementioned alkyl, namely —C(═O)-alkyl, which is connected to the parent molecule through carbonyl. For example, the term "$C_{1-6}$ alkanoyl" used in this article refers to alkanoyl (such as acetyl, and isobutyryl, etc.) with 1 to 6 carbon atoms (such as 1, 2, 3, 4, 5, or 6 carbon atoms).

Unless otherwise specified, the term "(di) alkylamino" used in this article refers to the aforementioned alkyl, namely —NH alkyl or —$N(alkyl)_2$, which are connected to the parent molecular through nitrogen atoms. For example, the term "$C_{1-6}$ alkylamino" used in this article refers to alkylamino (such as ethylamino and isopropylamino, etc.) with 1 to 6 carbon atoms (such as 1, 2, 3, 4, 5, or 6 carbon atoms), while the term "di ($C_{1-6}$ alkyl) amino" used in this article refers to dialkylamino (such as dimethylamino and diethylamino, etc.) with two groups of 1 to 6 carbon atoms (such as 1, 2, 3, 4, 5, or 6 carbon atoms).

Unless otherwise specified, the term "alkoxycarbonyl" used in this article refers to the aforementioned alkyl, namely —C(═O)—O-alkyl, which is sequentially connected to the parent molecule through oxygen atoms and carbonyl. For example, the term "$C_{1-6}$ alkoxycarbonyl" used in this article refers to alkoxycarbonyl (such as ethoxycarbonyl, isopropoxycarbonyl, and tert butoxycarbonyl, etc.) with 1 to 6 carbon atoms (such as 1, 2, 3, 4, 5, or 6 carbon atoms).

Unless otherwise specified, the term "alkanoyloxy" used in this article refers to the aforementioned alkyl, namely —O—C(═O)-alkyl, which is sequentially connected to the parent molecular through carbonyl and oxygen atoms. For example, the term "$C_{1-6}$ alkanoyloxy" as used in this article refers to alkanoyloxy (such as acetoxy, isobutyryloxy, and pivaloyloxy, etc.) with 1 to 6 carbon atoms (such as 1, 2, 3, 4, 5, or 6 carbon atoms).

Unless otherwise specified, the term "alkyl amido" used in this article refers to the aforementioned alkyl, namely —NH—C(═O)-alkyl, which is sequentially connected to the parent molecular through carbonyl and nitrogen atoms. For example, the term "$C_{1-6}$ alkyl amido" used in this article refers to alkyl amido (such as acetylamino, isobutyrylamino, and pivaloylamino, etc.) with 1 to 6 carbon atoms (such as 1, 2, 3, 4, 5, or 6 carbon atoms).

Unless otherwise specified, the term "aminoformyl" used in this article refers to —C(═O)—$NH_2$, and "(di) alkyl aminoformyl" refers to the aforementioned alkyl, namely —C(═O)—NH alkyl or —C(═O)—$N(alkyl)_2$, which are sequentially connected to the parent molecule through amino and carbonyl. For example, the term "$C_{1-6}$ alkyl aminoformyl" used in this article refers to alkyl aminoformyl (such as ethylaminoformyl, isopropylaminoformyl, etc.) with 1 to 6 carbon atoms (such as 1, 2, 3, 4, 5, or 6 carbon atoms), and the term "di ($C_{1-6}$ alkyl) aminoformyl" used in this article refers to dialkyl aminoformyl (such as diethylaminoformyl, diisopropylaminoformyl, etc.) with two groups of 1 to 6 carbon atoms (such as 1, 2, 3, 4, 5, or 6 carbon atoms).

Unless otherwise specified, the term "alkoxy sulfonyl" used in this article refers to the aforementioned alkyl, namely —$S(═O)_2$—O-alkyl, which is sequentially connected to the parent molecular through oxygen atoms and sulfonyl. For example, the term "$C_{1-6}$ alkoxy sulfonyl" used in this article refers to the alkoxy sulfonyl (such as ethoxy sulfonyl, isopropoxy sulfonyl, and tert butoxy sulfonyl, etc.) with 1 to 6 carbon atoms (such as 1, 2, 3, 4, 5, or 6 carbon atoms).

Unless otherwise specified, the term "alkyl sulfonyloxy" used in this article refers to the aforementioned alkyl, namely —O—$S(═O)_2$-alkyl, which is sequentially connected to the parent molecular part through sulfone groups and oxygen atoms. For example, the term "$C_{1-6}$ alkyl sulfonyloxy" used in this article refers to alkyl sulfonyloxy (such as ethylsulfonyloxy, isopropylsulfonyloxy, and tert butylsulfonyloxy, etc.) with 1 to 6 carbon atoms (such as 1, 2, 3, 4, 5, or 6 carbon atoms).

Unless otherwise specified, the term "alkyl sulfonyl amide" used in this article refers to the aforementioned alkyl group, namely —NH—S(═O))-alkyl, which is sequentially connected to the parent molecular through sulfone groups and nitrogen atoms. For example, the term "$C_{1-6}$ alkylsulfonamide" used in this article refers to alkylsulfonamide groups (such as ethylsulfonamide, isopropylsulfonamide, and tert butylsulfonylamino, etc.) with 1 to 6 carbon atoms (such as 1, 2, 3, 4, 5, or 6 carbon atoms).

Unless otherwise specified, the term "amino sulfonyl" used in this article refers to —$S(═O)_2$—$NH_2$, and the term "(di) alkyl amino sulfonyl" refers to the aforementioned alkyl, namely —$S(═O)_2$—NH-alkyl or —$S(═O)_2$—$N(alkyl)_2$, which is sequentially connected to the parent molecular by nitrogen atoms and sulfonyl. For example, the term "$C_{1-6}$ alkylamino sulfonyl" used in this article refers to an alkylamino sulfonyl (such as ethylamino sulfonyl, isopropylamino sulfonyl, etc.) with 1 to 6 carbon atoms (such as 1, 2, 3, 4, 5, or 6 carbon atoms), and the term "di ($C_{1-6}$ alkyl) amino sulfonyl" used in this article refers to dialkylamino sulfonyl (such as diethylamino sulfonyl, diisopropylamino sulfonyl, etc.) with two groups of 1-6 carbon atoms (such as 1, 2, 3, 4, 5 or 6 carbon atoms).

Unless otherwise specified, the term "cycloalkyl" used in this article refers to cyclic saturated aliphatic hydrocarbonyl. For example, the term "$C_{3-6}$ cycloalkyl" used in this article refers to cycloalkyl (such as cyclopropyl, cyclobutyl, cyclopentyl, and cyclohexyl, etc.) with 3 to 6 cyclic carbon atoms (such as 3, 4, 5, or 6 carbon atoms). Unless otherwise specified, the term "cyclopropylene" used in this article refers to a cyclic saturated aliphatic hydrocarbonyl that connects two other segments simultaneously. For example, the term "$C_{3-6}$ cycloalkylene" used in this article refers to a cycloalkylene group (such as a cyclopropylene group) with 3 to 6 cyclic carbon atoms (such as 3, 4, 5, or 6 carbon atoms).

Unless otherwise specified, the term "heterocyclic alkyl" used in this article refers to saturated aliphatic hydrocarbonyl with one or more carbon atoms (such as 1, 2, 3, 4, 5, 6, 7, 8, or 9) and one or more segments (such as 1, 2, 3, or 4) independently selected from —O—, —S—, —S(═O)—, —S(═O)$_2$—, and —NR— (R represents hydrogen atoms or substituents, such as alkyl or cycloalkyl). For example, the term "3-7-membered heterocyclic alkyl" used in this article refers to heterocyclic alkyl (such as epoxyethanyl (oxocyclopropyl), cyclothioethanyl (thiocyclopropyl), cyclonitroethanyl (nitrocyclopropyl), nitrocyclobutyl, oxocynobutyl, thiocycloputyl, tetrahydrofuranyl, 1,3-dioxcyclopentanyl, tetrahydrothienyl, pyrrolidine, pyrrolidone, imidazolidinyl, pyrazolidine, tetrahydropyran, tetrahydropyran, piperidine, azapyran, morpholine, thiomorpholine, 1,4-thiaxalkyl, 1,4-dioxane, 1,4-dithialkyl, piperazine, 1,3,5-trioxalkyl, 1,3,5-triathialkyl, and 1,4-thiazinyl, etc.) with 3 to 7 cyclic atoms (such as 3, 4, 5, 6, or 7 atoms). Unless otherwise specified, the term "sub-heterocyclic alkyl" used in this article refers to saturated aliphatic hydrocarbonyl with one or more carbon atoms (such as 1, 2, 3, 4, 5, 6, 7, 8, or 9) and one or more segments (such as 1, 2, 3, or 4) independently selected from —O—, —S—, —S(═O)—, —S(═O)—, and —NR— (R represents hydrogen atoms or substituents, such as alkyl or cycloalkyl). For example, the term "3-7-membered sub-heterocyclic alkyl" used in this article refers to the sub-heterocyclic alkyl (such as tetrahydro-2H-pyran-4-yl, etc.) with 3 to 7 cyclic atoms (such as 3, 4, 5, 6, or 7 atoms).

Unless otherwise specified, the term "aryl" used in this article refers to aromatic hydrocarbonyl with conjugated π-electron systems that are single or fused rings. For example, the term "$C_{6-10}$ aryl" used in this article refers to aryl (such as phenyl, naphthyl, etc.) with 6 to 10 (such as 6, 7, 8, 9, or 10) cyclic carbon atoms, which is optionally substituted by one or more substituents described in this article (such as methylphenyl substituted by $C_{1-6}$ alkyl, and the chlorophenyl substituted by halogen, etc.).

Unless otherwise specified, the term "heteroaryl" used in this article refers to aromatic groups with conjugated π-electron systems that are single or fused ring containing one or more (such as 1, 2, 3, or 4) carbon atoms and one or more (such as 1, 2, 3, or 4) segments independently selected from —O—, —S—, —S(═O)—, —S(═O)—, —N═, and —NR— (R represents hydrogen atoms or substituents, such as alkyl or cycloalkyl). As used in this article, the "5-10 membered heteroaryl" refers to the heteroaryl (such as thiophenyl, furanyl, pyrrolyl, thiazolyl, oxazolyl, imidazolyl, isothiazolyl, isoxazolyl, pyrazolyl, thiadiazole, oxadiazolyl, triazolyl, tetrazolyl, etc., or such as pyridinyl, pyridazinyl, pyrimidinyl, pyrazinyl, triazinyl, etc., or its benzo derivatives, such as indazolyl, indolyl, isoindolyl, quinolinyl, isoquinoline, etc., or pyrazopyridinyl, pyrrolopyrimidinyl, pyrrolo Pyridinyl, pyrazole pyrimidine, etc.), which can be optionally substituted by one or more substituents described in this article (such as a methylpyridinyl substituted by C1-C6 alkyl, and a chloropyridinyl substituted by halogen, etc.). If the valence bond requirement is met, the heteroaryl can be connected to the parent molecular through any cyclic atom. If the valence bond requirement is met, the heteroaryl can be connected to other groups (or segments) through any carbon atom or heteroatom (such as N atom) in the ring. Moreover, the heteroaryl can be optionally fused on the aryl, heterocycloalkyl and cycloalkyl, wherein the ring connected with the parent structure is a heteroaryl.

Unless otherwise specified, the terms "aryloxy" and "heteroaryloxy" used in this article refer to the aforementioned aryl or heteroaryl, namely —O-aryl (such as phenoxy, naphthalene-1-methoxy, etc.) and —O-heteroaryl (such as furan-2-methoxy, pyridine-4-methoxy, etc.), which are connected to the parent molecular through oxygen atoms.

Unless otherwise specified, the terms "arylthio" and "heteroaryl thio" used in this article refer to the aforementioned aryl or hetero aryl, namely —S-aryl (such as phenylthio, naphthalene-1-ylthio, etc.) and —S-heteroaryl (such as furan-2-ylthio, pyridine-4-ylthio, etc.), which are connected to the parent molecular through sulfur atoms.

Unless otherwise specified, the terms "arylcarbonyl" and "heteroarylcarbonyl" used in this article refer to the aforementioned aryl or heteroaryl, namely —C(═O)-aryl (such as benzoyl, 1-naphthoyl, etc.) and —C(═O)-heteroaryl (such as furoyl, nicotinyl, etc.), which are connected to the parent molecule through carbonyl.

Unless otherwise specified, the terms "arylamino" and "heteroarylamino" used in this article refer to the aforementioned aryl or heteroaryl, namely —NH-aryl (such as phenylamino, naphthalen-1-ylamino, etc.) and —NH-heteroaryl (such as furan-2-methoxy, pyridine-4-methoxy, etc.), which are connected to the parent molecular through nitrogen atoms.

Unless otherwise specified, the terms "aryloxyacyl" and "heteroaryloxyacyl" used in this article refer to the aforementioned aryl or heteroaryl, namely —C(═O)—O-aryl (such as phenoxyformyl) and —C(═O)—O-heteroaryl (such as furan-2-methoxyformyl), which are sequentially connected to the parent molecule through oxygen atoms and carbonyl.

Unless otherwise specified, the terms "arylformyloxy" and "heteroarylformyloxy" used in this article refer to the aforementioned aryl or heteroaryl, namely —O—C(═O)-aryl (such as benzoyloxy) and —O—C(═O)-heteroaryl (such as furoyloxy), which are sequentially connected to the parent molecule through carbonyl and oxygen atoms.

Unless otherwise specified, the terms "arylformamido" and "heteroarylformamido" used in this article refer to the aforementioned aryl or heteroaryl, namely —NH—C(═O)-aryl (such as benzoylamino) and —NH—C(═O)-heteroaryl (such as furoylamino), which are sequentially connected to the parent molecule through carbonyl and nitrogen atoms.

Unless otherwise specified, the terms "arylaminoformyl" and "heteroarylaminoformyl" used in this article refer to the aforementioned aryl or heteroaryl, namely —C(═O)—NH-aryl (such as phenylaminoformyl) and —C(═O)—NH-heteroaryl (such as furan-2-ylaminoformyl), which are sequentially connected to the parent molecular through nitrogen atoms and carbonyl.

Unless otherwise specified, the terms "aryloxy sulfonyl" and "heteroaryloxy sulfonyl" used in this article refer to the aforementioned aryl or heteroaryl, namely —S(═O)$_2$—O-aryl (such as phenoxy sulfonyl) and —S(═O)$_2$—O-heteroaryl (such as furan-2-yloxy sulfonyl), which are sequentially connected to the parent molecular by oxygen atoms and sulfonyl.

Unless otherwise specified, the terms "arylsulfonyloxy" and "heteroarylsulfonyloxy" used in this article refer to the aforementioned aryl or heteroaryl, namely —O—S(═O)$_2$-aryl (such as benzenesulfonyloxy) and —O—S(═O)$_2$-heteroaryl (such as furan-2-sulfoyloxy), which are sequentially connected to the parent molecular through sulfones and oxygen atoms.

Unless otherwise specified, the terms "arylsulfonylamino" and "heteroarylsulfonylamino" used in this article refer to the aforementioned aryl or heteroaryl, namely —NH—S(═O)$_2$-aryl (such as benzenesulfonylamino) and —NH—S(═O)$_2$-heteroaryl (such as furan-2-sulfonylamino), which are sequentially connected to the parent molecule through sulfones and nitrogen atoms.

Unless otherwise specified, the terms "arylaminosulfonyl" and "heteroarylaminosulfonyl" used in this article refer to the aforementioned aryl or heteroaryl, namely —S(═O)$_2$—NH-aryl (such as phenylaminosulfonyl) and —S(═O)$_2$—NH-heteroaryl (such as furan-2-ylaminosulfonyl), which are sequentially connected to the parent molecular through nitrogen atoms and sulfonyl.

Unless otherwise specified, the term "independently" used in this article refers to at least two functional groups (or segments) with the same or similar value range that exist in the structure and can have the same or different meanings in specific situations. For example, if $R_1$ and $R_2$ are independently hydrogen, halogen, hydroxyl, cyano, alkyl or aryl, then when $R_1$ is hydrogen, $R_2$ can be hydrogen, halogen, hydroxyl, cyano, alkyl or aryl; similarly, when $R_2$ is hydrogen. Rr can be hydrogen, halogen, hydroxyl, cyano, alkyl or aryl.

Unless otherwise specified, the term "substitution" and its variant forms used in this article mean that one or more (such as 1, 2, 3 or 4) atoms or atomic clusters (such as hydrogen atoms) on the designated atoms am substituted by other equivalents, provided that the normal valence of the designated atoms or atomic clusters in the current situation is not exceeded and stable compounds can be formed. Unless otherwise specified, the connecting site of the substituent in this article can be any suitable position of the substituent.

Compounds of the General Formula

The present invention provides a compound as shown in general formula (1) or pharmaceutically acceptable salts, esters, solvates, optical isomers, tautomers, isotope markers, or prodrugs thereof, (1)

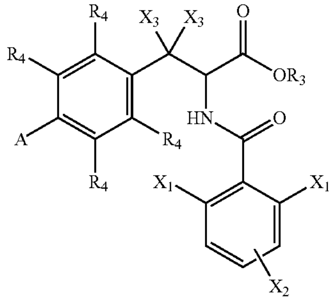

Where, $R_3$ is hydrogen, $C_{1-6}$ alkyl, $C_{1-6}$ haloalkyl, $C_{2-6}$ alkenyl, $C_{2-6}$ alkynyl, $C_{3-6}$ cycloalkyl, 3-7 membered heterocyclic alkyl, $C_{6-10}$ aryl, or 5-10 membered heteroaryl, which can be optionally substituted by at least one of the following substituents: halogen, $C_{1-6}$ alkyl, $C_{3-6}$ cycloalkyl, 3-7 membered heterocyclic alkyl, $C_{6-10}$ aryl, and 5-10 membered heteroaryl;

Each $R_4$ is independently hydrogen or halogen;

Each $X_1$ is independently hydrogen or halogen;

$X_2$ is hydrogen, halogen, hydroxyl, amino, aldehyde, carboxyl, cyano, nitro, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylthio, $C_{1-6}$ haloalkythio, $C_{1-6}$ alkanoyl, $C_{1-6}$ alkylamino, di ($C_{1-6}$ alkyl) amino, $C_{1-6}$ alkoxycarbonyl, $C_{1-6}$ alkanoyloxy, $C_{1-6}$ alkyl amido, aminoformyl, $C_{1-6}$ alkyl aminoformyl, di ($C_{1-6}$ alkyl) carbamoyl, $C_{1-6}$ alkoxy sulfonyl, $C_{1-6}$ alkyl sulfonyloxy, $C_{1-6}$ alkyl sulfonyl amino, amino sulfonyl, $C_{1-6}$ alkyl amino sulfonyl, di ($C_{1-6}$ alkyl) amino sulfonyl, $C_{3-6}$ cycloalkyl, 3-7-membered heterocyclic alkyl, $C_{6-10}$ aryl, 5-10 membered heteroaryl, $C_{6-10}$ aryloxy, 5-10 membered heteroaryloxy, $C_{6\sim10}$ arylthio, 5-10 membered heteroaryl thio, $C_{6-10}$ arylamino, 5-10 membered heteroarylamino, $C_{6\sim10}$ arylcarbonyl, 5-10 membered heteroarylcarbonyl, $C_{6\sim10}$ aryloxycarbonyl, 5~10 membered heteroaryloxycarbonyl, $C_{6\sim10}$ arylformyloxy, 5~10 membered heteroarylformyloxy, $C_{6\sim10}$ arylformamido, 5~10 membered heteroarylformamido, $C_{6\sim10}$ arylaminoformyl, 5~10 membered heteroarylaminoformyl, $C_{6\sim10}$ aryloxy sulfonyl, 5~10 membered heteroaryloxy sulfonyl, $C_{6\sim10}$ arylsulfonyloxy, 5~10 membered heteroarylsulfonyloxy, $C_{6\sim10}$ arylsulfonylamino, 5~10 membered heteroarylsulfonylamino, $C_{6\sim10}$ arylaminosulfonyl or 5~10 membered heteroarylaminosulfonyl, which is optionally substituted by at least one of the following substituents: halogen, $C_{1\sim6}$ alkyl, $C_{3\sim6}$ cycloalkyl, 3~7 membered heterocyclic alkyl, $C_{6\sim10}$ aryl and 5~10 membered heteroaryl;

Each $X_3$ is independently hydrogen or halogen;

A is a group as shown in general formula (2-1), (2-2), or (2-3), (2-1)

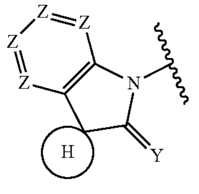

-continued (2-2)

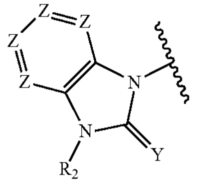

(2-3)

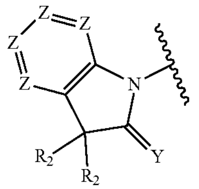

The ring H is a $C_{3-6}$ sub-cyclic alkyl or a 3-7 membered sub-heterocyclic alkyl, which can be optionally substituted by at least one of the following substituents: halogen, $C_{1-6}$ alkyl, $C_{3-6}$ cycloalkyl, 3-7 membered heterocyclic alkyl, $C_{6-10}$ aryl, and 5-10 membered heteroaryl;

Y is either O or S;

Each Z is independently $CR_1$ or N;

If it is present, each $R_1$ is independently hydrogen, halogen, hydroxyl, amino, aldehyde, carboxyl, cyano, nitro, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylthio, $C_{1-6}$ haloalkythio, $C_{1-6}$ alkanoyl, $C_{1-6}$ alkylamino, di ($C_{1-6}$ alkyl) amino, $C_{1-6}$ alkoxycarbonyl, $C_{1-6}$ alkanoyloxy, $C_{1-6}$ alkyl amido, aminoformyl, $C_{1-6}$ alkyl aminoformyl, di ($C_{1-6}$ alkyl) carbamoyl, $C_{1-6}$ alkoxy sulfonyl, $C_{1-6}$ alkyl sulfonyloxy, $C_{1-6}$ alkyl sulfonyl amino, amino sulfonyl, $C_{1-6}$ alkyl amino sulfonyl, di ($C_{1-6}$ alkyl) amino sulfonyl, $C_{3-6}$ cycloalkyl, 3-7-membered heterocyclic alkyl, $C_{6-10}$ aryl, 5-10 membered heteroaryl, $C_{6-10}$ aryloxy, 5-10 membered heteroaryloxy, $C_{6-10}$ arylthio, 5-10 membered heteroaryl thio, $C_{6-10}$ arylamino, 5-10 membered heteroarylamino, $C_{6\sim10}$ arylcarbonyl, 5-10 membered heteroarylcarbonyl, $C_{6\sim10}$ aryloxycarbonyl, 5~10 membered heteroaryloxycarbonyl, $C_{6\sim10}$ arylformyloxy, 5~10 membered heteroarylformyloxy, $C_{6\sim10}$ arylformamido, 5~10 membered heteroarylformamido, $C_{6\sim10}$ arylaminoformyl, 5~10 membered heteroarylaminoformyl, $C_{6\sim10}$ aryloxy sulfonyl, 5~10 membered heteroaryloxy sulfonyl, $C_{6\sim10}$ arylsulfonyloxy, 5~10 membered heteroarylsulfonyloxy, $C_{6\sim10}$ arylsulfonylamino, 5~10 membered heteroarylsulfonylamino, $C_{6\sim10}$ arylaminosulfonyl or 5~10 membered heteroarylaminosulfonyl, which is optionally substituted by at least one of the following substituents: halogen, $C_{1\sim6}$ alkyl, $C_{3\sim6}$ cycloalkyl, 3~7 membered heterocyclic alkyl, $C_{6\sim10}$ aryl and 5~10 membered heteroaryl;

If it is present, each $R_2$ is independently hydrogen, $C_{1-6}$ alkyl, $C_{1-6}$ haloalkyl, $C_{2-6}$ alkenyl, $C_{2-6}$ alkynyl, $C_{1-6}$ alkanoyl, $C_{1-6}$ alkoxycarbonyl, $C_{1-6}$ alkyl amido, aminoformyl, $C_{1-6}$ alkylaminoformyl, di ($C_{1-6}$ alkyl) aminoformyl, $C_{3-6}$ cycloalkyl, 3-7 membered heterocyclic alkyl, $C_{6-10}$ aryl, 5-10 membered heteroaryl, $C_{6-10}$ arylcarbonyl, 5-10 membered heteroarylcarbonyl, $C_{6-10}$ aryloxycarbonyl, 5-10 membered heteroaryloxycarbonyl, $C_{6\sim10}$ arylaminoformyl or 5~10 membered heteroarylaminoformyl, which can be optionally substituted by at least one of the following substituents: halogen, $C_{1-6}$ alkyl, $C_{3-6}$ cycloalkyl, 3-7 membered heterocycloalkyl, $C_{6-10}$ aryl, and 5-10 membered heteroaryl.

In an embodiment of the present invention, $R_3$ in the compound shown in general formula (1) is hydrogen, $C_{1-6}$ alkyl, $C_{1-6}$ haloalkyl, $C_{3-6}$ cycloalkyl, 3-7 membered heterocyclic alkyl, $C_{6-10}$ aryl or 5-10 membered heteroaryl, and the aforementioned groups can be optionally substituted by at least one of the following substituents: halogen, $C_{1-6}$ alkyl, $C_{3-6}$ cycloalkyl, and 3-7 membered heterocyclic alkyl; Preferably, $R_3$ is hydrogen, $C_{1-6}$ alkyl, $C_{1-6}$ haloalkyl, $C_{3-6}$ cycloalkyl, or 3-7-membered heterocyclic alkyl, and the aforementioned groups can be optionally substituted by at least one of the following substituents: halogen and $C_{1-6}$ alkyl; more preferably. $R_3$ is hydrogen or methyl; further preferably, $R_3$ is hydrogen.

In an embodiment of the present invention, each $R_4$ in the compound shown in general formula (1) is independently hydrogen, fluorine, chlorine, or bromine; preferably, each $R_4$ is independently hydrogen, fluorine, or chlorine; more preferably, $R_4$ is hydrogen.

In an embodiment of the present invention, each $X_1$ in the compound shown in general formula (1) is independently fluorine, chlorine, or bromine; preferably, each $X_1$ is independently fluorine or chlorine.

In an embodiment of the present invention, $X_2$ in the compound shown in general formula (1) is hydrogen, halogen, $C_{1-6}$ alkylamino, di ($C_{1-6}$ alkyl) amino, $C_{3-6}$ cycloalkyl, or 3-7 membered heterocyclic alkyl, which can be optionally substituted by at least one of the following substituents: halogen, $C_{1-6}$ alkyl, $C_{3-6}$ cycloalkyl, and 3-7 membered heterocyclic alkyl; preferably, $X_2$ is hydrogen, halogen, di ($C_{1-6}$ alkyl) amino, or 3-7-membered heterocyclic alkyl, which can be optionally substituted by at least one of the following substituents: halogen, $C_{1-6}$ alkyl, $C_{3-6}$ cycloalkyl, and 3-7-membered heterocyclic alkyl; more preferably, $X_2$ is hydrogen, chlorine, diethylamino, morpholinyl ( 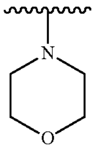 ), 2-oxa-5-azabicyclic [2.2.1] hept-5-yl ( 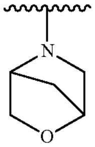 )

or 4-morpholinyl piperidin-1-yl ( 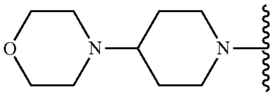 ).

In an embodiment of the present invention, each $X_3$ in the compound shown in general formula (1) is independently hydrogen or fluorine; preferably, $X_3$ is hydrogen.

In a preferred embodiment of the present invention, the
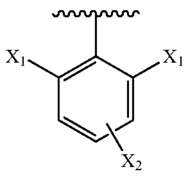
of the compound shown in general formula (1) is selected from the following structural segments:
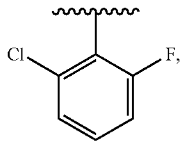
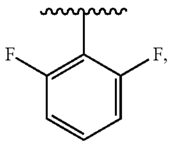
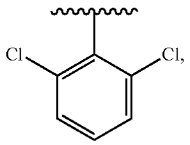
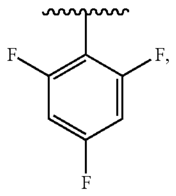
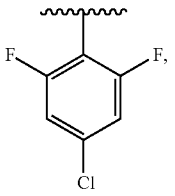
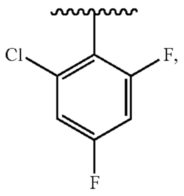
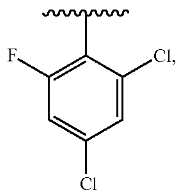
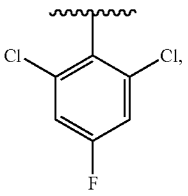
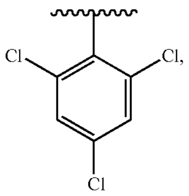
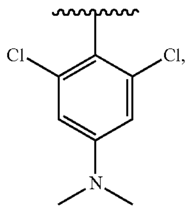
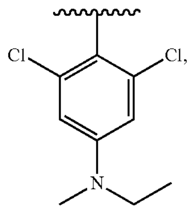
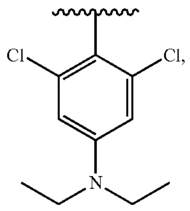
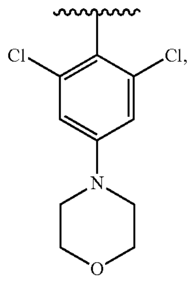
-continued
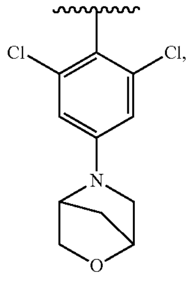
and
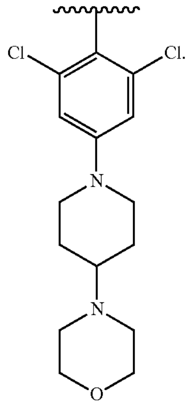
In a more preferred embodiment of the present invention, the
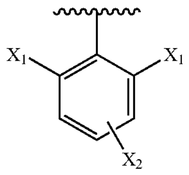
of the compound shown in general formula (1) is selected from the following structural segments:
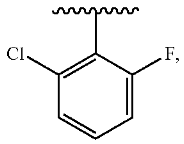
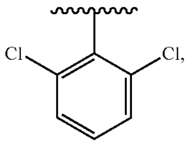
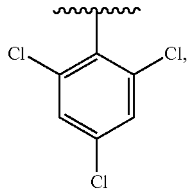
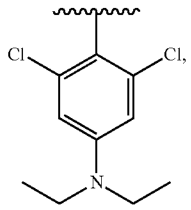
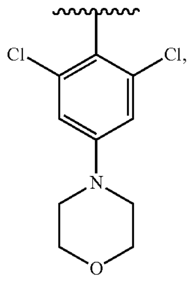

-continued

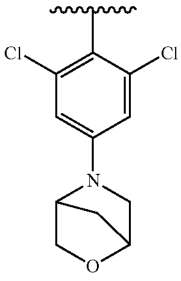

and

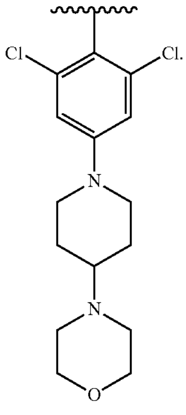

In a further preferred embodiment of the present invention, the

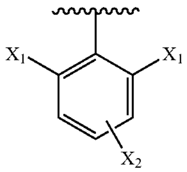

of the compound shown in general formula (1) is selected from the following structural segments:

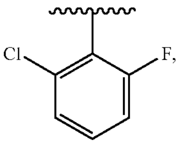

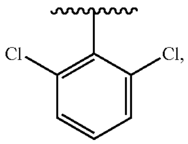

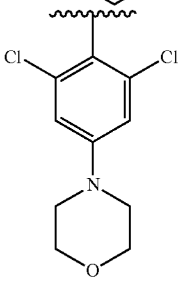

and

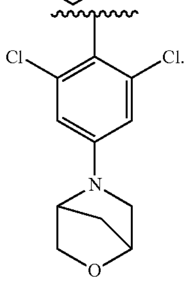

In an embodiment of the present invention. A in the compound shown in general formula (1) is a group shown in general formula (2-1-1) or (2-1-1'), (2-1-1)

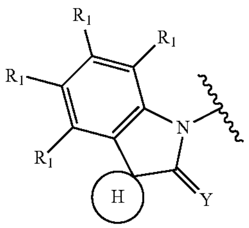

-continued (2-1-1')

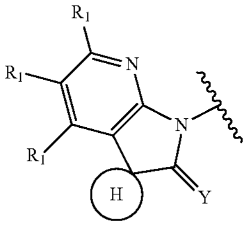

Where,

The ring H is a $C_{3-6}$ cycloalkyl or a 3-7-membered heterocyclic alkyl, and the aforementioned groups can be optionally substituted by at least one of the following substituents: halogen, $C_{1-6}$ alkyl, $C_{3-6}$ cycloalkyl, and 3-7-membered heterocyclic alkyl; preferably, the ring H is a sub-cyclopropyl (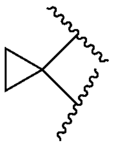)

or a tetrahydro-2H-pyran-4-yl (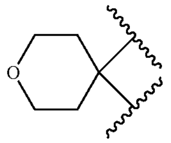);

Y is O or S; preferably, Y is O;

When A is a group as shown in the general formula (2-1-1), two of the four $R_1$ are independently halogen, $C_{1-6}$ alkyl, $C_{1-6}$ alkoxy or di ($C_{1-6}$ alkyl) amino, while the rest are hydrogen; alternatively, one of the four $R_1$ is halogen, $C_{1-6}$ alkyl, $C_{1-6}$ alkoxy, or di ($C_{1-6}$ alkyl) amino, and the rest are hydrogen; alternatively, all the four R1 are hydrogen; preferably, two of the four $R_1$ are independently halogen or di ($C_{1-6}$ alkyl) amino, while the rest are hydrogen; alternatively, one of the four $R_1$ is halogen, $C_{1-6}$ alkoxy or di ($C_{1-6}$ alkyl) amino, and the rest are hydrogen; alternatively, all the four $R_1$ are hydrogen; more preferably, two of the four $R_1$ are independently fluorine, chlorine, or dimethylamino, while the rest are hydrogen; alternatively, one of the four $R_1$ is fluorine, chlorine, methoxy or dimethylamino, and the rest are hydrogen; alternatively, all four $R_1$ are hydrogen;

When A is a group as shown in the general formula (2-1-1'), two of the three $R_1$ are independently halogen, $C_{1-6}$ alkyl, $C_{1-6}$ alkoxy or di ($C_{1-6}$ alkyl) amino, while the rest is hydrogen; alternatively, one of the three $R_1$ is halogen, $C_{1-6}$ alkyl, $C_{1-6}$ alkoxy or di ($C_{1-6}$ alkyl) amino, and the rest are hydrogen; alternatively, all the three $R_1$ are hydrogen; preferably, two of the three $R_1$ are independently halogen or di ($C_{1-6}$ alkyl) amino, while the rest is hydrogen; alternatively, one of the three $R_1$ is halogen, $C_{1-6}$ alkoxy or di ($C_{1-6}$ alkyl)

amino, and the rest are hydrogen; alternatively, all three $R_1$ are hydrogen, more preferably, all the three $R_1$ are hydrogen.

In a preferred embodiment of the present invention, the compound shown in general formula (1) is a compound shown in general formula (2-1-2), (2-1-2)

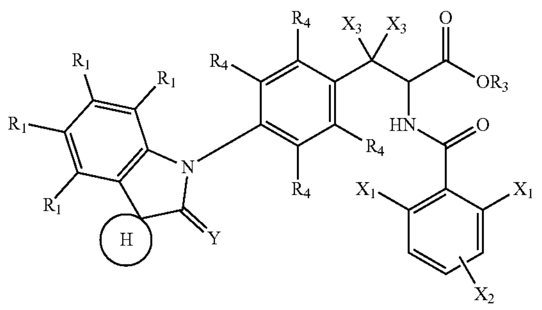

Where, ring H, Y, $R_1$, $R_3$, $R_4$, $X_1$, $X_2$, and $X_3$ are defined as those in the present invention.

In a more preferred embodiment of the present invention, the compound shown in general formula (1) is a compound shown in general formula (2-1-3), (2-1-3)

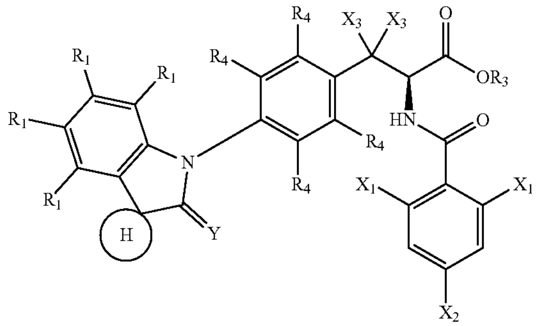

Where, ring H, Y, $R_1$, $R_3$, $R_4$, $X_1$, $X_2$, and $X_3$ are defined as those in the present invention.

In a preferred embodiment of the present invention, the compound shown in general formula (1) is a compound shown in general formula (2-1-2'), (2-1-2')

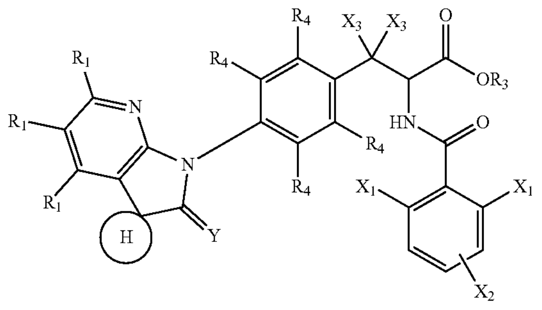

Where, ring H, Y, $R_1$, $R_3$, $R_4$, $X_1$, $X_2$, and $X_3$ are defined as those in the present invention.

In a more preferred embodiment of the present invention, the compound shown in general formula (1) is a compound shown in general formula (2-1-3'), (2-1-3')

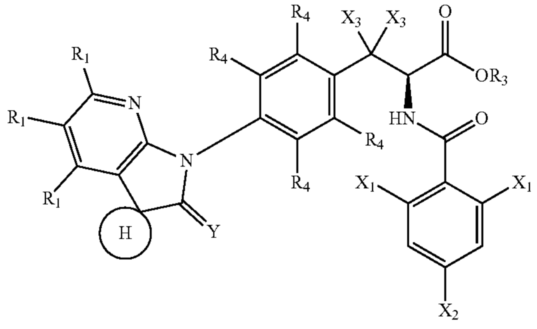

Where, ring H, Y, $R_1$, $R_3$, $R_4$, $X_1$, $X_2$, and $X_3$ are defined as those in the present invention.

In an embodiment of the present invention, A in the compound shown in general formula (1) is a functional group shown in general formula (2-2-1), Y is O or S; preferably, Y is O;

Two of the four $R_1$ are independently halogen, $C_{1-6}$ alkyl, $C_{1-6}$ alkoxy or di ($C_{1-6}$ alkyl) amino, and the rest are hydrogen; alternatively, one of the four R1 is halogen, $C_{1-6}$ alkyl, $C_{1-6}$ alkoxy, or di ($C_{1-6}$ alkyl) amino, and the rest are hydrogen; preferably, two of the four $R_1$ are independently halogen, and the rest are hydrogen; alternatively, one of the four $R_1$ is halogen, $C_{1-6}$ alkoxy or di ($C_{1-6}$ alkyl) amino, and the rest are hydrogen; more preferably, two of the four $R_1$ are independently fluorine or chlorine, and the rest are hydrogen; alternatively, one of the four $R_1$ is fluorine, chlorine, methoxy or dimethylamino, and the rest are hydrogen;

$R_2$ is hydrogen, $C_{1-6}$ alkyl, $C_{1-6}$ haloalkyl, $C_{3-6}$ cycloalkyl, or 3-7-membered heterocyclic alkyl, and the aforementioned groups can be optionally substituted by at least one of the following substituents: halogen, $C_{1-6}$ alkyl, $C_{3-6}$ cycloalkyl, and 3-7-membered heterocyclic alkyl; preferably, $R_2$ is $C_{1-6}$ alkyl, $C_{3-6}$ cycloalkyl, or a 3-7-membered heterocyclic alkyl, and the aforementioned groups can be optionally substituted by the $C_{1-6}$ alkyl; more preferably, $R_2$ is methyl, cyclopropyl, tetrahydro-2H-pyran-4-yl ( 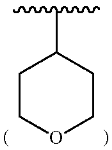 [SMILES: *C1CCOCC1] )

or 1-methylpiperidin-4-yl

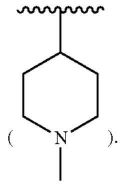

In a preferred embodiment of the present invention, the compound shown in general formula (1) is a compound shown in general formula (2-2-2), (2-2-2)

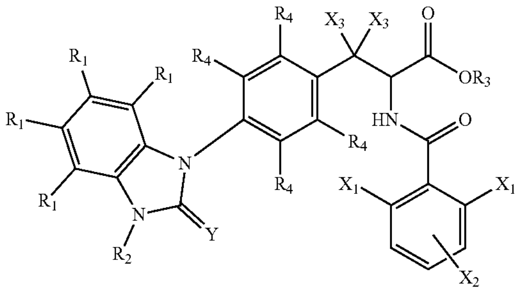

Where, Y, $R_1$, $R_2$, $R_3$, $R_4$, $X_1$, $X_2$, and $X_3$ are defined as those in the present invention.

In a more preferred embodiment of the present invention, the compound shown in general formula (1) is a compound shown in general formula (2-2-3), (2-2-3)

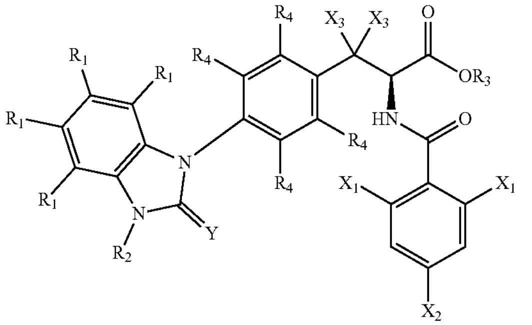

Where, Y, $R_1$, $R_2$, $R_3$, $R_4$, $X_1$, $X_2$, and $X_3$ are defined as those in the present invention.

In an embodiment of the present invention, A in the compound shown in general formula (1) is a functional group shown in general formula (2-3-1), (2-3-1)

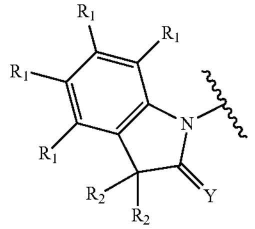

Y is O or S; preferably, Y is O;

One of the four $R_1$ is halogen, $C_{1-6}$ alkyl, $C_{1-6}$ alkoxy or di ($C_{1-6}$ alkyl) amino, and the rest are hydrogen; preferably, one of the four $R_1$ is chlorine, and the rest are hydrogen;

Each $R_2$ is independently hydrogen, $C_{1-6}$ alkyl, $C_{1-6}$ haloalkyl, $C_{3-6}$ cycloalkyl, or 3-7-membered heterocyclic alkyl, which can be optionally substituted by at least one of the following substituents: halogen, $C_{1-6}$ alkyl, $C_{3-6}$ cycloalkyl, and 3-7-membered heterocyclic alkyl; preferably, each $R_2$ is independently $C_{1-6}$ alkyl; more preferably, all $R_2$ are methyl.

In a preferred embodiment of the present invention, the compound shown in general formula (1) is a compound shown in general formula (2-3-2), (2-3-2)

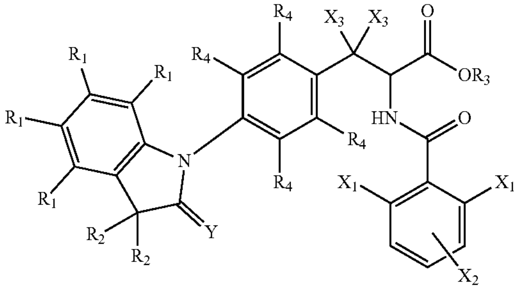

Where, Y, $R_1$, $R_2$, $R_3$, $R_4$, $X_1$, $X_2$, and $X_3$ are defined as those in the present invention.

In a more preferred embodiment of the present invention, the compound shown in general formula (1) is a compound shown in general formula (2-3-3), (2-3-3)

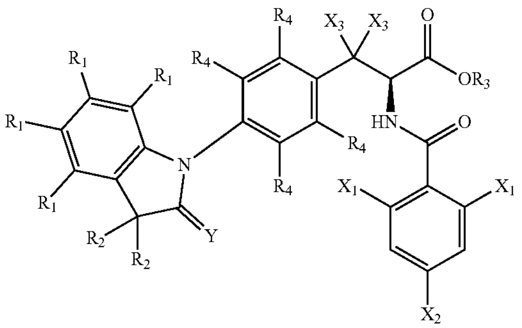

Where, Y, $R_1$, $R_2$, $R_3$, $R_4$, $X_1$, $X_2$, and $X_3$ are defined as those in the present invention.

In a preferred embodiment of the present invention, the
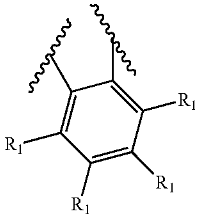
of the compound as shown in general formula (2-1-1), (2-1-2), (2-1-3), (2-2-1), (2-2-2), (2-2-3), (2-3-1), (2-3-2) or (2-3-3) is selected from the following structural segments:
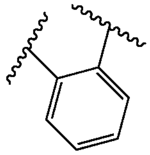, 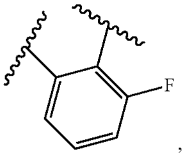, 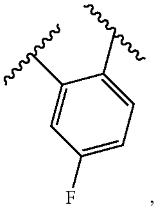,
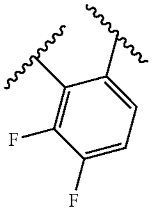, 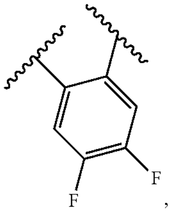, 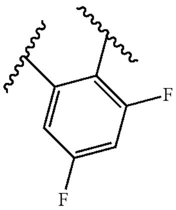,
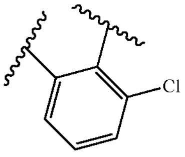, 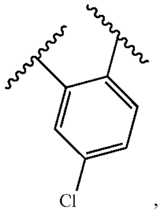, 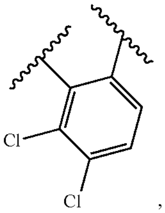,
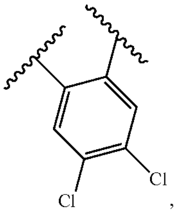, 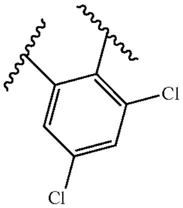, 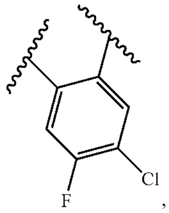,
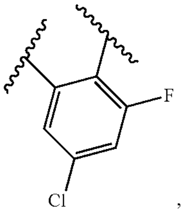, 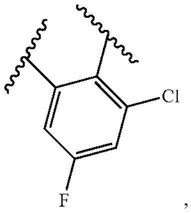,
-continued
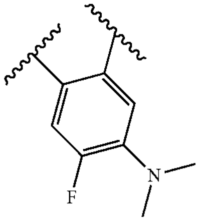, 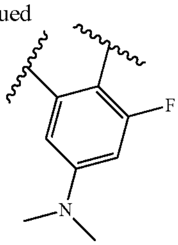,
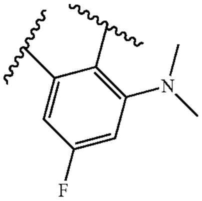, 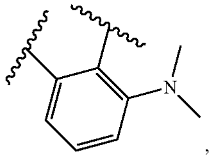,
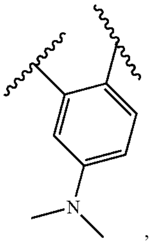, 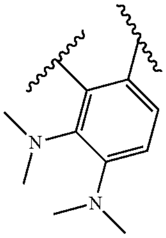, 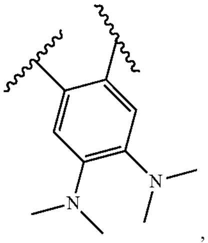,
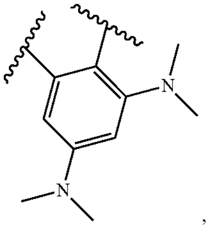, 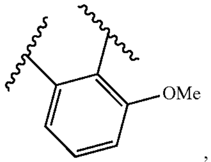,
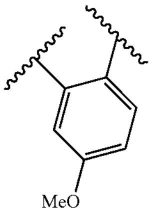, 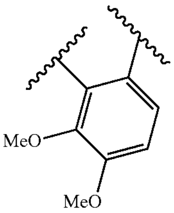,
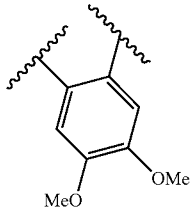 and 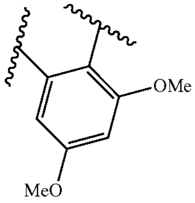.
In a more preferred embodiment of the present invention, the
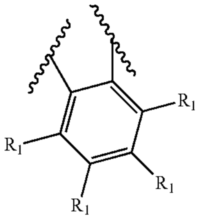

of the compound as shown in general formula (2-1-1), (2-1-2), (2-1-3), (2-2-1), (2-2-2), (2-2-3), (2-3-1), (2-3-2) or (2-3-3) are selected from the following structural segments:

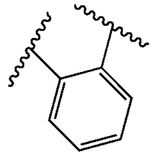 , 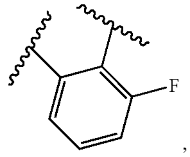 , 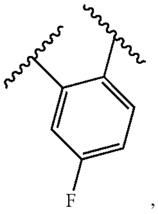 ,

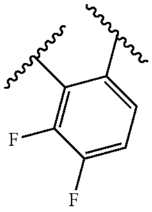 , 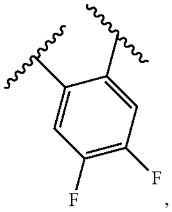 , 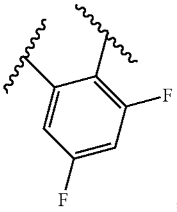 ,

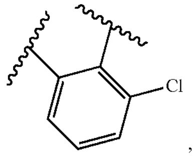 , 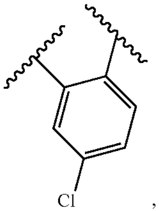 , 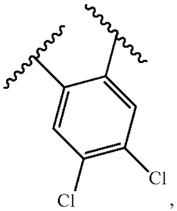 ,

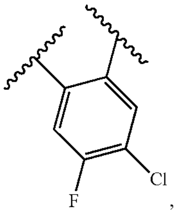 , 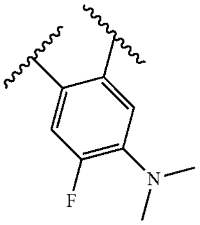 ,

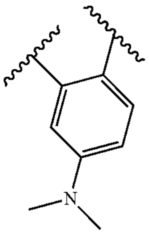 and 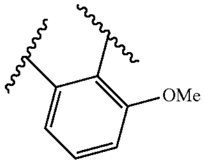 .

In a further preferred embodiment of the present invention, the

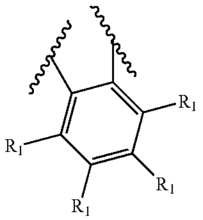

of the compound as shown in general formula (2-1-1), (2-1-2), (2-1-3), (2-2-1), (2-2-2), (2-2-3), (2-3-1), (2-3-2) or (2-3-3) are selected from the following structural segments:

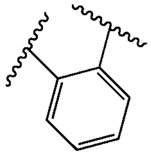 , 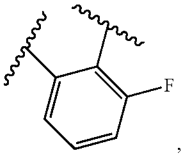 , 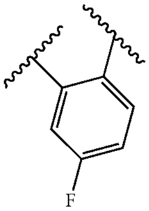 ,

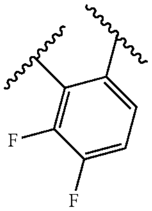 , 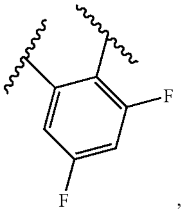 , 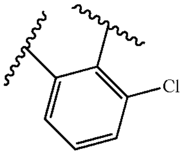 ,

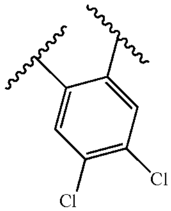 , 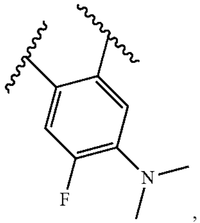 ,

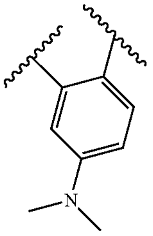 and 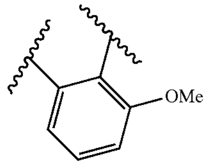 .

In a preferred embodiment of the present invention, the

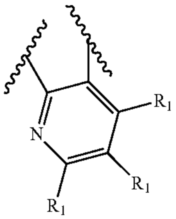

of the compound as shown in general formula (2-1-1'), (2-1-2'), or (2-1-3') is

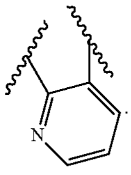 .

The present invention also provides the following compounds or pharmaceutically acceptable salts, esters, solvates, optical isomers, tautomers, isotope markers, or prodrugs thereof,

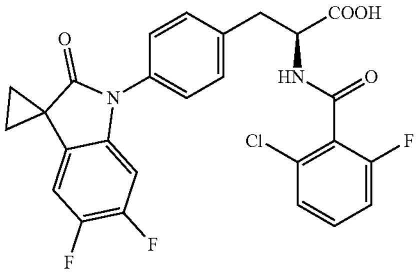
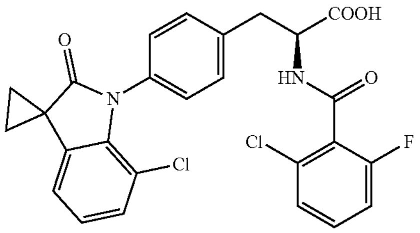
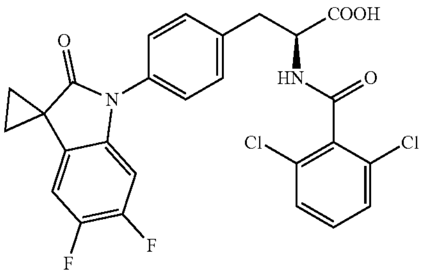
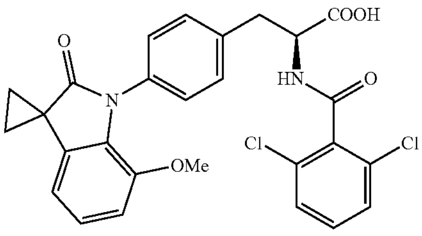
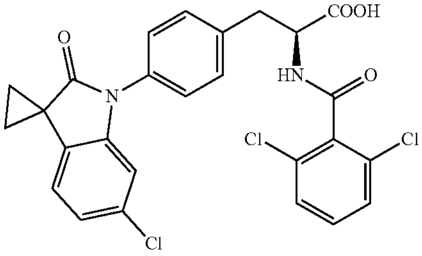
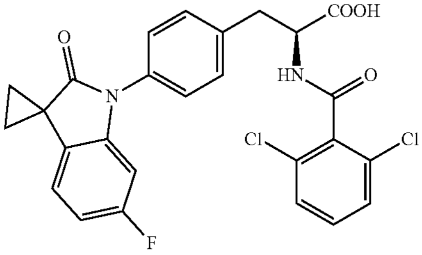
-continued
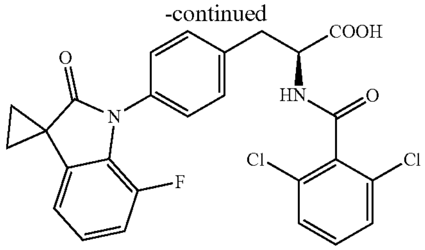
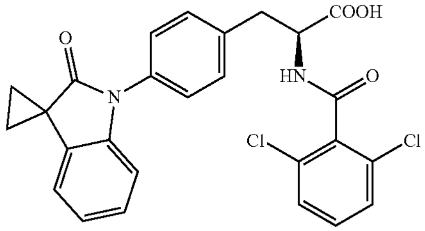
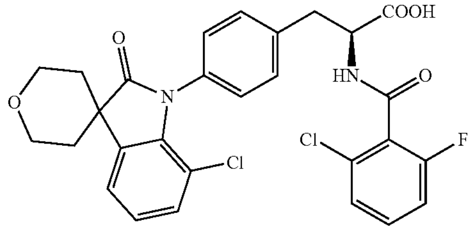
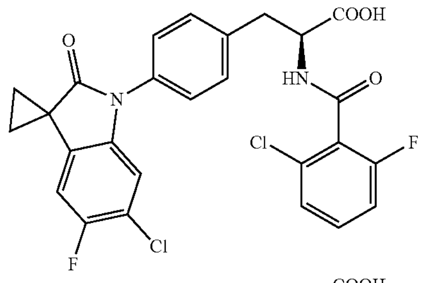
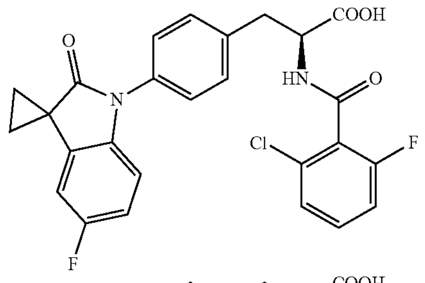
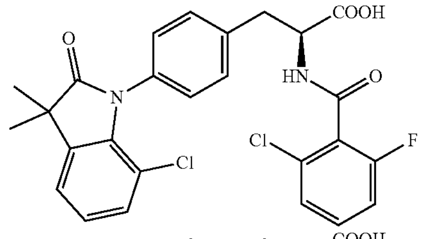
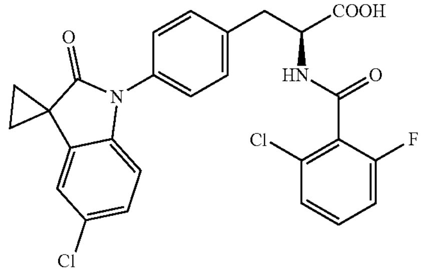

-continued
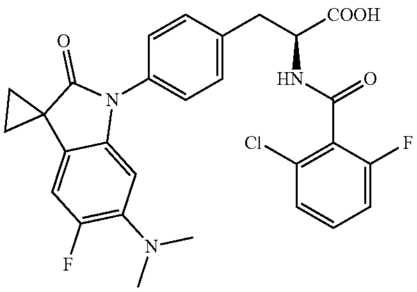
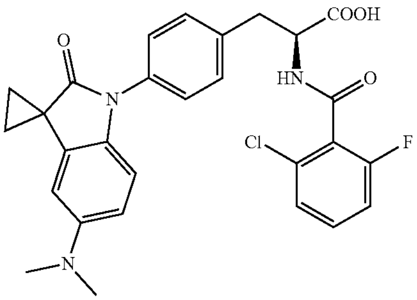
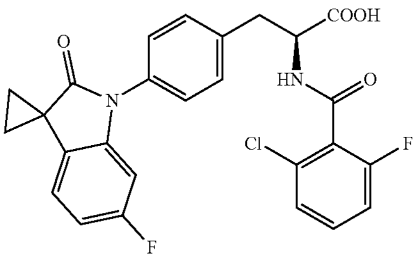
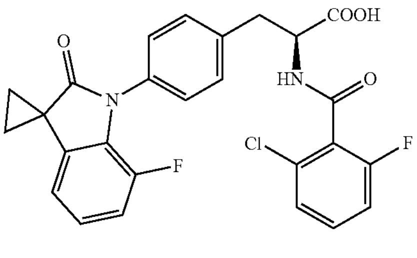
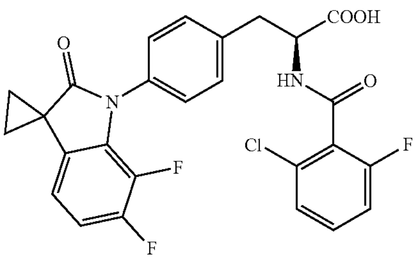
-continued
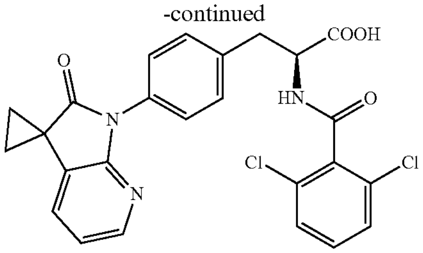
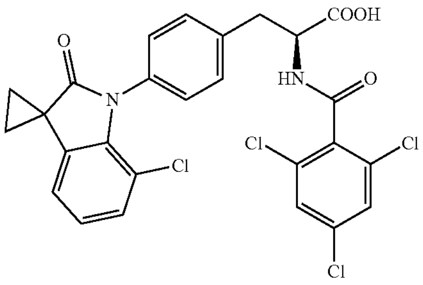
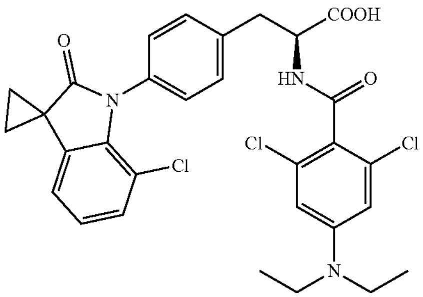
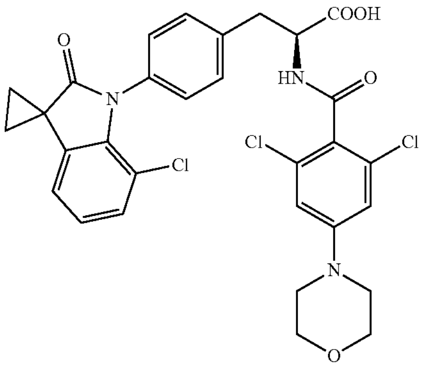
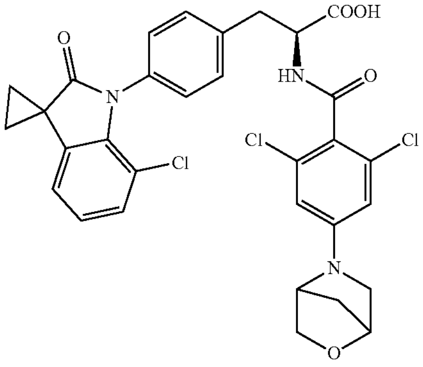

-continued
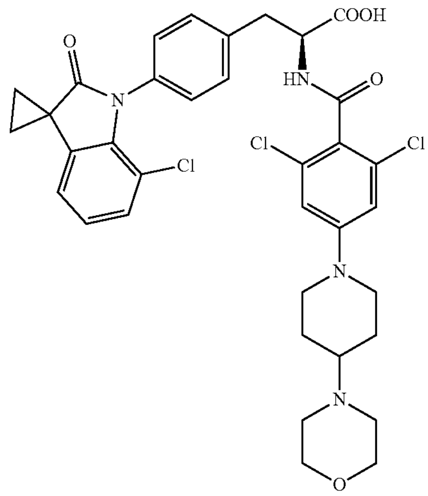
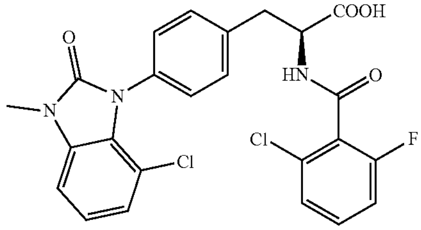
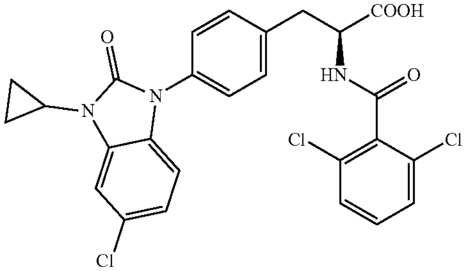
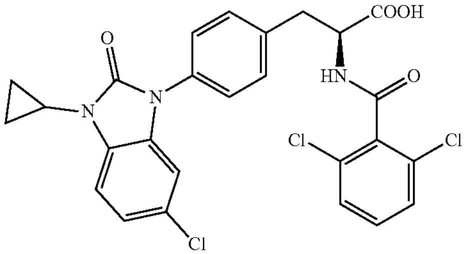
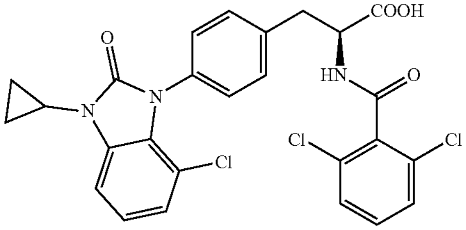
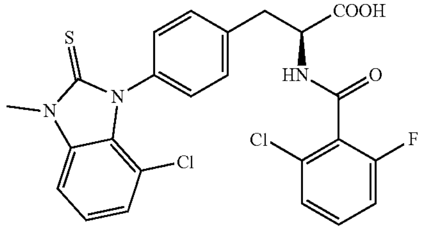
-continued
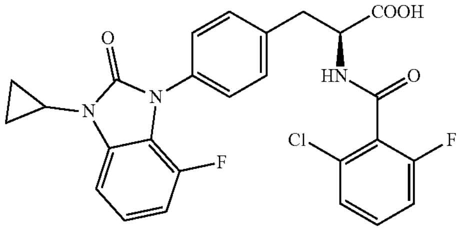
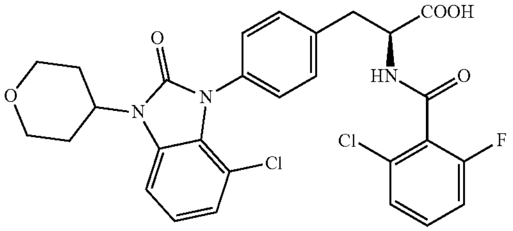
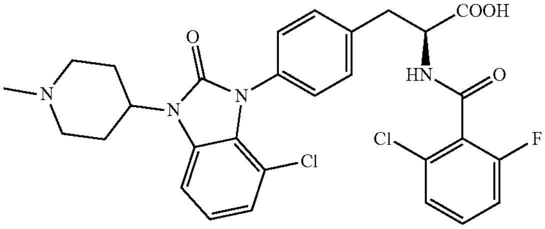
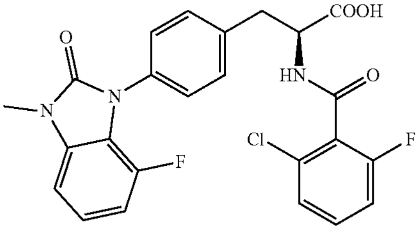
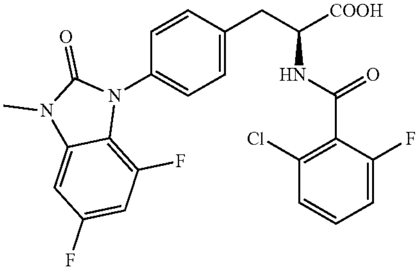
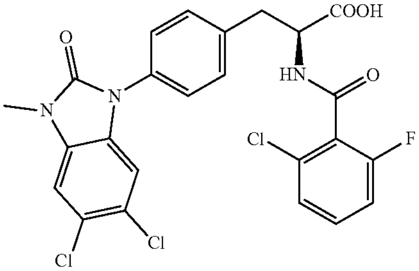
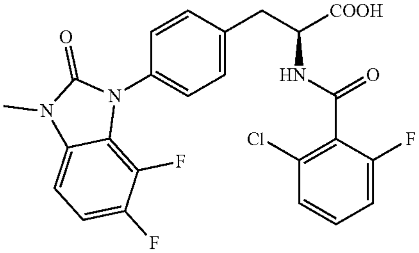

-continued
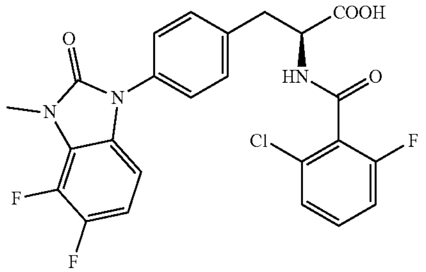
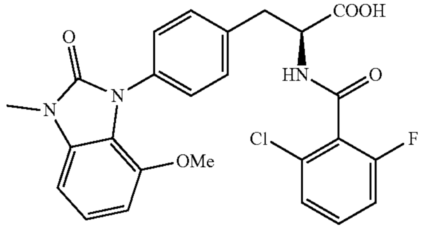
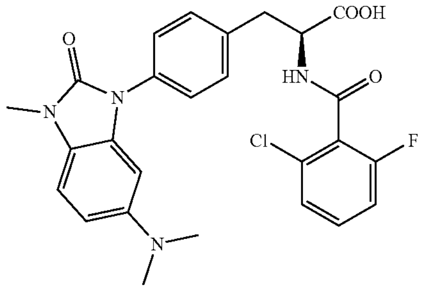
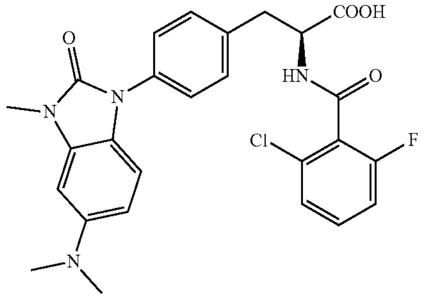
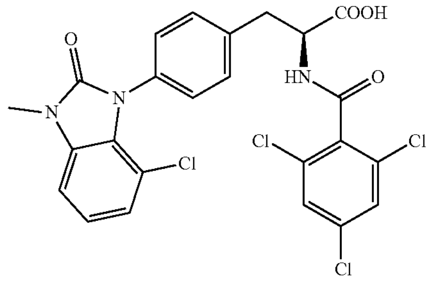
-continued
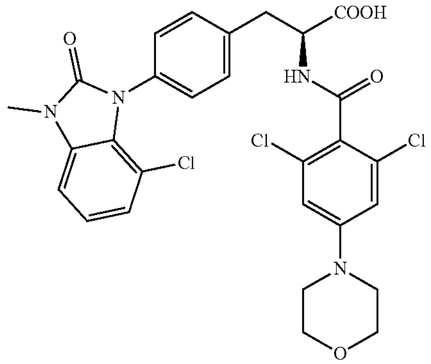
Preparation Method of General Formula Compound
The compound shown in general formula (1) of the present invention (such as having a carboxyl at the end, i.e. $R_3$ is hydrogen) can be prepared by the following method.
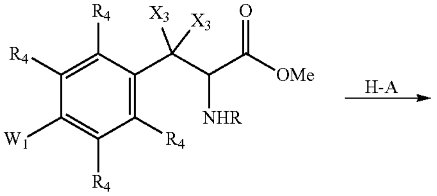
$W_1$ = Br, I
P1
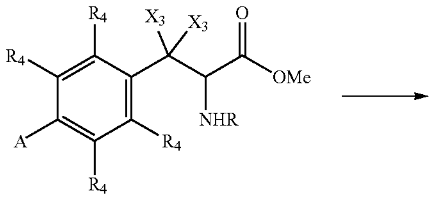
M1
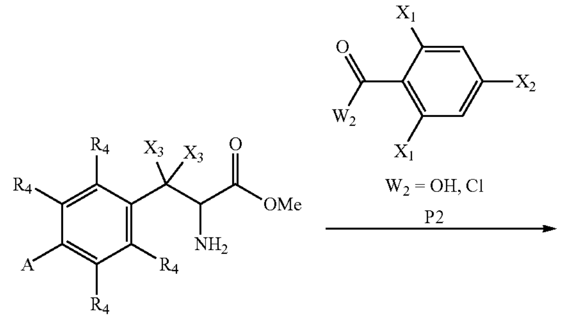
M2

-continued

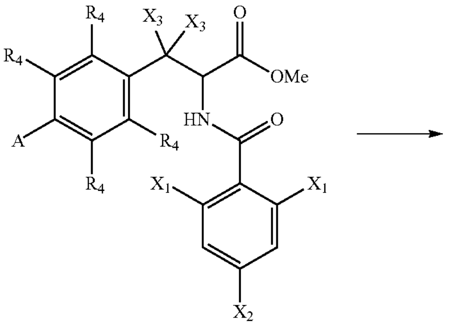

M3

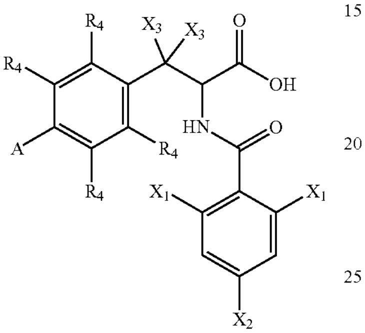

Where, $R_4$, $X_1$, $X_2$, $X_3$, and A are defined as those in general formula (1); $W_1$ is bromine or iodine, $W_2$ is hydroxyl or chlorine, and R is an amino protecting group.

First, intermediate P1 and intermediate H-A undergo coupling reaction to obtain intermediate M1; preferably, the coupling reaction is carried out in the presence of metal catalysts (such as cuprous iodide, etc.), ligands (such as N, N-dimethylglycine or its hydrochloride, etc.), bases (such as cesium carbonate, etc.) and organic solvents (such as acetonitrile, 1,4-dioxane, etc.) that may not have adverse effects on the reaction.

Secondly, intermediate M1 undergoes deprotection reaction to obtain intermediate M2; preferably, the deprotection reaction is carried out in the presence of acids (such as trifluoroacetic acid, etc.) and organic solvents (such as dichloromethane) that may not have adverse effects on the reaction.

Furthermore, intermediate M2 and intermediate P2 undergo condensation reaction to obtain intermediate M3; preferably, the condensation reaction is carried out in the presence of bases (such as N, N-diisopropylethylamine, triethylamine, etc.) and organic solvents (such as dichloromethane) that may not have an adverse effect on the reaction.

Finally, the intermediate M3 is hydrolyzed to obtain the target product; preferably, the hydrolysis reaction is carried out in the presence of bases (such as sodium hydroxide, etc.) and mixed solvents (such as tetrahydrofuran/water, etc.) that may not have adverse effects on the reaction.

The compound shown in general formula (1) of the present invention (for example, having an ester group at the end, i.e. $R_3$ is as defined in general formula (1), but is not hydrogen) can be prepared by the following method.

Option 1:

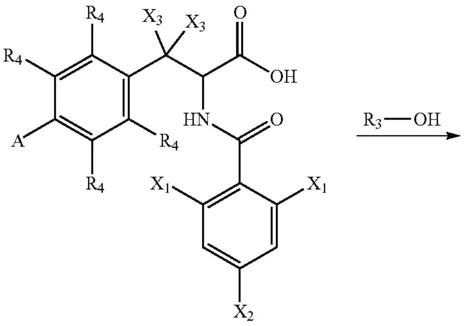

M4

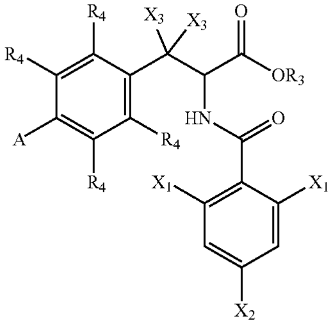

Where, $R_4$, $X_1$, $X_2$, $X_3$, and A are defined as those in general formula (1).

According to the preparation method of compounds with carboxyl (i.e. $R_3$ is hydrogen) at the end, the intermediate M4 is obtained, and then the target product is obtained through esterification reaction with R3-OH; preferably, the esterification reaction is carried out in the presence of condensation aids (such as 1-hydroxybenzotriazole (HOBt), 1,3-dicyclohexylcarbodiimide (DCC), and O-(7-azabenzotriazol-1-yl)-N,N,N',N'-tetramethylurea hexafluorophosphate (HATU), etc.), bases (such as N,N-diisopropylethylamine, triethylamine, and pyridine, etc.), and organic solvents (such as dichloromethane, tetrahydrofuran, and acetonitrile, etc.) that may not have adverse effects on the reaction.

Option 2:

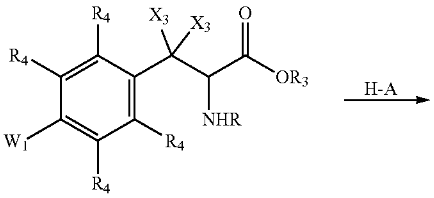

$W_1$ = Br, I

P3

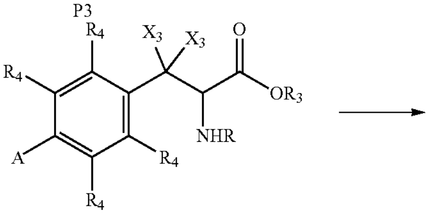

M5

-continued

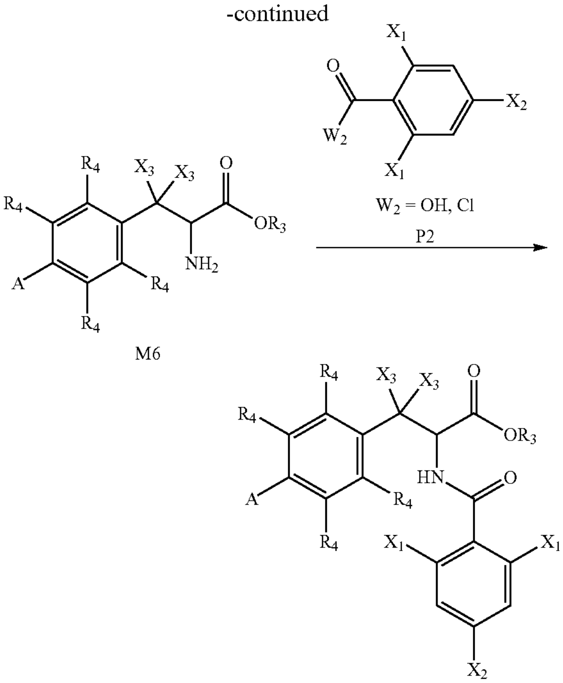

M6

Where, $R_4$, $X_1$, $X_2$, $X_3$, and A are defined as those in general equation (1); W1 is bromine or iodine, and W2 is hydroxyl or chlorine.

First, intermediate P3 and intermediate H-A undergo coupling reaction to obtain intermediate M5; preferably, the coupling reaction is carried out in the presence of metal catalysts (such as cuprous iodide, etc.), ligands (such as N, N-dimethylglycine or its hydrochloride, etc.), bases (such as cesium carbonate, etc.) and organic solvents (such as acetonitrile, 1,4-dioxane, etc.) that may not have adverse effects on the reaction.

Secondly, the intermediate M5 undergoes deprotection reaction to obtain the intermediate M6; preferably, the deprotection reaction is carried out in the presence of acids (such as trifluoroacetic acid, etc.) and organic solvents (such as dichloromethane, etc.) that may not have adverse effects on the reaction.

Furthermore, intermediate M6 and intermediate P2 undergo condensation reaction to obtain the target product preferably, the condensation reaction is carried out in the presence of bases (such as N,N-diisopropylethylamine, triethylamine, etc.) and organic solvents (such as dichloromethane) that may not have adverse effects on the reaction.

Pharmaceutical Composition

The present invention provides a pharmaceutical composition comprising the compound of the present invention or pharmaceutically acceptable salts, esters, solvates, optical isomers, tautomers, isotope markers or prodrugs thereof.

In an embodiment of the present invention, the pharmaceutical composition comprises not only the compound of the present invention as the active ingredient of the drug or its pharmaceutically acceptable salts, esters, solvates, optical isomers tautomers, isotope markers or prodrugs, but also at least one pharmaceutically acceptable excipient, including (but not limited to) the following components: diluent, adhesive, lubricant, flow aid, surfactant, flavoring, smelling agent, pH regulators, aromatic, and sweetener, etc.

In an embodiment of the present invention, the compound of the present invention as the active ingredient of the drug or its pharmaceutically acceptable salts, esters, solvates, optical isomers, tautomers, isotope markers or prodrugs, but also at least one other pharmaceutical active ingredient that can enhance and/or reduce toxicity after combination.

In an embodiment of the present invention, the pharmaceutical composition exists in a specific form, including (but not limited to) the following dosage forms: tablet capsule lozenge, hard candy, powder, spray, cream, ointment, suppository, gel, paste, lotion, ointment, aqueous suspension, injectable solution, elixir, and syrup, etc.

In an embodiment of the present invention, a pharmaceutical composition of a unit of measurement or unit of drug comprising 0.01-1000 mg of the compound as shown in general formula (1) or equivalent pharmaceutically acceptable salts, esters, solvates, optical isomers, tautomers, isotope markers, or prodrugs.

Medical Uses Related to α4β7 Integrin

Pharmacological experiments have shown that the compound of the present invention has certain inhibitory activity for α4β7 integrin and can therefore be used for prevention and/or treatment at least partially by α4β7 integrin mediated diseases and/or symptoms. The present invention also provides the uses of the compound of the present invention or pharmaceutically acceptable salts, esters, solvates, optical isomers, tautomers, isotope markers or prodrugs thereof, or pharmaceutical compositions of the present invention, in the production of drugs for prevention and/or treatment at least partially by α4β7 integrin mediated diseases aid/or symptoms.

In addition, the present invention also provides a method for preventing and/or treating at least partially by α4β7 integrin mediated diseases and/or symptoms, which includes the following steps: administrating the aforementioned compounds or their pharmaceutically acceptable salts, esters, solvates, optical isomers, tautomers, isotope markers or prodrugs thereof, or the aforementioned drug compositions thereof, to individuals in need.

In an embodiment of the present invention, at least partially by α4β7 integrin mediated diseases and/or symptoms include (but are not limited to) autoimmune diseases, inflammatory diseases, and tumor cell proliferation and metastasis.

In an embodiment of the present invention, autoimmune diseases include (but are not limited to) rheumatoid arthritis (RA), systemic lupus erythematosus (SLE), and multiple sclerosis (MS).

In an embodiment of the present invention, inflammatory diseases include (but are not limited to) inflammatory bowel disease (IBD); preferably, inflammatory bowel diseases include (but are not limited to) ulcerative colitis (UC) and Krohn's disease (CD).

The present invention will be elaborated in detail through embodiments. These embodiments are only preferred embodiments of the present invention and should not be regarded as limitations on the invention. Further, unless otherwise indicated, the instruments, drugs, reagents, consumables, etc. used in the following embodiments may be obtained by conventional commercial means.

It should be noted that intermediate preparation example 1 shows an example of synthesis of intermediate P-1 as shown in general formula P1, intermediate preparation examples 2 to 33 show an example of synthesis of intermediate P-2 to P-33 as shown in general formula H-A, intermediate preparation examples 34 to 38 show an example of synthesis of intermediate P-34 to P-38 as shown in general formula P2, and examples 1 to 39 show an example of synthesis of compounds of the present invention.

Intermediate Preparation Example 1: Synthesis of 3-(4-iodophenyl)-2-(triphenylamino) methyl propionate (P-1)

(Step 1) (S)-2-amino-3-(4-iodophenyl) methyl propionate

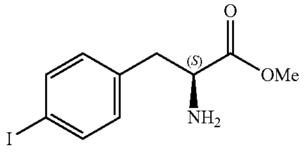

Dissolve 4-iodo-L-phenylalanine (29.1 g, 10 mmol) in anhydrous methanol (290 mL) and cool in an ice bath. Add thionyl chloride (17.9 g, 15 mmol) and N,N-Dimethylformamide (2.9 mL), react at 40° C. for 24 h. Concentrate the reaction solution with vacuum, a white solid is obtained, which is the title compound (29 g, 95%). ESI-QQQ-MS: m/z 306 $[M+H]^+$.

(Step 2) 3-(4-iodophenyl)-2-(triphenylamino) methyl propionate (P-1)

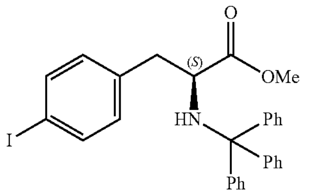

Dissolve (S)-2-amino-3-(4-iodophenyl) methyl propionate (24.4 g, 8 mmol) in dichloromethane (480 mL) and cool in an ice bath. Add triethylamine (12.1 g, 12 mmol) and 1.2 eq triphenylmethyl chloride (26.8 g, 9.6 mmol), react at room temperature for 8 h. After concentrating the reaction solution with vacuum, purify the concentrate with silica gel column chromatography (petroleum ether/ethyl acetate=10:1) to obtain the title compound (30.7 g, 70%). ESI-QQQ-MS: m/z 548 $[M+H]^+$.

Intermediate Preparation Example 2: Synthesis of spiro[cyclopropane-1,3'-indoline]-2'-one (P-2)

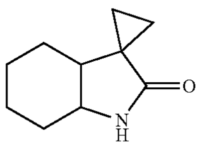 [SMILES: O=C1NC2CCCCC2C12CC2]

Dissolve indoline-2-ketone (0.27 g, 2 mmol) in anhydrous tetrahydrofuran (3 mL), cool to −40° C. add LDA (2 mol/L, 0.4 mL, 8 mmol), stir for 30 min, heat to 0° C., add 1,2-dibromoethane (1.14 g, 6 mmol), and react at room temperature for 24 h. Add saturated ammonium chloride solution (5 mL) and water (15 mL) to the reaction system, extract with ethyl acetate twice (10 mL each time), combine organic phase, wash with saturated salt solution once, dry with anhydrous sodium sulfate, filter and concentrate with vacuum, and purify the concentrate by silica gel column chromatography (petroleum ether/ethyl acetate=4:1) to obtain the title compound (0.19 g, 60%). ESI-QQQ-MS: m/z 160 $[M+H]^+$.

Intermediate Preparation Example 3: Synthesis of 7'-fluorospiro[cyclopropane-1,3'-indoline]-2'-one (P-3)

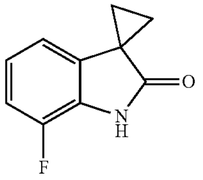 [SMILES: O=C1Nc2c(F)cccc2C12CC2]

Dissolve 7-fluoroindolin-2-one (0.3 g, 2 mmol) in anhydrous tetrahydrofuran (3 mL), cool to −40° C. add LDA (2 mol/L, 4 mL, 8 mmol), stir for 30 min, heat to 0° C., add 1,2-dibromoethane (1.14 g, 6 mmol), and react at room temperature for 24 h. Add saturated ammonium chloride solution (5 mL) and water (15 mL) to the reaction system, extract with ethyl acetate twice (10 mL each time), combine organic phase, wash with saturated salt solution once, dry with anhydrous sodium sulfate, filter and concentrate with vacuum, and purify the concentrate by silica gel column chromatography (petroleum ether/ethyl acetate=4:1) to obtain the title compound (0.19 g, 54%). ESI-QQQ-MS: m/z 178 $[M+H]^+$.

Intermediate Preparation Example 4: Synthesis of 6'-fluorospiro[cyclopropane-1,3'-indoline]-2'-one (P-4)

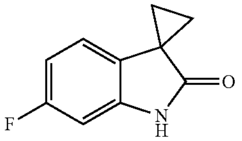 [SMILES: O=C1Nc2cc(F)ccc2C12CC2]

Dissolve 6-fluoroindolin-2-one (0.3 g, 2 mmol) in anhydrous tetrahydrofuran (3 mL), cool to −40° C. add LDA (2 mol/L, 4 mL, 8 mmol), stir for 30 min, heat to 0° C., add 1,2-dibromoethane (1.14 g, 6 mmol), and react at room temperature for 24 h. Add saturated ammonium chloride solution (5 mL) and water (15 mL) to the reaction system, extract with ethyl acetate twice (10 mL each time), combine organic phase, wash with saturated salt solution once, dry with anhydrous sodium sulfate, filter and concentrate with vacuum, and purify the concentrate by silica gel column chromatography (petroleum ether/ethyl acetate=4:1) to obtain the title compound (0.22 g, 62%). ESI-QQQ-MS: m/z 178 $[M+H]^+$.

Intermediate Preparation Example 5: Synthesis of 5'-fluorospiro[cyclopropane-1,3'-indoline]-2'-one (P-5)

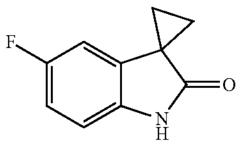 [SMILES: O=C1Nc2ccc(F)cc2C12CC2]

Dissolve 5-fluoroindolin-2-one (0.3 g, 2 mmol) in anhydrous tetrahydrofuran (3 mL), cool to −40° C., add LDA (2 mol/L, 4 mL, 8 mmol), stir for 30 min, heat to 0° C. add 1,2-dibromoethane (1.14 g, 6 mmol), and react at room temperature for 241. Add saturated ammonium chloride solution (5 mL) and water (15 mL) to the reaction system, extract with ethyl acetate twice (10 mL each time), combine organic phase, wash with saturated salt solution once, dry with anhydrous sodium sulfate, filter and concentrate with vacuum, and purify the concentrate by silica gel column chromatography (petroleum ether/ethyl acetate=4:1) to obtain the title compound (022 g, 61%). ESI-QQQ-MS: m/z 178 $[M+H]^+$.

Intermediate Preparation Example 6: Synthesis of 7'-chlorospiro[cyclopropane-1,3'-indoline]-2'-one (P-6)

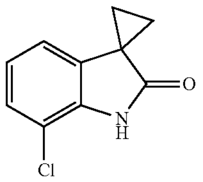 [SMILES: O=C1Nc2c(Cl)cccc2C12CC2]

Dissolve 7-chloroindoline-2-one (0.33 g, 2 mmol) in anhydrous tetrahydrofuran (3 mL), cool to 40° C. add LDA (2 mol/L, 4 mL, 8 mmol), stir for 30 min, heat to 0° C., add 1,2-dibromoethane (1.14 g, 6 mmol), and react at room temperature for 24 h. Add saturated ammonium chloride solution (5 mL) and water (15 mL) to the reaction system, extract with ethyl acetate twice (10 mL each time), combine organic phase, wash with saturated salt solution once, dry with anhydrous sodium sulfate, filter and concentrate with vacuum, and purify the concentrate by silica gel column chromatography (petroleum ether/ethyl acetate=4:1) to obtain the title compound (0.2 g, 52%). ESI-QQQ-MS: m/z 194 $[M+H]^+$.

Intermediate Preparation Example 7: Synthesis of 6'-chlorospiro[cyclopropane-1,3'-indoline]-2'-one (P-7)

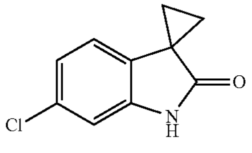 [SMILES: O=C1Nc2cc(Cl)ccc2C12CC2]

Dissolve 6-chloroindoline-2-one (0.33 g, 2 mmol) in anhydrous tetrahydrofuran (3 mL), cool to −40° C., add LDA (2 mol/L, 4 mL, 8 mmol), stir for 30 min, heat to 0° C. add 1,2-dibromoethane (1.14 g, 6 mmol), and react at room temperature for 24 h. Add saturated ammonium chloride solution (5 mL) and water (15 mL) to the reaction system, extract with ethyl acetate twice (10 mL each time), combine organic phase, wash with saturated salt solution once, dry with anhydrous sodium sulfate, filter and concentrate with vacuum, and purify the concentrate by silica gel column chromatography (petroleum ether/ethyl acetate=4:1) to obtain the title compound (0.21 g, 54%). ESI-QQQ-MS: m/z 194 $[M+H]^+$.

Intermediate Preparation Example 8: Synthesis of 5'-chlorospiro[cyclopropane-1,3'-indoline]-2'-one (P-8)

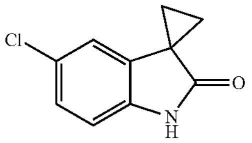 [SMILES: O=C1Nc2ccc(Cl)cc2C12CC2]

Dissolve 5-chloroindoline-2-one (0.33 g, 2 mmol) in anhydrous tetrahydrofuran (3 mL), cool to −40° C., add LDA (2 mol/L, 4 mL, 8 mmol), stir for 30 min, heat to 0° C. add 1,2-dibromoethane (1.14 g, 6 mmol), and react at room temperature for 24 h. Add saturated ammonium chloride solution (5 mL) and water (15 mL) to the reaction system, extract with ethyl acetate twice (10 mL each time), combine organic phase, wash with saturated salt solution once, dry with anhydrous sodium sulfate, filter and concentrate with vacuum, and purify the concentrate by silica gel column chromatography (petroleum ether/ethyl acetate=4:1) to obtain the title compound (0.19 g, 50%). ESI-QQQ-MS: m/z 194 $[M+H]^+$.

Intermediate Preparation Example 9: Synthesis of 7-methoxyspiro[cyclopropane-1,3'-indoline]-2'-one (P-9)

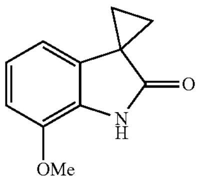 [SMILES: COc1cccc2c1NC(=O)C21CC1]

Dissolve 7-methoxyspiro-2-one (0.33 g, 2 mmol) in anhydrous tetrahydrofuran (3 mL), cool to −40° C., add LDA (2 mol/L, 4 mL, 8 mmol), stir for 30 min, heat to 0° C. add 1,2-dibromoethane (1.14 g, 6 mmol), and react at room temperature for 24 h. Add saturated ammonium chloride solution (5 mL) and water (15 mL) to the reaction system, extract with ethyl acetate twice (10 mL each time), combine organic phase, wash with saturated salt solution once, dry with anhydrous sodium sulfate, filter and concentrate with vacuum, and purify the concentrate by silica gel column chromatography (petroleum ether/ethyl acetate=4:1) to obtain the title compound (0.2 g, 53%). ESI-QQQ-MS: m/z 190 $[M+H]^+$.

Intermediate Preparation Example 10: Synthesis of 5',6'-difluorospiro[cyclopropane-1,3'-indoline]-2'-one (P-10)

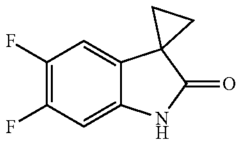 [SMILES: O=C1Nc2cc(F)c(F)cc2C12CC2]

Dissolve 5,6-difluorospiro-2-one (0.34 g, 2 mmol) in anhydrous tetrahydrofuran (3 mL), cool to −40° C., add LDA (2 mol/L, 4 mL, 8 mmol), stir for 30 min, heat to 0° C. add 1,2-dibromoethane (1.14 g, 6 mmol), and react at room temperature for 24 h. Add saturated ammonium chloride solution (5 mL) and water (15 mL) to the reaction system, extract with ethyl acetate twice (10 mL each time), combine organic phase, wash with saturated salt solution once, dry with anhydrous sodium sulfate, filter and concentrate with vacuum, and purify the concentrate by silica gel column chromatography (petroleum ether/ethyl acetate=4:1) to obtain the title compound (0.22 g, 57%). ESI-QQQ-MS: m/z 196 $[M+H]^+$.

Intermediate Preparation Example 11: Synthesis of 6'-chloro-5'-fluorospiro[cyclopropane-1,3'-indoline]-2'-one (P-11)

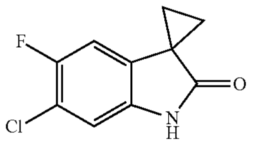 [SMILES: O=C1Nc2cc(Cl)c(F)cc2C12CC2]

Dissolve 6-chloro-5-fluoroindolin-2-one (0.37 g, 2 mmol) in anhydrous tetrahydrofuran (3 mL), cool to −40° C., add LDA (2 mol/L, 4 mL, 8 mmol), stir for 30 min, heat to 0° C. add 1,2-dibromoethane (1.14 g, 6 mmol), and react at room temperature for 24 h. Add saturated ammonium chloride solution (5 mL) and water (15 mL) to the reaction system, extract with ethyl acetate twice (10 mL each time), combine organic phase, wash with saturated salt solution once, dry with anhydrous sodium sulfate, filter and concentrate with vacuum, and purify the concentrate by silica gel column chromatography (petroleum ether/ethyl acetate=4:1) to obtain the title compound (0.21 g, 50%). ESI-QQQ-MS: m/z 212 $[M+H]^+$.

Intermediate Preparation Example 12: Synthesis of 6',7'-difluorospiro[cyclopropane-1,3'-indoline]-2'-one (P-12)

(Step 1) (E)-N-(2,3-difluorophenyl)-2-(hydroxyimino)acetamide

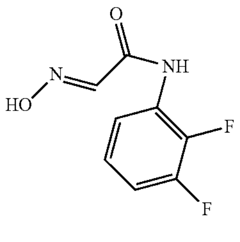 [SMILES: O=C(/C=N/O)Nc1cccc(F)c1F]

Add hydrochloric acid solution (0.6 mL) of 2,3-difluoroaniline (0.78 g, 6 mmol) to a mixed system of chloral hydrate (1.4 g, 8.4 mmol), sodium sulfate (4.74 g, 33.4 mmol) and water (6 mL), react at room temperature for 1 h, then add hydroxylamine hydrochloride (0.58 g, 8.4 mmol), heat to 60° C., and react for 2 h. Cool and filter the reaction solution, the filter cake is the title compound (crude product, 0.7 g), which is directly used for the next reaction. ESI-QQQ-MS: m/z 201 $[M+H]^+$.

(Step 2) 6,7-difluoroindoline-2,3-dione

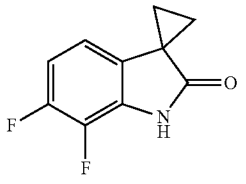 [SMILES: O=C1Nc2c(ccc(F)c2F)C12CC2]

Add (E)-N-(2,3-difluorophenyl)-2-(hydroxyimino) acetamide (0.7 g, 3.5 mmol) to sulfuric acid (2.5 mL), heat to 80° C. and react for 3 h. After cooling the reaction system, pour ice water (20 mL), filter out the precipitate, and dry with vacuum to obtain the title compound (crude product, 0.35 g). ESI-QQQ-MS: m/z 184 $[M+H]^+$.

(Step 3) 6,7-difluoroindolin-2-one

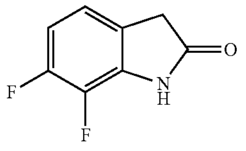 [SMILES: O=C1Cc2ccc(F)c(F)c2N1]

Dissolve 6,7-difluoroindoline-2,3-dione (0.35 g, 1.9 mmol) in ethylene glycol (2 mL), add hydrazine hydrate (0.18 mL, 3.8 mmol), heat to 130° C. react for 4 h, then cool to 25° C., react for 16 h, add water (2 mL) and concentrated hydrochloric acid (0.2 mL), continue to heat to 45° C., react for 1 h. Cool the reaction system in an ice bath, filter out the precipitate, wash with water for 3 times, and dry with vacuum at 90° C. to obtain the title compound (0.26 g, 70%). ESI-QQQ-MS: m/z 170 $[M+H]^+$.

(Step 4) 6',7'-difluoro[cyclopropane-1,3'-dihydroindole]-2'-one (P-12)

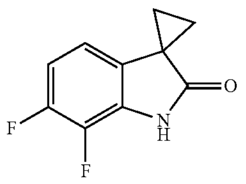 [SMILES: O=C1Nc2c(ccc(F)c2F)C12CC2]

Dissolve 6,7-difluoroindoline-2-one (0.26 g, 1.54 mmol) in anhydrous tetrahydrofuran (3 mL), cool to −40° C., add LDA (2 mol/L, 3 mL, 6 mmol), stir for 30 min, heat to 0° C. add 1,2-dibromoethane (0.87 g, 4.6 mmol), and react at room temperature for 24 h. Add saturated ammonium chloride solution (5 mL) and water (15 mL) to the reaction system, extract with ethyl acetate twice (10 mL each time), combine organic phase, wash with saturated salt solution once, dry with anhydrous sodium sulfate, filter and concentrate with vacuum, and purify the concentrate by silica gel column chromatography (petroleum ether/ethyl acetate=4:1) to obtain the title compound (0.16 g, 53%). ESI-QQQ-MS: m/z 1% $[M+H]^+$.

Intermediate Preparation Example 13: Synthesis of 7-chloro-3,3-Dimethylindolin-2-one (P-13)

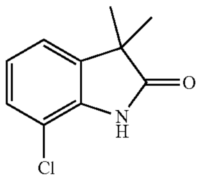

Dissolve 7-chloroindoline-2-one (0.34 g, 2 mmol) in anhydrous tetrahydrofuran (3 mL), cool to −40° C., add LDA (2 mol/L, 4 mL, 8 mmol), stir for 30 min, heat to 0° C. add iodomethane (0.85 g, 6 mmol), and react at room temperature for 24 h. Add saturated ammonium chloride solution (5 mL) and water (15 mL) to the reaction system, extract with ethyl acetate twice (10 mL each time), combine organic phase, wash with saturated salt solution once, dry with anhydrous sodium sulfate, filter and concentrate with vacuum, and purify the concentrate by silica gel column chromatography (petroleum ether/ethyl acetate=4:1) to obtain the title compound (024 g, 61%). ESI-QQQ-MS: m/z 196 $[M+H]^+$.

Intermediate Preparation Example 14: Synthesis of 7-chloro-2',3',5',6'-tetrahydrospiro[indoline-3,4'-pyran]-2-one (P-14)

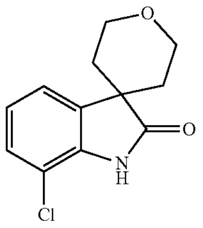 [SMILES: O=C1Nc2c(Cl)cccc2C12CCOCC2]

Dissolve 7-chloroindoline-2-one (0.34 g, 2 mmol) in anhydrous tetrahydrofuran (3 mL), cool to −40° C., add LDA (2 mol/L, 4 mL, 8 mmol), stir for 30 min, heat to 0° C. add 1-iodo-2-(2-iodoethoxy)ethane (1.96 g, 6 mmol), and react at room temperature for 241. Add saturated ammonium chloride solution (5 mL) and water (15 mL) to the reaction system, extract with ethyl acetate twice (10 mL each time), combine organic phase, wash with saturated salt solution once, dry with anhydrous sodium sulfate, filter and concentrate with vacuum, and purify the concentrate by silica gel column chromatography (petroleum ether/ethyl acetate=4:1) to obtain the title compound (0.23 g, 49%). ESI-QQQ-MS: m/z 238 $[M+H]^+$.

Intermediate Preparation Example 15: Synthesis of 5'-(dimethylamino) spiro[cyclopropane-1,3'-indoline]-2'-one (P-15)

(Step 1) 5-(dimethylamino) indoline-2-one

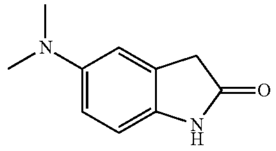

Dissolve 5-aminoindoline-2-one (0.30 g, 2 mmol) in glacial acetic acid (4 mL), add sodium cyanoborohydride (0.31 g, 5 mmol) and paraformaldehyde (0.48 g, 16 mmol) sequentially, and react at room temperature for 24 h. Concentrate the reaction system with vacuum and add water (20 mL) to the reaction system, extract with ethyl acetate twice (10 mL each time), combine organic phase, wash with saturated salt solution once, dry with anhydrous sodium sulfate, filter and concentrate with vacuum, and purify the concentrate by silica gel column chromatography (dichloromethane/methanol=30:1) to obtain the title compound (0.24 g, 68%). ESI-QQQ-MS: m/z 177 $[M+H]^+$.

(Step 2) 5'-(dimethylamino) spiro[cyclopropane-1, 3'-indoline]-2'-one (P-15)

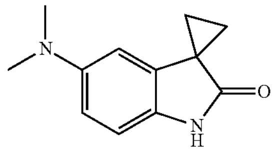

Dissolve 5-(dimethylamino) indoline-2-one (0.24 g, 1.35 mmol) in anhydrous tetrahydrofuran (3 mL), cool to −40° C. add LDA (2 mol/L, 2.7 mL, 5.4 mmol), stir for 30 min, heat to 0° C., add 1,2-dibromoethane (0.76 g, 4.05 mmol), and react at room temperature for 24 h. Add saturated ammonium chloride solution (5 mL) and water (15 mL) to the reaction system, extract with ethyl acetate twice (10 mL each time), combine organic phase, wash with saturated salt solution once, dry with anhydrous sodium sulfate, filter and concentrate with vacuum, and purify the concentrate by silica gel column chromatography (petroleum ether/ethyl acetate=4:1) to obtain the title compound (0.11 g, 40%). ESI-QQQ-MS: m/z 203 $[M+H]^+$.

Intermediate Preparation Example 16: Synthesis of 6'-(dimethylamino)-5'-fluorospiro[cyclopropane-1, 3'-indoline]-2'-one (P-16)

(Step 1) 6-(dimethylamino)-5-fluoroindolin-2-one

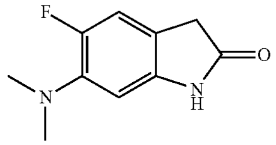

Dissolve 6-amino-5-fluoroindolin-2-one (0.33 g, 2 mmol) in glacial acetic acid (4 mL), add sodium cyanoborohydride (0.31 g, 5 mmol) and paraformaldehyde (0.48 g, 16 mmol) sequentially, and react at room temperature for 24 h. Concentrate the reaction system with vacuum and add water (20 mL) and ethyl acetate (10 mL) to the reaction system, stand for layering, extract with ethyl acetate twice (10 mL each time), combine organic phase, wash with saturated salt solution once, dry with anhydrous sodium sulfate, filter and concentrate with vacuum, and purify the concentrate by silica gel column chromatography (dichloromethane/methanol=30:1) to obtain the title compound (0.25 g, 65%). ESI-QQQ-MS: m/z 195 $[M+H]^+$.

(Step 2) 6'-(dimethylamino)-5'-fluorospiro[cyclopropane-1,3'-indoline]-2'-one (P-16)

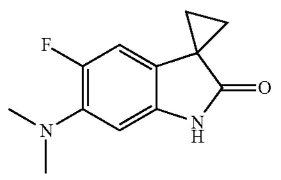 [SMILES: CN(C)c1cc2c(cc1F)C1(CC1)C(=O)N2]

Dissolve 6-(dimethylamino)-5-fluoroindolin-2-one (0.24 g, 1.3 mmol) in anhydrous tetrahydrofuran (3 mL), cool to −40° C. add LDA (2 mol/L, 2.6 mL, 5.2 mmol), stir for 30 min, heat to 0° C. add 1,2-dibromoethane (0.73 g, 3.9 mmol), and react at room temperature for 24 h. Add saturated ammonium chloride solution (5 mL) and water (15 mL) to the reaction system, extract with ethyl acetate twice (10 mL each time), combine organic phase, wash with saturated salt solution once, dry with anhydrous sodium sulfate, filter and concentrate with vacuum, and purify the concentrate by silica gel column chromatography (petroleum ether/ethyl acetate=4:1) to obtain the title compound (0.12 g, 42%). ESI-QQQ-MS: m/z 221 $[M+H]^+$.

Intermediate Preparation Example 17: Synthesis of spiro[cyclopropane-1,3'-pyrrolo[2,3-B]pyridine]-2'(1'H)-one (P-17)

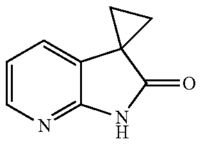 [SMILES: O=C1Nc2ncccc2C12CC2]

Dissolve 1H-pyrrolo[2,3-b]pyridine-2(3H)-one (0.27 g, 2 mmol) in anhydrous tetrahydrofuran (3 mL), cool to −40° C., add LDA (2 mol/L, 4 mL, 8 mmol), stir for 30 min, heat to 0° C., add 1,2-dibromoethane (1.14 g, 6 mmol), and react at room temperature for 24 h. Add saturated ammonium chloride solution (5 mL) and water (15 mL) to the reaction system, extract with ethyl acetate for three times (10 mL each time), combine organic phase, wash with saturated salt solution once, dry with anhydrous sodium sulfate, filter and concentrate with vacuum, and purify the concentrate by silica gel column chromatography (petroleum ether/ethyl acetate=3:1) to obtain the title compound (0.11 g, 34%). ESI-QQQ-MS: m/z 161 $[M+H]^+$.

Intermediate Preparation Example 18: Synthesis of 4-chloro-1-methyl-1H-benzo[d]imidazole-2(3H)-one (P-18)

(Step 1) 3-chloro-N-methyl-2-nitroaniline

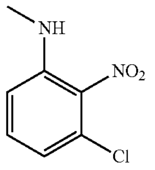

Dissolve 1-chloro-3-fluoro-2-nitrobenzene (0.35 g, 2 mmol) in absolute ethanol (4 mL), add N,N-diisopropylethylamine (0.34 g, 2.6 mmol) and 33% methylamine ethanol solution (0.23 g, 2.4 mmol), heat to reflux, stir for 20 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.37 g, 98%). ESI-QQQ-MS: m/z 187 $[M+H]^+$.

(Step 2) 3-chloro-$N^1$-methylbenzene-1,2-diamine

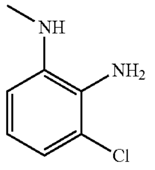

Dissolve 3-chloro-N-methyl-2-nitroaniline (0.3 g, 1.6 mmol) in anhydrous methanol (4.5 mL), add zinc powder (1 g, 16 mmol) and ammonium chloride (0.43 g, 8 mmol), heat to 50° C., and stir for 3 h. Filter the reaction solution with vacuum, rinse the filter cake twice with absolute ethanol (2 mL each time), combine the filtrate, and concentrate with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.24 g, 98%). ESI-QQQ-MS: m/z 157 $[M+H]^+$.

(Step 3) 4-chloro-1-methyl-1H-benzo[d]imidazole-2(3H)-one (P-18)

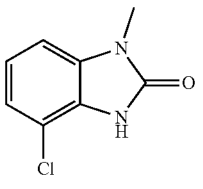

Dissolve 3-chloro-$N^1$-methylbenzene-1,2-diamine (0.2 g, 1.3 mmol) in dichloromethane (2 mL), cool to 0° C., add triethylamine (0.16 g, 1.6 mmol), and slowly add triphosgene/dichloromethane solution (0.15 g/1 mL) dropwise to the reaction system, and react at room temperature for 1 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum, and purify the concentrate with silica gel column chromatography (petroleum ether/ethyl acetate=4:1) to obtain the title compound (0.19 g, 80%). ESI-QQQ-MS: m/z 183 $[M+H]^+$.

Intermediate Preparation Example 19: Synthesis of 6-chloro-1-cyclopropyl-1H-benzo[d]imidazole-2(3H)-one (P-19)

(Step 1) 5-chloro-N-cyclopropyl-2-nitroaniline

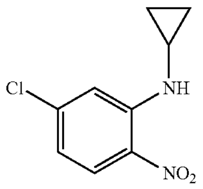 [SMILES: O=[N+]([O-])c1ccc(Cl)cc1NC1CC1]

Dissolve 4-chloro-2-fluoro-1-nitrobenzene (0.35 g, 2 mmol) in absolute ethanol (4 mL), add N,N-diisopropylethanamine (0.34 g, 2.6 mmol) and cyclopropylamine (0.14 g, 2.4 mmol), heat to reflux, and stir for 20 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.35 g, 82%). ESI-QQQ-MS: m/z 213 $[M+H]^+$.

(Step 2) 5-chloro-$N^1$-cyclopropylbenzene-1,2-diamine

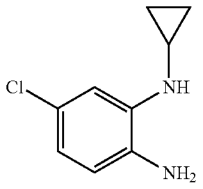 [SMILES: Nc1ccc(Cl)cc1NC1CC1]

Dissolve 5-chloro-N-cyclopropyl-2-nitroaniline (0.34 g, 1.6 mmol) in anhydrous methanol (4.5 mL), add zinc powder (1 g, 16 mmol) and ammonium chloride (0.43 g, 8 mmol), heat to 50° C., and stir for 3 h. Filter the reaction solution with vacuum, rinse the filter cake twice with absolute ethanol (2 mL each time), combine the filtrate, and concentrate with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.27 g, 92%). ESI-QQQ-MS: m/z 183 $[M+H]^+$.

(Step 3) 6-chloro-1-cyclopropyl-1H-benzo[d]imidazole-2(3H)-one (P-19)

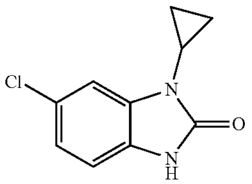 [SMILES: O=c1[nH]c2ccc(Cl)cc2n1C1CC1]

Dissolve 5-chloro-N1-cyclopropylbenzene-1,2-diamine (0.24 g, 1.3 mmol) in dichloromethane (2 mL), cool to 0° C., add triethylamine (0.16 g, 1.6 mmol), and slowly add triphosgene/dichloromethane solution (0.15 g/1 mL) dropwise to the reaction system, react at room temperature for 1 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum, and purify the concentrate with silica gel column chromatography (petroleum ether/ethyl acetate=4:1) to obtain the title compound (0.20 g, 74%). ESI-QQQ-MS: m/z 209 $[M+H]^+$.

Intermediate Preparation Example 20: Synthesis of 5-chloro-1-cyclopropyl-1H-benzo[d]imidazole-2(3H)-one (P-20)

(Step 1) 4-chloro-N-cyclopropyl-2-nitroaniline

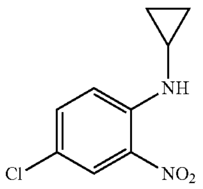

Dissolve 4-chloro-1-fluoro-2-nitrobenzene (0.35 g, 2 mmol) in absolute ethanol (4 mL), add N,N-diisopropylethanamine (0.34 g, 2.6 mmol) and cyclopropylamine (0.14 g, 2.4 mmol), heat to reflux, stir for 20 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.35 g, 85%). ESI-QQQ-MS: m/z 213 $[M+H]^+$.

(Step 2) 4-chloro-$N^1$-cyclopropylbenzene-1,2-diamine

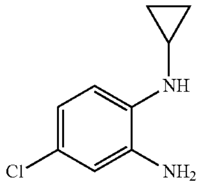 [SMILES: Nc1cc(Cl)ccc1NC1CC1]

Dissolve 4-chloro-N-cyclopropyl-2-nitroaniline (0.34 g, 1.6 mmol) in anhydrous methanol (4.5 mL), add zinc powder (1 g, 16 mmol) and ammonium chloride (0.43 g, 8 mmol), heat to 50° C., stir for 3 h. Filter the reaction solution with vacuum, rinse the filter cake twice with absolute ethanol (2 mL each time), combine the filtrate, and concentrate with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.26 g, 90%). ESI-QQQ-MS: m/z 183 $[M+H]^+$.

(Step 3) 5-chloro-1-cyclopropyl-1H-benzo[d]imidazole-2(3H)-one (P-20)

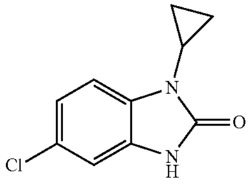 [SMILES: O=c1[nH]c2cc(Cl)ccc2n1C1CC1]

Dissolve 4-chloro-$N^1$-cyclopropylbenzene-1,2-diamine (0.24 g, 1.3 mmol) in dichloromethane (2 mL), cool to 0° C., add triethylamine (0.16 g, 1.6 mmol), and slowly add triphosgene/dichloromethane solution (0.15 g/1 mL) dropwise to the reaction system, and react at rom temperature for 1 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum, and purify the concentrate with silica gel column chromatography (petroleum ether/ethyl acetate=4:1) to obtain the title compound (0.19 g, 70%). ESI-QQQ-MS: m/z 209 $[M+H]^+$.

Intermediate Preparation Example 21: Synthesis of 4-chloro-1-cyclopropyl-1H-benzo[d]imidazole-2(3H)-one (P-21)

(Step 1) 3-chloro-N-cyclopropyl-2-nitroaniline

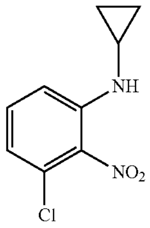

Dissolve 1-chloro-3-fluoro-2-nitrobenzene (0.35 g, 2 mmol) in absolute ethanol (4 mL), add N,N-diisopropylethanamine (0.34 g, 2.6 mmol) and cyclopropylamine (0.14 g, 2.4 mmol), heat to reflux, stir for 20 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.37 g, 87%). ESI-QQQ-MS: m/z 213 $[M+H]^+$.

(Step 2) 3-chloro-$N^1$-cyclopropylbenzene-1,2-diamine

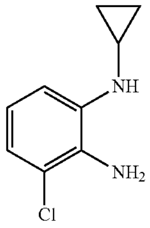 [SMILES: O=[N+]([O-])c1c(Cl)cccc1NC1CC1]

Dissolve 3-chloro-N-cyclopropyl-2-nitroaniline (0.34 g, 1.6 mmol) in anhydrous methanol (4.5 mL), add zinc powder (1 g, 16 mmol) and ammonium chloride (0.43 g, 8 mmol), heat to 50° C. and stir for 3 h. Filter the reaction solution with vacuum, rinse the filter cake twice with absolute ethanol (2 mL each time), combine the filtrate, and concentrate with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.27 g, 93%). ESI-QQQ-MS: m/z 183 $[M+H]^+$.

(Step 3) 4-chloro-1-cyclopropyl-1H-benzo[d]imidazole-2(3H)-one (P-21)

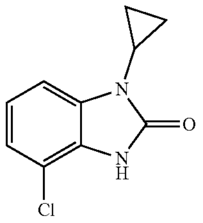 [SMILES: O=c1[nH]c2c(Cl)cccc2n1C1CC1]

Dissolve 3-chloro-N1-cyclopropylbenzene-1,2-diamine (0.24 g, 1.3 mmol) in dichloromethane (2 mL), cool to 0° C., add triethylamine (0.16 g, 1.6 mmol), and slowly add triphosgene/dichloromethane solution (0.15 g/1 mL) dropwise to the reaction system, and react at room temperature for 1 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum, and purify the concentrate with silica gel column chromatography (petroleum ether/ethyl acetate=4:1) to obtain the title compound (0.18 g, 66%). ESI-QQQ-MS: m/z 209 $[M+H]^+$.

Intermediate Preparation Example 22: Synthesis of 4-chloro-1-methyl-1H-benzo[d]imidazole-2(3H)-thione (P-22)

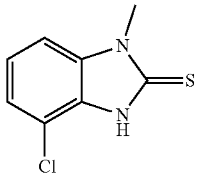

Dissolve 3-chloro-$N^1$-methylbenzene-1,2-diamine (0.24 g, 1.3 mmol) in dichloromethane (2 mL), cool to 0° C. add triethylamine (0.16 g, 1.6 mmol), and slowly add sulfurphosgene/dichloromethane solution (0.18 g/1 mL) dropwise to the reaction system, react at room temperature for 1 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum, and purify the concentrate with silica gel column chromatography (petroleum ether/ethyl acetate=4:1) to obtain the title compound (0.14 g, 54%). ESI-QQQ-MS: m/z 199 $[M+H]^+$.

Intermediate Preparation Example 23: Synthesis of 4-chloro-1-(tetrahydro-2H-pyran-4-yl)-1H-benzo[d]imidazole-2(3H)-one (P-23)

(Step 1) N-(3-chloro-2-nitrophenyl) tetrahydro-2H-pyran-4-amine

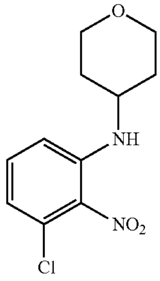 [SMILES: O=[N+]([O-])c1c(Cl)cccc1NC1CCOCC1]

Dissolve 1-chloro-3-fluoro-2-nitrobenzene (0.35 g, 2 mmol) in absolute ethanol (4 mL), add N,N-diisopropylethanamine (0.34 g, 2.6 mmol) and tetrahydro-2H-pyran-4-amine (0.24 g, 2.4 mmol), heat to reflux, and stir for 20 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.30 g, 59%). ESI-QQQ-MS: m/z 257 $[M+H]^+$.

(Step 2) 3-chloro-$N^1$-(tetrahydro-2H-pyran-4-yl) benzene-1,2-diamine

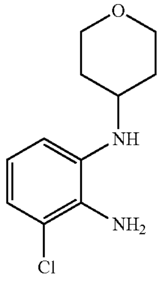 [SMILES: Nc1c(Cl)cccc1NC1CCOCC1]

Dissolve N-(3-chloro-2-nitrophenyl)tetrahydro-2H-pyran-4-amine (0.28 g, 1.1 mmol) in anhydrous methanol (4 mL), add zinc powder (0.72 g, 1 mmol) and ammonium chloride (0.29 g, 5.5 mmol), heat to 50° C., and stir for 3 h. Perform suction filtration for reaction solution, rinse the filter cake twice with absolute ethanol (2 mL each time), combine the filtrate, and concentrate with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.22 g, 89%). ESI-QQQ-MS: m/z 227 $[M+H]^+$.

(Step 3) 4-chloro-1-(tetrahydro-2H-pyran-4-yl)-1H-benzo[d]imidazole-2(3H)-one (P-23)

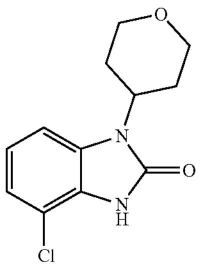 [SMILES: O=c1[nH]c2c(Cl)cccc2n1C1CCOCC1]

Dissolve 3-chloro-$N^1$-(tetrahydro-2H-pyran-4-yl)benzene-1,2-diamine (0.22 g, 0.97 mmol) in dichloromethane (2 mL), cool to ° C. add triethylamine (0.13 g, 1.3 mmol), and slowly add triphosgene/dichloromethane solution (0.12 g/1 mL) dropwise to the reaction system, and react at room temperature for 1 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum, and purify, the concentrate with silica gel column chromatography (petroleum ether/ethyl acetate=2:1) to obtain the title compound (0.12 g, 49%). ESI-QQQ-MS: m/z 253 $[M+H]^+$.

Intermediate Preparation Example 24: Synthesis of 4-chloro-1-(1-methylpiperidine-4-yl)-1H-benzo[d]imidazole-2(3H)-one (P-24)

(Step 1) N-(3-chloro-2-nitrophenyl)-1-methylpiperidine-4-amine

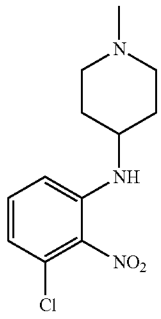 [SMILES: CN1CCC(Nc2cccc(Cl)c2[N+](=O)[O-])CC1]

Dissolve 1-chloro-3-fluoro-2-nitrobenzene (0.35 g, 2 mmol) in absolute ethanol (4 mL), add N,N-diisopropylethylamine (0.34 g, 2.6 mmol) and 1-methylpiperidine-4-amine (0.27 g, 2.4 mmol), heat to reflux, stir for 20 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.28 g, 51%). ESI-QQQ-MS: m/z 270 $[M+H]^+$.

(Step 2) 3-chloro-$N^1$-(1-methylpiperidine-4-yl) benzene-1,2-diamine

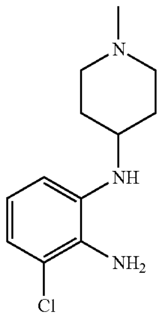 [SMILES: CN1CCC(Nc2cccc(Cl)c2N)CC1]

Dissolve N-(3-chloro-2-nitrophenyl)-1-methylpiperidine-4-amine (0.27 g, 1.0 mmol) in anhydrous methanol (4 mL), add zinc powder (0.65 g, 10 mmol) and ammonium chloride (0.27 g, 5 mmol), heat to 50° C., and stir for 3 h. Filter the reaction solution with vacuum, rinse the filter cake twice with absolute ethanol (2 mL each time), combine the filtrate, and concentrate with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.22 g, 92%). ESI-QQQ-MS: m/z 240 $[M+H]^+$.

(Step 3) 4-chloro-1-(1-methylpiperidine-4-yl)-1H-benzo[d]imidazole-2(3H)-one (P-24)

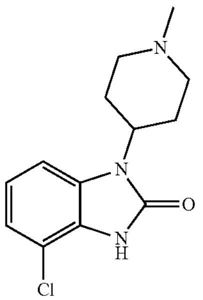 [SMILES: CN1CCC(n2c(=O)[nH]c3c(Cl)cccc32)CC1]

Dissolve 3-chloro-$N^1$-(1-methylpiperidine-4-yl)benzene-1,2-diamine (0.22 g, 0.92 mmol) in dichloromethane (2 mL), cool to 0° C., add triethylamine (0.12 g, 1.2 mmol), and slowly add triphosgene/dichloromethane solution (0.11 g/1 mL) dropwise to the reaction system, and react at room temperature for 1 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum, and purify, the concentrate with silica gel column chromatography (petroleum ether/ethyl acetate=1:1) to obtain the title compound (0.11 g, 45%). ESI-QQQ-MS: m/z 266 $[M+H]^+$.

Intermediate Preparation Example 25: Synthesis of 4-fluoro-1-methyl-1H-benzo[d]imidazole-2(3H)-one (P-25)

(Step 1) 3-fluoro-N-methyl-2-nitroaniline

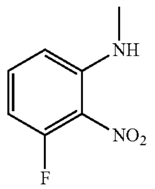

Dissolve 1,3-difluoro-2-nitrobenzene (0.32 g, 2 mmol) in absolute ethanol (4 mL), add N,N-diisopropylethylamine (0.34 g, 2.6 mmol) and 33% methylamine ethanol solution (0.23 g, 2.4 mmol), heat to reflux, stir for 20 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.32 g, 95%). ESI-QQQ-MS: m/z 171 $[M+H]^+$.

(Step 2) 3-fluoro-$N^1$-methylbenzene-1,2-diamine

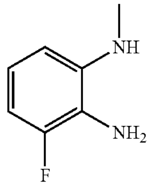

Dissolve 3-fluoro-N-methyl-2-nitroaniline (0.27 g, 1.6 mmol) in anhydrous methanol (4.5 mL), add zinc powder (1 g, 16 mmol) and ammonium chloride (0.43 g, 8 mmol), heat to 50° C. and stir for 3 h. Filter the reaction solution with vacuum, rinse the filter cake twice with absolute ethanol (2 mL each time), combine the filtrate, and concentrate with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.22 g, 98%). ESI-QQQ-MS: m/z 141 $[M+H]^+$.

(Step 3) 4-fluoro-1-methyl-1H-benzo[d]imidazole-2(3H)-one (P-25)

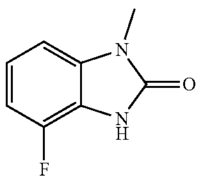

Dissolve 3-fluoro-$N^1$-methylbenzene-1,2-diamine (0.18 g, 1.3 mmol) in dichloromethane (2 mL), cool to 0° C., add triethylamine (0.16 g, 1.6 mmol), and slowly add triphosgene/dichloromethane solution (0.15 g/1 mL) dropwise to the reaction system, and react at room temperature for 1 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum, and purify the concentrate with silica gel column chromatography (petroleum ether/ethyl acetate=4:1) to obtain the title compound (0.17 g, 78%). ESI-QQQ-MS: m/z 167 $[M+H]^+$.

Intermediate Preparation Example 26: Synthesis of 4,6-difluoro-1-methyl-1H-benzo[d]imidazole-2(3H)-one (P-26)

(Step 1) 3,5-difluoro-N-methyl-2-nitroaniline

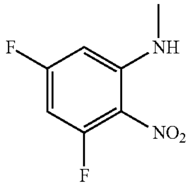

Dissolve 1,3,5-trifluoro-2-nitrobenzene (0.35 g, 2 mmol) in absolute ethanol (4 mL), add N,N-diisopropylethanamine (0.34 g, 2.6 mmol) and 33% methylamine ethanol solution (0.23 g, 2.4 mmol), heat to reflux, stir for 20 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.26 g, 70%). ESI-QQQ-MS: m/z 189 $[M+H]^+$.

(Step 2) 3,5-difluoro-$N^1$-methylbenzene-1,2-diamine

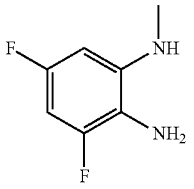

Dissolve 3,5-difluoro-N-methyl-2-nitroaniline (0.24 g, 1.3 mmol) in anhydrous methanol (4.5 mL), add zinc powder (0.85 g, 13 mmol) and ammonium chloride (0.35 g, 6.5 mmol), heat to 50° C., and stir for 3 h. Filter the reaction solution with vacuum, rinse the filter cake twice with absolute ethanol (2 mL each time), combine the filtrate, and concentrate with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.19 g, 92%). ESI-QQQ-MS: m/z 159 $[M+H]^+$.

(Step 3) 4,6-difluoro-1-methyl-1H-benzo[d]imidazole-2(3H)-one (P-26)

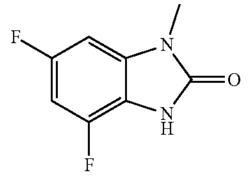

Dissolve 3,5-difluoro-$N^1$-methylbenzene-1,2-diamine (0.17 g, 1.1 mmol) in dichloromethane (2 mL), cool to 0° C., add triethylamine (0.14 g, 1.4 mmol), and slowly add triphosgene/dichloromethane solution (0.15 g/1 mL) dropwise to the reaction system, react at room temperature for 1 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum, and purify the concentrate with silica gel column chromatography (petroleum ether/ethyl acetate=4:1) to obtain the title compound (0.16 g, 80%). ESI-QQQ-MS: m/z 185 $[M+H]^+$.

Intermediate Preparation Example 27: Synthesis of 5,6-dichloro-1-methyl-1H-benzo[d]imidazole-2(3H)-one (P-27)

(Step 1) 4,5-dichloro-N-methyl-2-nitroaniline

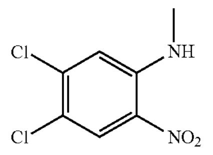

Dissolve 1,2-dichloro-4-fluoro-5-nitrobenzene (0.42 g, 2 mmol) in absolute ethanol (4 mL), add N,N-diisopropylethanamine (0.34 g, 2.6 mmol) and 33% methylamine ethanol solution (0.23 g, 2.4 mmol), heat to reflux, stir for 20 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.4 g, 90%). ESI-QQQ-MS: m/z 221 $[M+H]^+$.

(Step 2) 4,5-dichloro-$N^1$-methylbenzene-1,2-diamine

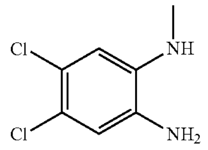

Dissolve 4,5-dichloro-N-methyl-2-nitroaniline (0.35 g, 1.6 mmol) in anhydrous methanol (4.5 mL), add zinc powder (1.0 g, 16 mmol) and ammonium chloride (0.43 g, 8 mmol), heat to 50° C., and stir for 3 h. Filter the reaction solution with vacuum, rinse the filter cake twice with absolute ethanol (2 mL each time), combine the filtrate, and concentrate with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.29 g, 95%). ESI-QQQ-MS: m/z 191 $[M+H]^+$.

(Step 3) 5,6-dichloro-1-methyl-1H-benzo[d]imidazole-2(3H)-one (P-27)

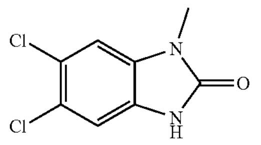

Dissolve 4,5-dichloro-$N^1$-methylbenzene-1,2-diamine (0.29 g, 1.5 mmol) in dichloromethane (2 mL), cool to 0° C., add triethylamine (0.14 g, 1.9 mmol), and slowly add triphosgene/dichloromethane solution (0.18 g/1 mL) dropwise to the reaction system and react at room temperature for 1 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum, and purify the concentrate with silica gel column chromatography (petroleum ether/ethyl acetate=4:1) to obtain the title compound (0.24 g, 74%). ESI-QQQ-MS: m/z 217 $[M+H]^+$.

Intermediate Preparation Example 28: Synthesis of 1-cyclopropyl-4-fluoro-1H-benzo[d]imidazole-2(3H)-one (P-28)

(Step 1) N-cyclopropyl-3-fluoro-2-nitroaniline

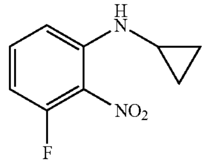 [SMILES: O=[N+]([O-])c1c(F)cccc1NC1CC1]

Dissolve 1,3-difluoro-2-nitrobenzene (0.32 g, 2 mmol) in absolute ethanol (4 mL), add N,N-diisopropylethanamine (0.34 g, 2.6 mmol) and cyclopropylamine (0.14 g, 2.4 mmol), heat to reflux, stir for 20 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.35 g, 90%). ESI-QQQ-MS: m/z 197 $[M+H]^+$.

(Step 2) $N^1$-cyclopropyl 3-fluorobenzene-1,2-diamine

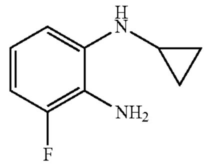 [SMILES: Nc1c(F)cccc1NC1CC1]

Dissolve N-cyclopropyl-3-fluoro-2-nitroaniline (0.31 g, 1.6 mmol) in anhydrous methanol (4.5 mL), add zinc powder (1 g, 16 mmol) and ammonium chloride (0.43 g, 8 mmol), heat to 50° C. and stir for 3 h. Filter the reaction solution with vacuum, rinse the filter cake twice with absolute ethanol (2 mL each time), combine the filtrate, and concentrate with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.26 g, 96%). ESI-QQQ-MS: m/z 167 $[M+H]^+$.

(Step 3) 1-cyclopropyl-4-fluoro-1H-benzo[d]imidazole-2(3H)-one (P-28)

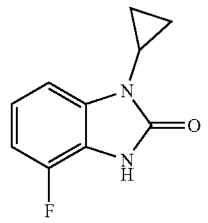 [SMILES: O=c1[nH]c2c(F)cccc2n1C1CC1]

Dissolve $N^1$-cyclopropyl 3-fluorobenzene-1,2-diamine (0.22 g, 1.3 mmol) in dichloromethane (2 mL), cool to 0° C. add triethylamine (0.16 g, 1.6 mmol), and slowly add triphosgene/dichloromethane solution (0.15 g/1 mL) dropwise to the reaction system and react at room temperature for 1 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum, and purify the concentrate with silica gel column chromatography (petroleum ether/ethyl acetate=4:1) to obtain the title compound (0.19 g, 75%). ESI-QQQ-MS: m/z 193 $[M+H]^+$.

Intermediate Preparation Example 29: Synthesis of 4,5-difluoro-1-methyl-1H-benzo[d]imidazole-2(3H)-one (P-29)

(Step 1) 1,2,4-trifluoro-3-nitrobenzene

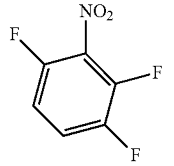 [SMILES: O=[N+]([O-])c1c(F)ccc(F)c1F]

Mix 65% concentrated nitric acid (2 mL) and 98% concentrated sulfuric acid (4 mL), and slowly add 1,2,4-trifluorobenzene (1.32 g) dropwise, and react at 30° C. for 2 h. Stand for layering, wash the organic phase twice with saturated sodium carbonate solution and wash with saturated salt solution, concentrate with vacuum to obtain the title compound (1.7 g, 95%). ESI-QQQ-MS: m/z 178 $[M+H]^+$.

(Step 2) 3,4-difluoro-N-methyl-2-nitroaniline

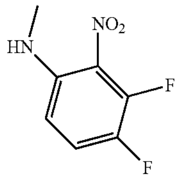

Dissolve 1,2,4-trifluoro-3-nitrobenzene (0.35 g, 2 mmol) in absolute ethanol (4 mL), add N,N-diisopropylethanamine (0.34 g, 2.6 mmol) and 33% methylamine ethanol solution (0.23 g, 2.4 mmol) and heat to 50° C. for 12 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.2 g, 50%). ESI-QQQ-MS: m/z 189 $[M+H]^+$.

(Step 3) 3,4-difluoro-$N^1$-methylbenzene-1,2-diamine

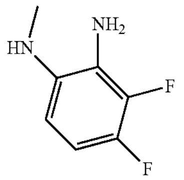

Dissolve 3,4-difluoro-N-methyl-2-nitroaniline (0.19 g, 1 mmol) in anhydrous methanol (3 mL), add zinc powder (0.66 g, 10 mmol) and ammonium chloride (0.27 g, 5 mmol), heat to 50° C., and stir for 3 h. Filter the reaction solution with vacuum, rinse the filter cake twice with absolute ethanol (2 mL each time), combine the filtrate, and concentrate with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.14 g, 90%). ESI-QQQ-MS: m/z 159 $[M+H]^+$.

(Step 4) 4,5-difluoro-1-methyl-1H-benzo[d]imidazole-2(3H)-one (P-29)

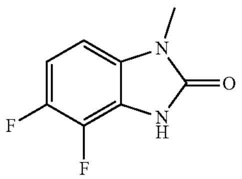

Dissolve 3,4-difluoro-$N^1$-methylbenzene-1,2-diamine (0.14 g, 0.89 mmol) in dichloromethane (2 mL), cool to 0° C., add triethylamine (0.1 g, 1.2 mmol), and slowly add triphosgene/dichloromethane solution (0.1 g/1 mL) dropwise to the reaction system, react at room temperature for 1 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum, and purify the concentrate with silica gel column chromatography (petroleum ether/ethyl acetate=4:1) to obtain the title compound (0.12 g, 74%). ESI-QQQ-MS: m/z 185 $[M+H]^+$.

Intermediate Preparation Example 30: Synthesis of 6,7-difluoro-1-methyl-1H-benzo[d]imidazole-2(3H)-one (P-30)

(Step 1) 2,3-difluoro-N-methyl-6-nitroaniline

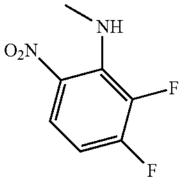

Dissolve 1,2,3-trifluoro-4-nitrobenzene (0.35 g, 2 mmol) in absolute ethanol (4 mL), add N,N-diisopropylethanamine (0.34 g, 2.6 mmol) and 33% methylamine ethanol solution (0.23 g, 2.4 mmol), heat to 50° C. and react for 121. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.24 g, 60%). ESI-QQQ-MS: m/z 189 $[M+H]^+$.

(Step 3) 5,6-difluoro-$N^1$-methylbenzene-1,2-diamine

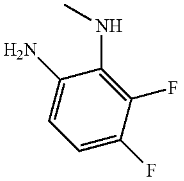

Dissolve 3,4-difluoro-N-methyl-2-nitroaniline (0.19 g, 1 mmol) in anhydrous methanol (3 mL), add zinc powder (0.66 g, 10 mmol) and ammonium chloride (0.27 g, 5 mmol), heat to 50° C., and stir for 3 h. Filter the reaction solution with vacuum, rinse the filter cake twice with absolute ethanol (2 mL each time), combine the filtrate, and concentrate with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.14 g, 88%). ESI-QQQ-MS: m/z 159 $[M+H]^+$.

(Step 4) 6,7-difluoro-1-methyl-1H-benzo[d]imidazole-2(3H)-one (P-30)

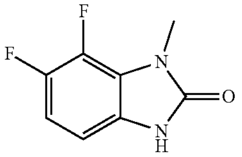

Dissolve 3,4-difluoro-$N^1$-methylbenzene-1,2-diamine (0.12 g, 0.76 mmol) in dichloromethane (2 mL), cool to 0° C. add triethylamine (0.1 g, 1.2 mmol), and slowly add triphosgene/dichloromethane solution (0.1 g/1 mL) dropwise to the reaction system, react at room temperature for 1 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum, and purify the concentrate with silica gel column chromatography (petroleum ether/ethyl acetate=4:1) to obtain the title compound (0.13 g, 80%). ESI-QQQ-MS: m/z 185 $[M+H]^+$.

Intermediate Preparation Example 31: Synthesis of 4-methoxy-1-methyl-1H-benzo[d]imidazole-2(3H)-one (P-31)

(Step 1) 3-methoxy-N-methyl-2-nitroaniline

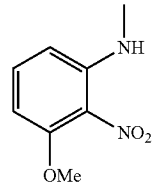

Dissolve 1-fluoro-3-methoxy-2-nitrobenzene (0.34 g, 2 mmol) in absolute ethanol (4 mL), add N,N-diisopropylethylamine (0.34 g, 2.6 mmol) and 33% methylamine ethanol solution (0.23 g, 2.4 mmol), heat to reflux, stir for 20 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.29 g, 80%). ESI-QQQ-MS: m/z 183 $[M+H]^+$.

(Step 2) 3-methoxy-$N^1$-methylbenzene-1,2-diamine

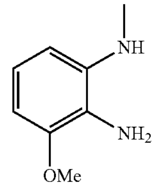

Dissolve 3-methoxy-N-methyl-2-nitroaniline (0.27 g, 1.5 mmol) in anhydrous methanol (4.5 mL), add zinc powder (0.98 g, 15 mmol) and ammonium chloride (0.4 g, 7.5 mmol), heat to 50° C., stir for 3 h. Filter the reaction solution with vacuum, rinse the filter cake twice with absolute ethanol (2 mL each time), combine the filtrate, and concentrate with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.21 g, 92%). ESI-QQQ-MS: m/z 153 $[M+H]^+$.

(Step 3) 4-methoxy-1-methyl-1H-benzo[d]imidazole-2(3H)-one (P-31)

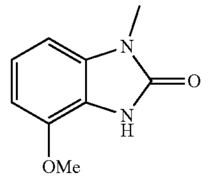

Dissolve 3-methoxy-$N^1$-methylbenzene-1,2-diamine (0.2 g, 1.3 mmol) in dichloromethane (2 mL), cool to 0° C., add triethylamine (0.14 g, 1.7 mmol), and slowly add triphosgene/dichloromethane solution (0.15 g/1 mL) dropwise to the reaction system, and react at room temperature for 1 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum, and purify the concentrate with silica gel column chromatography (petroleum ether/ethyl acetate=4:1) to obtain the title compound (0.16 g, 70%). ESI-QQQ-MS: m/z 179 $[M+H]^+$.

Intermediate Preparation Example 32: Synthesis of 5-(dimethylamino)-1-methyl-1H-benzo[d]imidazole-2(3H)-one (P-32)

(Step 1) $N^1$-methyl-4-nitrobenzene-1,2-diamine

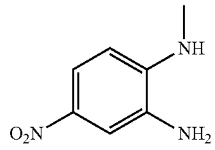

Dissolve 4-nitrobenzene-1,2-diamine (0.33 g, 2 mmol) in DMF (4 mL), add saturated sodium carbonate solution (0.5 mL) and iodomethane (0.24 g, 1.7 mmol) sequentially, and react at room temperature for 1 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum, and purify the concentrate with silica gel column chromatography (petroleum ether/ethyl acetate=4:1) to obtain the title compound (0.2 g, 60%). ESI-QQQ-MS: m/z 168 $[M+H]^+$.

(Step 2) 1-methyl-5-nitro-1H-benzo[d]imidazole-2(3H)-one

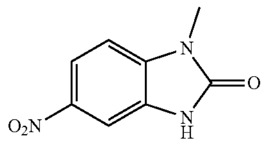

Dissolve $N^1$-methyl-4-nitrobenzene-1,2-diamine (0.2 g, 1.3 mmol) in dichloromethane (4 mL), cool to 0° C. add triethylamine (0.16 g, 1.6 mmol), and slowly add triphosgene/dichloromethane solution (0.14 g/1 mL) dropwise to the reaction system, and react at rom temperature for 1 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum, and purify the concentrate with silica gel column chromatography (dichloromethane/methanol=20:1) to obtain the title compound (0.16 g, 68%). ESI-QQQ-MS: m/z 194 $[M+H]^+$.

(Step 3) 5-amino-1-methyl-1H-benzo[d]imidazole-2(3H)-one

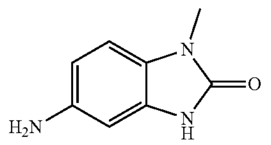

Dissolve 1-methyl-5-nitro-1H-benzo[d]imidazole-2(3H)-one (0.16 g, 0.83 mmol) in anhydrous methanol (2.5 mL), add zinc powder (0.54 g, 8.3 mmol) and ammonium chloride (0.22, 4.2 mmol), heat to 50° C., and stir for 3 h. Filter the reaction solution with vacuum, rinse the filter cake twice with absolute ethanol (2 mL each time), combine the filtrate, and concentrate with vacuum, add water (10 mL) to the concentrate, extract with dichloromethane for three times (5 mL each time), combine the organic layer, wash once with water and saturated salt solution respectively, dry with anhydrous sodium sulfate, filter and concentrate with vacuum to obtain the title compound (0.12 g, 87%). ESI-QQQ-MS: m/z 164 $[M+H]^+$.

(Step 4) 5-(dimethylamino)-1-methyl-1H-benzo[d]imidazole-2(3H)-one (P-32)

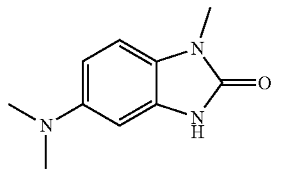

Dissolve 5-amino-1-methyl-1H-benzo[d]imidazole-2(3H)-one (0.12 g, 0.73 mmol) in anhydrous DMF (3 mL), add sodium hydrogen (0.07 g, 2.9 mmol), stir for 0.5 h, then add iodomethane (0.26 g, 1.8 mmol), react at room temperature for 12 h. Concentrate the reaction system with vacuum and add water (10 mL) to the reaction system, extract with ethyl acetate twice (5 mL each time), combine organic phase, wash with saturated salt solution once, dry with anhydrous sodium sulfate, filter and concentrate with vacuum, and purify the concentrate by silica gel column chromatography (dichloromethane/methanol=10:1) to obtain the title compound (0.06 g, 40%). ESI-QQQ-MS: m/z 192 $[M+H]^+$.

Intermediate Preparation Example 33: Synthesis of 6-(dimethylamino)-1-methyl-1H-benzo[d]imidazole-2(3H)-one (P-33)

(Step 1) 1-methyl-6-nitro-1H-benzo[d]imidazole-2(3H)-one

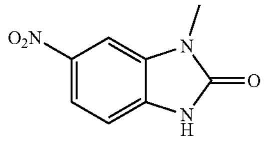

Dissolve $N^1$-methyl-5-nitrobenzene-1,2-diamine (0.33 g, 2 mmol) in dichloromethane (4 mL), cool to 0° C., add triethylamine (0.14 g, 2.6 mmol), and slowly add triphosgene/dichloromethane solution (0.24 g/1 mL) dropwise to the reaction system, and react at room temperature for 1 h. Concentrate the reaction solution with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum, and purify the concentrate with silica gel column chromatography (dichloromethane/methanol=20:1) to obtain the title compound (0.23 g, 60%). ESI-QQQ-MS: m/z 194 $[M+H]^+$.

(Step 2) 6-amino-1-methyl-1H-benzo[d]imidazole-2(3H)-one

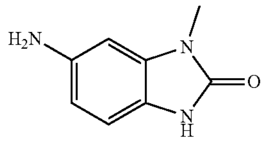

Dissolve 1-methyl-6-nitro-1H-benzo[d]imidazole-2(3H)-one (0.23 g, 1.2 mmol) in anhydrous methanol (4.5 mL), add zinc powder (0.91 g, 12 mmol) and ammonium chloride (0.37 g, 6 mmol), heat to 50° C. and stir for 3 h. Filter the reaction solution with vacuum, rinse the filter cake twice with absolute ethanol (2 mL each time), combine the filtrate, and concentrate with vacuum, add water (20 mL) to the concentrate, extract with dichloromethane for three times (10 mL each time), combine the organic layer, wash once with water and saturated salt solution respectively, dry with anhydrous sodium sulfate, filter and concentrate with vacuum to obtain the title compound (0.16 g, 81%). ESI-QQQ-MS: m/z 164 $[M+H]^+$.

(Step 3) 6-(dimethylamino)-1-methyl-1H-benzo[d]imidazole-2(3H)-one (P-33)

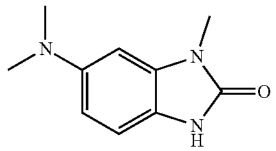

Dissolve 6-amino-1-methyl-1H-benzo[d]imidazole-2(3H)-one (0.16 g, 0.98 mmol) in anhydrous DMF (3 mL), add sodium hydrogen (0.1 g, 4 mmol), stir for 0.5 h, and add iodomethane (0.36 g, 2.5 mmol), react at room temperature for 12 h. Concentrate the reaction system with vacuum and add water (20 mL) to the reaction system, extract with ethyl acetate twice (10 mL each time), combine organic phase, wash with saturated salt solution once, dry with anhydrous sodium sulfate, filter and concentrate with vacuum, and purify the concentrate by silica gel column chromatography (dichloromethane/methanol=10:1) to obtain the title compound (0.08 g, 42%). ESI-QQQ-MS: m/z 192 $[M+H]^+$.

Intermediate Preparation Example 34: Synthesis of 2,4,6-trichlorobenzoyl chloride (P-34)

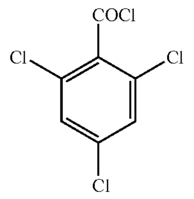 [SMILES: O=C(Cl)c1c(Cl)cc(Cl)cc1Cl]

Dissolve 2,4,6-trichlorobenzoic acid (0.23 g, 1 mmol) in 5 mL of dichloromethane, add thionyl chloride (0.24 g, 2 mmol) and DMF (3 drops), and react at room temperature for 3 h. Concentrate the reaction solution with vacuum to obtain the title compound and directly use in the next reaction.

Intermediate Preparation Example 35: Synthesis of 2,6-dichloro-4-(diethylamino) benzoyl chloride (P-35)

(Step 1) methyl 4-bromo-2,6-dichlorobenzoate

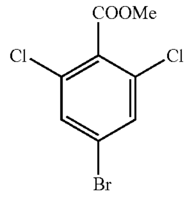 [SMILES: COC(=O)c1c(Cl)cc(Br)cc1Cl]

Dissolve 4-bromo-2,6-dichlorobenzoic acid (0.27 g, 1 mmol) in 5 mL of methanol, cool to 0° C., and add thionyl chloride (0.24 g, 2 mmol) to the reaction system and react at room temperature for 3 h. Concentrate the reaction solution with vacuum, add ethyl acetate (5 mL) and saturated sodium bicarbonate solution (10 mL), stand for layering, wash the organic layer with saturated salt solution once, dry with anhydrous sodium sulfate, filter and concentrate with vacuum, and purify the concentrate by silica gel column chromatography (petroleum ether/ethyl acetate=5:1) to obtain the title compound (0.24 g, 85%). ESI-QQQ-MS: m/z 283 $[M+H]^+$.

(Step 2) methyl 2,6-dichloro-4-(diethylamino)benzoate

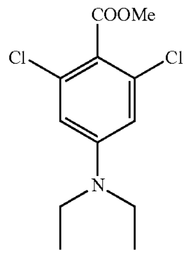 [SMILES: CCN(CC)c1cc(Cl)c(C(=O)OC)c(Cl)c1]

Mix methyl 4-bromo-2,6-dichlorobenzoate (0.24 g, 0.85 mmol), diethylamine (0.12 g, 1.7 mmol), palladium (II) acetate (10 mg, 5 mol %). (±)-2,2'-bis-(diphenylphosphino)-1,1'-binaphthyl (63 mg, 10 mol %), cesium carbonate (0.3 g, 0.92 mmol) and anhydrous dioxane (6 mL), displace nitrogen, and react in microwave at 120° C. for 2 h. Filter the reaction solution with purified siliceous earths, concentrate the filtrate with vacuum, add water (10 mL), extract with ethyl acetate twice (5 mL each time), combine the organic layer, wash with saturated salt solution once, dry with anhydrous sodium sulfate, filter and concentrate with vacuum, and purify the concentrate by silica gel column chromatography (petroleum ether/ethyl acetate=2:1) to obtain the title compound (0.16 g, 70%). ESI-QQQ-MS: m/z 276 $[M+H]^+$.

(Step 3) 2,6-dichloro-4-(diethylamino)benzoyl chloride (P-35)

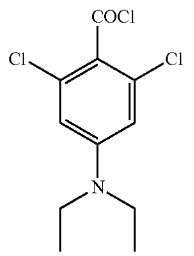 [SMILES: CCN(CC)c1cc(Cl)c(C(=O)Cl)c(Cl)c1]

Dissolve methyl 2,6-dichloro-4-(diethylamino)benzoate (0.16 g, 0.58 mmol) in methanol (3 mL) and water (0.5 mL), and add 6N sodium hydroxide solution (0.15 mL, 0.87 mmol) and react at room temperature for 24 h. Adjust the reaction solution to 5-6 with 2N hydrochloric acid, filter and wash the filter cake 3 times, dry with vacuum, dissolve the dried solid in 3 mL of dichloromethane, add thionyl chloride (0.13 g, 1.1 mmol) and DMF (2 drops), and react at room temperature for 4 h. Concentrate the reaction solution with vacuum to obtain the title compound and directly use in the next reaction.

Intermediate Preparation Example 36: Synthesis of 2,6-dichloro-4-morpholinobenzoyl chloride (P-36)

(Step 1) methyl 2,6-dichloro-4-morpholinobenzoate

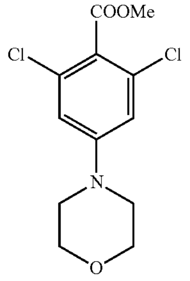 [SMILES: COC(=O)c1c(Cl)cc(N2CCOCC2)cc1Cl]

Mix methyl 4-bromo-2,6-dichlorobenzoate (0.24 g, 0.85 mmol), morpholine (0.1 g, 1.2 mmol), palladium (II) acetate (10 mg, 5 mol %), (±)-2,2'-bis-(diphenylphosphino)-1,1'-binaphthyl (63 mg, 10 mol %), cesium carbonate (0.3 g, 0.92 mmol) and anhydrous dioxane (6 mL), displace nitrogen and react in microwave at 120° C. for 2 h. Filter the reaction solution with purified siliceous earths, concentrate the filtrate with vacuum, add water (10 mL), extract with ethyl acetate twice (5 mL each time), combine the organic layer, wash with saturated salt solution once, dry with anhydrous sodium sulfate, filter and concentrate with vacuum, and purify the concentrate by silica gel column chromatography (petroleum ether/ethyl acetate=2:1) to obtain the title compound (0.18 g, 74%). ESI-QQQ-MS: m/z 290 $[M+H]^+$.

(Step 2) 2,6-dichloro-4-morpholinobenzoyl chloride (P-36)

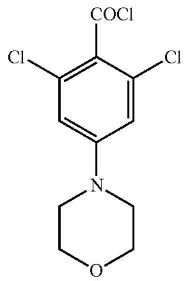 [SMILES: O=C(Cl)c1c(Cl)cc(N2CCOCC2)cc1Cl]

Dissolve methyl 2,6-dichloro-4-morpholinobenzoate (0.18 g, 0.62 mmol) in methanol (3 mL) and water (0.5 mL), add 6N sodium hydroxide solution (0.16 mL, 0.93 mmol) and react at room temperature for 24 h. Adjust the reaction solution to 5-6 with 2N hydrochloric acid, filter and wash the filter cake 3 times, dry with vacuum, dissolve the dried solid in 3 mL of dichloromethane, add thionyl chloride (0.14 g, 1.2 mmol) and DMF (2 drops), and react at room temperature for 4 h. Concentrate the reaction solution with vacuum to obtain the title compound and directly use in the next reaction.

Intermediate Preparation Example 37: Synthesis of 4-(2-oxa-5-azadicyclo[2.2.1]heptan-5-yl)-2,6-dichlorobenzoyl chloride (P-37)

(Step 1) Methyl 4-(2-oxa-5-azadicyclo[2.2.1]heptan-5-yl)-2,6-dichlorobenzoate

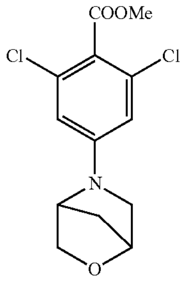 [SMILES: COC(=O)c1c(Cl)cc(N2CC3CC2CO3)cc1Cl]

Mix methyl 4-bromo-2,6-dichlorobenzoate (0.24 g, 0.85 mmol), 2-oxa-5-azabicyclo[2.2.1]heptan (0.12 g, 1.2 mmol), palladium (II) acetate (10 mg, 5 mol %), (±)-2,2'-bis-(diphenylphosphino)-1,1'-binaphthyl (63 mg, 10 mol %), cesium carbonate (0.3 g, 0.92 mmol) and anhydrous dioxane (6 mL), displace nitrogen, and react in microwave at 120° C. for 2 h. Filter the reaction solution with purified siliceous earths, concentrate the filtrate with vacuum, add water (10 mL), extract with ethyl acetate twice (5 mL each time), combine the organic layer, wash with saturated salt solution once, dry with anhydrous sodium sulfate, filter and concentrate with vacuum, and purify the concentrate by silica gel column chromatography (petroleum ether/ethyl acetate=2:1) to obtain the title compound (0.2 g, 78%). ESI-QQQ-MS: m/z 302 $[M+H]^+$.

(Step 2) 4-(2-oxa-5-azadicyclo[2.2.1]hept-5-yl)-2,6-dichlorobenzoyl chloride (P-37)

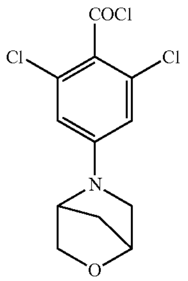 [SMILES: O=C(Cl)c1c(Cl)cc(N2CC3CC2CO3)cc1Cl]

Dissolve methyl 4-(2-oxa-5-azabicyclo[2.2.1]heptan-5-yl)-2,6-dichlorobenzoate (0.2 g, 0.66 mmol) in methanol (3 mL) and water (0.5 mL), add 6N sodium hydroxide solution (0.17 mL, 0.99 mmol) and react at room temperature for 24 h. Adjust the reaction solution to 5-6 with 2N hydrochloric acid, filter and wash the filter cake 3 times, dry with vacuum, dissolve the dried solid in 3 mL of dichloromethane, add thionyl chloride (0.15 g, 1.3 mmol) and DMF (2 drops), and react at room temperature for 4 h. Concentrate the reaction solution with vacuum to obtain the title compound and directly use in the next reaction.

Intermediate Preparation Example 38: Synthesis of 2,6-dichloro-4-(4-morpholinopiperidin-1-yl)benzoyl chloride (P-38)

(Step 1) Methyl 2,6-dichloro-4-(4-morpholinopiperidin-1-yl)benzoate

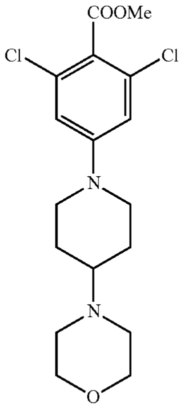 [SMILES: COC(=O)c1c(Cl)cc(N2CCC(N3CCOCC3)CC2)cc1Cl]

Mix methyl 4-bromo-2,6-dichlorobenzoate (0.24 g, 0.85 mmol), 4-(piperidin-4-yl)morpholine (0.2 g, 1.2 mmol), palladium (II) acetate (10 mg, 5 mol %), (±)-2,2'-bis-(diphenylphosphino)-1,1'-binaphthyl (63 mg, 10 mol %), cesium carbonate (0.3 g, 0.92 mmol) and anhydrous dioxane (6 mL), displace nitrogen, and react in microwave reaction at 120° C. for 2 h. Filter the reaction solution with purified siliceous earths, concentrate the filtrate with vacuum, add water (10 mL), extract with ethyl acetate twice (5 mL each time), combine the organic layer, wash with saturated salt solution once, dry with anhydrous sodium sulfate, filter and concentrate with vacuum, and purify the concentrate by silica gel column chromatography (petroleum ether/ethyl acetate=2:1) to obtain the title compound (0.23 g, 72%). ESI-QQQ-MS: m/z 373 $[M+H]^+$.

(Step 2) 2,6-dichloro-4-(4-morpholinopiperidin-1-yl)benzoyl chloride (P-38)

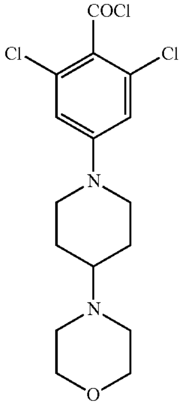 [SMILES: O=C(Cl)c1c(Cl)cc(N2CCC(N3CCOCC3)CC2)cc1Cl]

Dissolve methyl 2,6-dichloro-4-(4-morpholinopiperidin-1-yl)benzoate (0.23 g, 0.62 mmol) in methanol (3 mL) and water (0.5 mL), add 6N sodium hydroxide solution (0.16 mL, 0.93 mmol) and react at room temperature for 241. Adjust the reaction solution to 5-6 with 2N hydrochloric acid, filter and wash the filter cake 3 times, dry with vacuum, dissolve the dried solid in 3 mL of dichloromethane, add thionyl chloride (0.14 g, 1.2 mmol) and DMF (2 drops), and react at room temperature for 4 h. Concentrate the reaction solution with vacuum to obtain the title compound and directly use in the next reaction.

Example 1: Synthesis of Compound 1

Step 1

(S)-3-(4-(5',6'-difluoro-2'-oxospiro[cyclopropane-1,3'-indoline]-1'-yl)phenyl)-2-(triphenylamino)methyl propionate

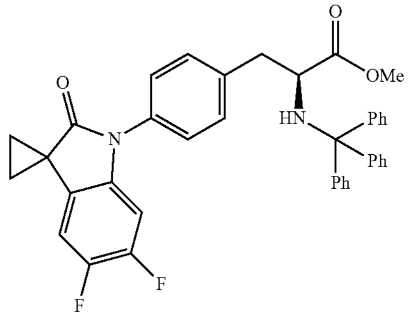 [SMILES: COC(=O)[C@H](Cc1ccc(N2C(=O)C3(CC3)c3cc(F)c(F)cc32)cc1)NC(c1ccccc1)(c1ccccc1)c1ccccc1]

Dissolve P-10 (98 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 361. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (215 mg, 70%). ESI-QQQ-MS: m/z 615 $[M+H]^+$.

Step 2

(S)-2-amino-3-(4-(5',6'-difluoro-2'-oxospiro[cyclopropane-1,3'-indoline]-1'-yl)phenyl)methyl propionate

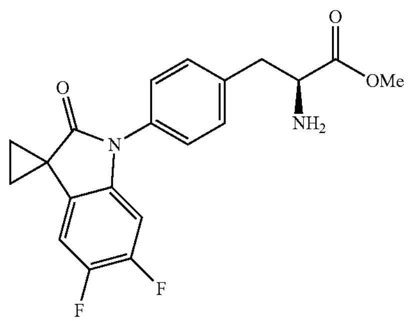 [SMILES: COC(=O)[C@@H](N)Cc1ccc(N2C(=O)C3(CC3)c3cc(F)c(F)cc32)cc1]

Dissolve (S)-3-(4-(5',6'-difluoro-2'-oxospiro[cyclopropane-1,3'-indoline]-1'-yl)phenyl)-2-(triphenylamino)methyl propionate (154 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhdrous sodium sulfate, filter and concentrate with vacuum to obtain the title compound (86 mg, 92%). ESI-QQQ-MS: m/z 373 $[M+H]^+$.

Step 3

(S)-2-(2-chloro-6-fluorobenzamide)-3-(4-(5',6'-difluoro-2'-oxospiro[cyclopropane-1,3'-indoline]-1'-phenyl)methyl propionate

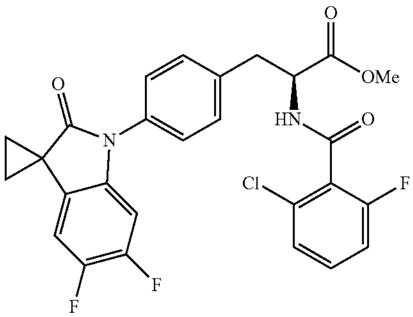 [SMILES: COC(=O)[C@H](Cc1ccc(N2C(=O)C3(CC3)c3cc(F)c(F)cc32)cc1)NC(=O)c1c(F)cccc1Cl]

Dissolve (S)-2-amino-3-(4-(5',6'-difluoro-2'-oxospiro[cyclopropane-1,3'-indoline]-1'-yl)phenyl)methyl propionate (86 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (107 mg, 88%). ESI-QQQ-MS: m/z 529 $[M+H]^+$.

Step 4

(S)-2-(2-chloro-6-fluorobenzamide)-3-(4-(5',6'-difluoro-2'-oxospirino[cyclopropane-1,3'-indoline]-1'-yl)phenyl)propionic acid

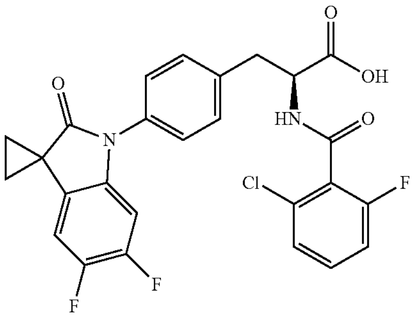 [SMILES: O=C(N[C@@H](Cc1ccc(N2C(=O)C3(CC3)c3cc(F)c(F)cc32)cc1)C(=O)O)c1c(F)cccc1Cl]

Dissolve (S)-2-(2-chloro-6-fluorobenzoylamino)-3-(4-(5',6'-difluoro-2'-oxospiro[cyclopropane-1,3'-indoline]-1'-phenyl)methyl propionate (90 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (57 mg, 65%). ESI-QQQ-MS: m/z 515 $[M+H]^+$. $^1H$ NMR (500 MHz, DMSO-d6): δ 12.90 (brs, 1H), 9.16 (d, J=8.3 Hz, 1H), 7.50-7.42 (m, 3H), 7.39-7.28 (m, 4H), 7.24 (t, J=8.6 Hz, 1H), 6.74-6.70 (m, 1H), 4.77-4.72 (m, 1H), 3.25 (dd, J=14.0, 4.4 Hz, 1H), 3.00 (dd, J=13.9, 10.5 Hz, 1H), 1.79-1.77 (m, 2H), 1.66-1.63 (m, 2H).

Example 2: Synthesis of Compound 2

Step 1

(S)-3-(4-(7'-chloro-2'-oxospiro[cyclopropane-1,3'-indolinyl]-1'-yl)phenyl)-2-(tritylamino)methyl propionate

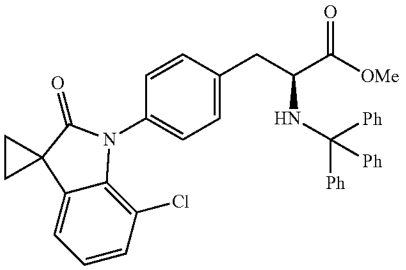 [SMILES: COC(=O)[C@H](Cc1ccc(N2C(=O)C3(CC3)c3cccc(Cl)c32)cc1)NC(c1ccccc1)(c1ccccc1)c1ccccc1]

Dissolve P-6 (97 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 361. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (178 mg, 58%). ESI-QQQ-MS: m/z 613 $[M+H]^+$.

Step 2

(S)-2-amino-3-(4-(7'-chloro-2'-oxospiro[cyclopropane-1,3'-indoline]-1'-yl)phenyl)methyl propionate

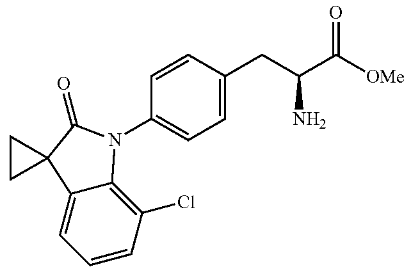 [SMILES: COC(=O)[C@@H](N)Cc1ccc(N2C(=O)C3(CC3)c3cccc(Cl)c32)cc1]

Dissolve (S)-3-(4-(7'-chloro-2'-oxospiro[cyclopropane-1,3'-indoline]-1'-yl)phenyl)-2-(triphenylmethylamino)methyl propionate (153 mg, 0.25 mmol) in dichloromethane (2 mL), add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhdrous sodium sulfate, filter and concentrate with vacuum to obtain the title compound (83 mg, 90%). ESI-QQQ-MS: m/z 371 $[M+H]^+$.

Step 3

(S)-3-(4-(7'-chloro-2'-oxospiro[cyclopropane-1,3'-indoline]-1'-yl)phenyl)-2-(2-chloro-6-fluorobenzamide) methyl propionate

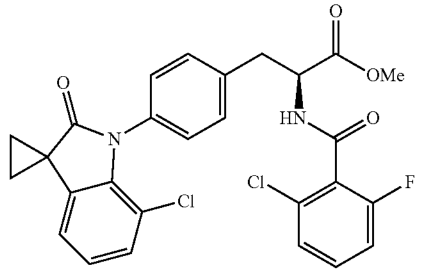 [SMILES: COC(=O)[C@H](Cc1ccc(N2C(=O)C3(CC3)c3cccc(Cl)c32)cc1)NC(=O)c1c(F)cccc1Cl]

Dissolve (S)-2-amino-3-(4-(7'-chloro-2'-oxospiro[cyclopropane-1,3'-indoline]-1'-yl)phenyl)methyl propionate (85 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (112 mg, 92%). ESI-QQQ-MS: m/z 527 $[M+H]^+$.

Step 4

(S)-3-(4-(7'-chloro-2'-oxospiro[cyclopropane-1,3'-indoline]-1'-yl)phenyl)-2-(2-chloro-6-fluorobenzamide) propionic acid

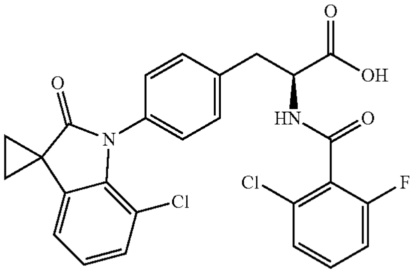 [SMILES: O=C(N[C@@H](Cc1ccc(N2C(=O)C3(CC3)c3cccc(Cl)c32)cc1)C(=O)O)c1c(F)cccc1Cl]

Dissolve (S)-3-(4-(7'-chloro-2'-oxospiro[cyclopropane-1,3'-indoline]-1'-yl)phenyl)-2-(2-chloro-6-fluorobenzamide) methyl propionate (90 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (55 mg, 63%). ESI-QQQ-MS: m/z 513 $[M+H]^+$. $^1H$ NMR (500 MHz, DMSO-d6): δ 12.84 (brs, 1H), 9.19 (d, J=8.1 Hz, 1H), 7.47-7.40 (m, 3H), 7.33-7.23 (m, 4H), 7.19-7.17 (m, 1H), 7.08-7.02 (m, 2H), 4.72-4.67 (m, 1H), 3.22 (dd, J=14.1, 4.3 Hz, 1H), 3.01 (dd, J=14.1, 10.3 Hz, 1H), 1.78-1.76 (m, 2H), 1.68-1.66 (m, 2H).

Example 3: Synthesis of Compound 4

Step 1

(S)-3-(4-(7'-methoxy-2'-oxospiro[cyclopropane-1,3'-indoline]-1'-yl)phenyl)-2-(triphenylamino)methyl propionate

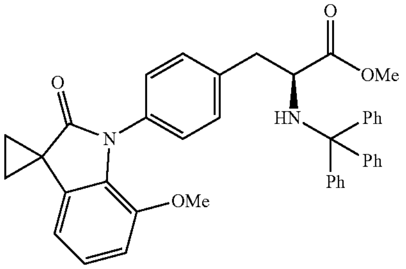 [SMILES: COC(=O)[C@H](Cc1ccc(N2C(=O)C3(CC3)c3cccc(OC)c32)cc1)NC(c1ccccc1)(c1ccccc1)c1ccccc1]

Dissolve P-9 (95 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol) to reaction system, under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (188 mg, 62%). ESI-QQQ-MS: m/z 609 $[M+H]^+$.

Step 2

(S)-2-amino-3-(4-(7-methoxy-2'-oxospiro[cyclopropane-1,3'-indoline]-1'-yl)phenyl)methyl propionate

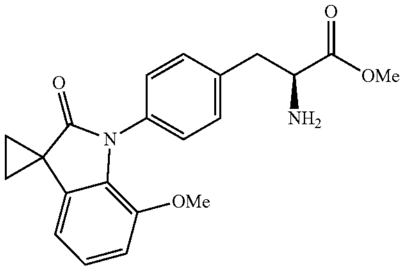 [SMILES: COC(=O)[C@@H](N)Cc1ccc(N2C(=O)C3(CC3)c3cccc(OC)c32)cc1]

Dissolve (S)-3-(4-(7'-methoxy-2-oxospiro[cyclopropane-1,3'-indoline]-1'-yl)phenyl)-2-(triphenylamino)methyl propionate (152 mg, 0.25 mmol) in dichloromethane (2 mL), add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (83 mg, 91%). ESI-QQQ-MS: m/z 367 $[M+H]^+$.

Step 3

(S)-2-(2,6-dichlorobenzamido)-3-(4-(7'-methoxy-2'-oxospiro[cyclopropane-1,3'-indoline]-1'-yl)phenyl) methyl propionate

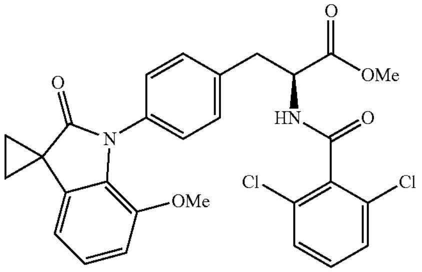 [SMILES: COC(=O)[C@H](Cc1ccc(N2C(=O)C3(CC3)c3cccc(OC)c32)cc1)NC(=O)c1c(Cl)cccc1Cl]

Dissolve (S)-2-amino-3-(4-(7'-methoxy-2'-oxospiro[cyclopropane-1,3'-indoline]-1'-yl)phenyl)methyl propionate (83 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (109 mg, 88%). ESI-QQQ-MS: m/z 539 $[M+H]^+$.

Step 4

(S)-2-(2,6-dichlorobenzamido)-3-(4-(7'-methoxy-2'-oxospiro[cyclopropane-1,3'-indoline]-1'-yl)phenyl) propionic acid

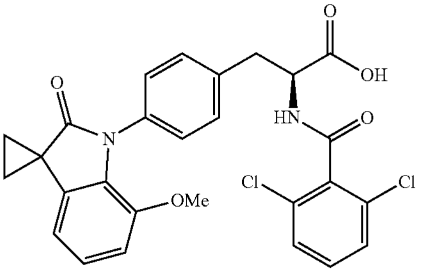 [SMILES: COc1cccc2c1N(c1ccc(C[C@H](NC(=O)c3c(Cl)cccc3Cl)C(=O)O)cc1)C(=O)C21CC1]

Dissolve (S)-2-(2,6-dichlorobenzamido)-3-(4-(7'-methoxy-2'-oxospiro[cyclopropane-1,3'-indoline]-1'-yl)phenyl)methyl propionate (92 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 ml each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (52 mg, 59%). ESI-QQQ-MS: m/z 525 $[M+H]^+$. $^1H$ NMR (500 MHz, DMSO-d6): δ 12.74 (brs, 1H), 9.15 (d, J=8.2 Hz, 1H), 7.46-7.32 (m, 5H), 7.19 (d, J=8.2 Hz, 2H), 7.02 (t, J=7.9 Hz, 1H), 6.91 (d, J=8.2 Hz, 1H), 6.71 (d, J=7.4 Hz, 1H), 4.74-4.69 (m, 1H), 3.46 (s, 3H), 3.19 (dd, J=14.0, 4.7 Hz, 1H), 2.99 (dd, J=14.0, 9.8 Hz, 1H), 1.68-1.64 (m, 2H), 1.62-1.58 (m, 2H).

Example 4: Synthesis of Compound 6

Step 1

(S)-3-(4-(6'-fluoro-2'-oxospiro[cyclopropane-1,3'-indoline]-1'-yl)phenyl)-2-(triphenylamino)methyl propionate

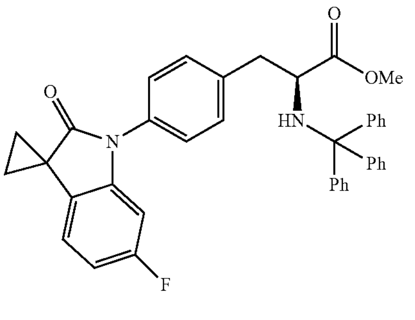 [SMILES: COC(=O)[C@H](Cc1ccc(N2C(=O)C3(CC3)c3ccc(F)cc32)cc1)NC(c1ccccc1)(c1ccccc1)c1ccccc1]

Dissolve P4 (89 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (202 mg, 68%). ESI-QQQ-MS: m/z 597 $[M+H]^+$.

Step 2

(S)-2-amino-3-(4-(6'-fluoro-2'-oxospiro[cyclopropane-1,3'-indoline]-1'-yl)phenyl)methyl propionate

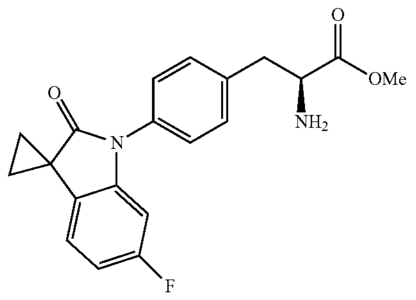 [SMILES: COC(=O)[C@@H](N)Cc1ccc(N2C(=O)C3(CC3)c3ccc(F)cc32)cc1]

Dissolve (S)-3-(4-(6'-fluoro-2'-oxospiro[cyclopropane-1,3'-indoline]-1'-yl)phenyl)-2-(triphenylamino)methyl propionate (149 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (84 mg, 95%). ESI-QQQ-MS: m/z 355 $[M+H]^+$.

Step 3

(S)-2-(2,6-dichlorobenzamido)-3-(4-(6'-fluoro-2'-oxospiro[cyclopropane-1,3'-indoline]-1'-yl)phenyl) methyl propionate

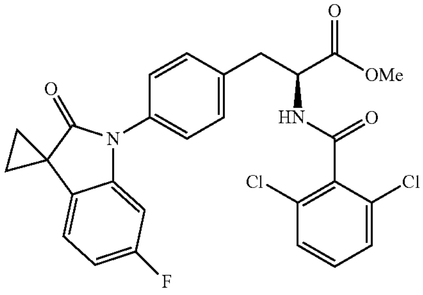 [SMILES: COC(=O)[C@H](Cc1ccc(N2C(=O)C3(CC3)c3ccc(F)cc32)cc1)NC(=O)c1c(Cl)cccc1Cl]

Dissolve methyl (S)-2-amino-3-(4-(6'-fluoro-2'-oxospiro[cyclopropane-1,3'-indoline]-1'-yl)phenyl)propionate (84 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (108 mg, 89%). ESI-QQQ-MS: m/z 527 $[M+H]^+$.

Step 4

(S)-2-(2,6-dichlorobenzamido)-3-(4-(6'-fluoro-2'-oxospiro[cyclopropane-1,3'-indoline]-1'-yl)phenyl) propionic acid

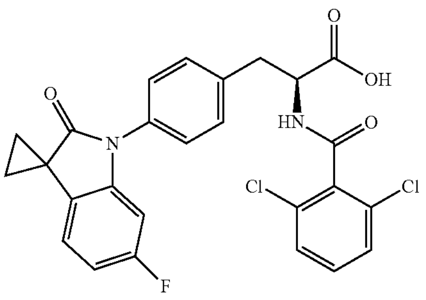 [SMILES: O=C(N[C@@H](Cc1ccc(N2C(=O)C3(CC3)c3ccc(F)cc32)cc1)C(=O)O)c1c(Cl)cccc1Cl]

Dissolve (S)-2-(2,6-dichlorobenzamido)-3-(4-(6'-fluoro-2'-oxospiro[cyclopropane-1,3'-indoline]-1'-yl)phenyl) methyl propionate (90 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 ml each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (48 mg, 55%). ESI-QQQ-MS: m/z 513 $[M+H]^+$. $^1H$ NMR (500 MHz, DMSO-d6): δ 12.75 (brs, 1H), 9.13 (d, J=8.4 Hz, 1H), 7.51-7.49 (m, 2H), 7.45-7.32 (m, 5H), 7.15-7.13 (m, 1H), 6.93-6.79 (m, 1H), 6.53-6.51 (m, 1H), 4.83-4.71 (m, 1H), 3.25 (dd, J=14.0, 4.3 Hz, 1H), 2.99 (dd, J=13.9, 10.7 Hz, 1H), 1.75-1.71 (m, 2H), 1.64-1.60 (m, 2H).

Example 5: Synthesis of Compound 7

(Step 1) (S)-3-(4-(7'-fluoro-2'-oxospiro [cyclopropane-1,3'-indoline]-1'-yl)phenyl)-2-(triphenylamino) methyl propionate

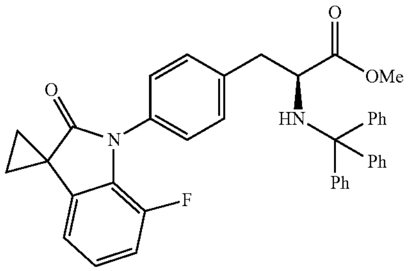 [SMILES: COC(=O)[C@H](Cc1ccc(N2C(=O)C3(CC3)c3cccc(F)c32)cc1)NC(c1ccccc1)(c1ccccc1)c1ccccc1]

Dissolve P-3 (89 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (182 mg, 61%). ESI-QQQ-MS: m/z 597 $[M+H]^+$.

Step 2

(S)-2-amino-3-(4-(7'-fluoro-2'-oxospiro[cyclopropane-1,3'-indoline]-1'-yl)phenyl)methyl propionate

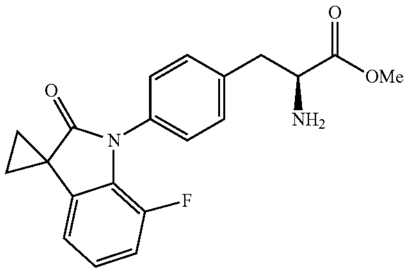 [SMILES: COC(=O)[C@@H](N)Cc1ccc(N2C(=O)C3(CC3)c3cccc(F)c32)cc1]

Dissolve (S)-3-(4-(7'-fluoro-2'-oxospiro[cyclopropane-1,3'-indoline]-1'-yl)phenyl)-2-(triphenylamino)methyl propionate (149 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (85 mg, 96%). ESI-QQQ-MS: m/z 355 $[M+H]^+$.

Step 3

(S)-2-(2,6-dichlorobenzamido)-3-(4-(7'-fluoro-2'-oxospiro[cyclopropane-1,3'-indoline]-1'-yl)phenyl) methyl propionate

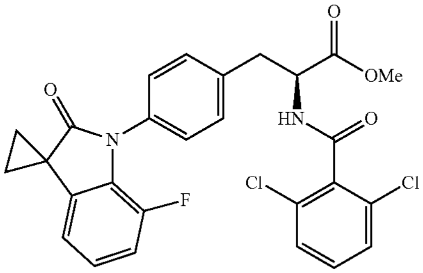 [SMILES: COC(=O)[C@H](Cc1ccc(N2C(=O)C3(CC3)c3cccc(F)c32)cc1)NC(=O)c1c(Cl)cccc1Cl]

Dissolve (S)-2-amino-3-(4-(7'-fluoro-2'-oxospiro[cyclopropane-1,3'-indoline]-1'-yl)phenyl)methyl propionate (84 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (109 mg, 90%). ESI-QQQ-MS: m/z 527 $[M+H]^+$.

Step 4

(S)-2-(2,6-dichlorobenzoylamino)-3-(4-(7'-fluoro-2'-oxospiro[cyclopropane-1,3'-indoline]-1'-yl)phenyl) propionic acid

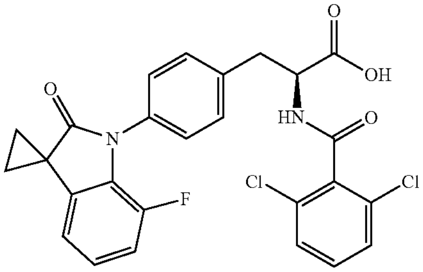 [SMILES: O=C(N[C@@H](Cc1ccc(N2C(=O)C3(CC3)c3cccc(F)c32)cc1)C(=O)O)c1c(Cl)cccc1Cl]

Dissolve (S)-2-(2,6-dichlorobenzamido)-3-(4-(7'-fluoro-2'-oxospiro[cyclopropane-1,3'-indoline]-1'-yl)phenyl) methyl propionate (90 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 ml each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (51 mg, 58%). ESI-QQQ-MS: m/z 513 $[M+H]^+$. $^1H$ NMR (500 MHz, DMSO-d6): δ

12.79 (brs, 1H), 9.15 (d, J=8.3 Hz, 1H), 7.44-7.37 (m, 5H), 7.35-7.31 (m, 2H), 7.11-7.01 (m, 2H), 6.97-6.91 (m, 1H), 4.74-4.72 (m, 1H), 3.22 (dd, J=14.1, 4.3 Hz, 1H), 2.99 (dd, J=14.1, 10.4 Hz, 1H), 1.79-1.74 (m, 2H), 1.69-1.64 (m, 2H).

Example 6: Synthesis of Compound 8

Step 1

(S)-3-(4-(2'-oxospiro[cyclopropane-1,3'-indoline]-1'-yl)phenyl)-2-(triphenylamino)methyl propionate

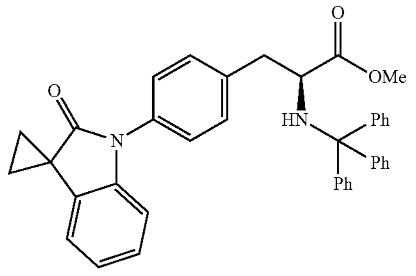 [SMILES: COC(=O)[C@H](Cc1ccc(N2C(=O)C3(CC3)c3ccccc32)cc1)NC(c1ccccc1)(c1ccccc1)c1ccccc1]

Dissolve P-2 (80 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (197 mg, 68%). ESI-QQQ-MS: m/z 579 $[M+H]^+$.

(Step 2) (S)-2-amino-3-(4-(2'-oxospiro[cyclopropane-1,3'-indoline]-1'-yl)phenyl)methyl propionate

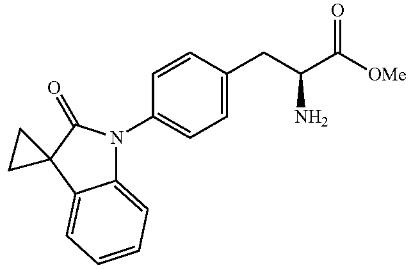 [SMILES: COC(=O)[C@@H](N)Cc1ccc(N2C(=O)C3(CC3)c3ccccc32)cc1]

Dissolve (S)-3-(4-(2'-oxospiro[cyclopropane-1,3'-indoline]-1'-yl)phenyl)-2-(triphenylamino)methyl propionate (145 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (79 mg, 94%). ESI-QQQ-MS: m/z 337 $[M+H]^+$.

Step 3

(S)-2-(2,6-dichlorobenzamido)-3-(4-(2'-oxospiro[cyclopropane-1,3'-indoline]-1'-yl)phenyl)methyl propionate

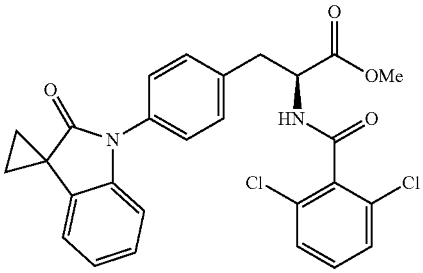 [SMILES: COC(=O)[C@H](Cc1ccc(N2C(=O)C3(CC3)c3ccccc32)cc1)NC(=O)c1c(Cl)cccc1Cl]

Dissolve (S)-2-amino-3-(4-(2'-oxospiro[cyclopropane-1,3'-indoline]-1'-yl)phenyl)methyl propionate (77 mg, 0.23 mmol) and triethylamine (30 mg, 0.3 mmol) in dichloromethane (2 mL), cool to 0° C., add 2-chloro-4-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (111 mg, 95%). ESI-QQQ-MS: m/z 509 $[M+H]^+$.

Step 4

(S)-2-(2,6-dichlorobenzamido)-3-(4-(2'-oxospiro[cyclopropane-1,3'-indoline]-1'-yl)phenyl)propionic acid

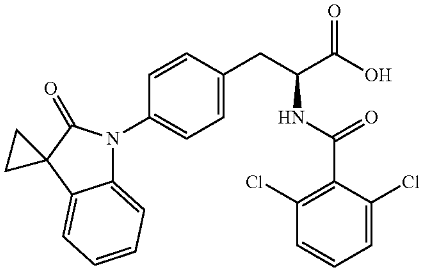 [SMILES: O=C(N[C@@H](Cc1ccc(N2C(=O)C3(CC3)c3ccccc32)cc1)C(=O)O)c1c(Cl)cccc1Cl]

Dissolve (S)-2-(2,6-dichlorobenzamido)-3-(4-(2'-oxospiro[cyclopropane-1,3'-indoline]-1'-yl)phenyl)methyl propionate (87 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (54 mg, 64%). ESI-QQQ-MS: m/z 495 $[M+H]^+$. $^1H$ NMR (500 MHz, DMSO-d6): δ 12.85 (brs, 1H), 9.14 (d, J=8.4 Hz, 1H), 7.51-7.33 (m, 7H), 7.20-7.19 m, 1H), 7.13-7.03 (m, 2H), 6.76 (d, J=7.9 Hz, 1H), 4.78-4.76 (m, 1H), 3.25 (dd, J=14.0, 4.4 Hz, 1H), 3.00 (dd, J=14.0, 10.5 Hz, 1H), 1.73-1.69 (m, 2H), 1.65-1.61 (m, 2H).

Example 7: Synthesis of Compound 9

Step 1

(S)-3-(4-(7-chloro-2-oxo-2',3',5',6'-tetrahydrospiro [indoline-3,4'-pyran]-1-yl)phenyl)-2-(triphenylamino)methyl propionate

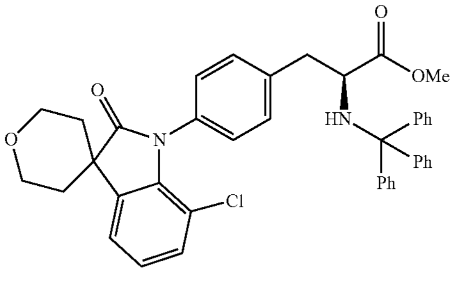 [SMILES: COC(=O)[C@H](Cc1ccc(N2C(=O)C3(CCOCC3)c3cccc(Cl)c32)cc1)NC(c1ccccc1)(c1ccccc1)c1ccccc1]

Dissolve P-14 (119 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (180 mg, 55%). ESI-QQQ-MS: m/z 657 $[M+H]^+$.

Step 2

(S)-2-amino-3-(4-(7-chloro-2-oxo-2',3',5',6'-tetrahydrospiro[indoline-3,4'-pyran]-1-phenyl)methyl propionate

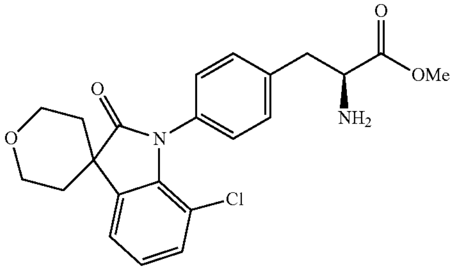 [SMILES: COC(=O)[C@@H](N)Cc1ccc(N2C(=O)C3(CCOCC3)c3cccc(Cl)c32)cc1]

Dissolve (S)-3-(4-(7-chloro-2-oxo-2',3',5',6'-tetrahydrospiro[indoline-3,4'-pyran]-1-yl)phenyl)methyl propionate (164 mg, 0.25 mmol) in dichloromethane (2 mL), add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (98 mg, 95%). ESI-QQQ-MS: m/z 415 $[M+H]^+$.

Step 3

(S)-3-(4-(7-chloro-2-oxo-2',3',5',6'-tetrahydrospiro [indoline-3,4'-pyran]-1-yl)phenyl)-2-(2-chloro-6-fluorobenzoylamino)methyl propionate

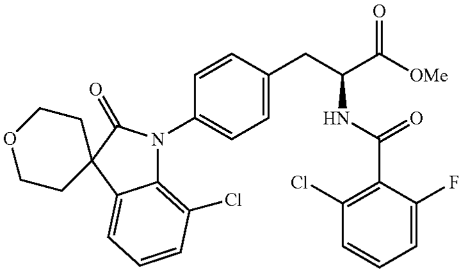 [SMILES: COC(=O)[C@H](Cc1ccc(N2C(=O)C3(CCOCC3)c3cccc(Cl)c32)cc1)NC(=O)c1c(F)cccc1Cl]

Dissolve (S)-2-amino-3-(4-(7-chloro-2-oxo-2',3',5',6'-tetrahydrospiro[indoline-3,4'-pyran]-1-phenyl)methyl propionate (95 mg, 0.23 mmol) and triethylamine (30 mg, 0.3 mmol) in dichloromethane (2 mL), cool to 0° C., and add 2-chloro-6-fluorobenzoyl chloride (48 mg, 0.25 mmol), react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (118 mg, 90%). ESI-QQQ-MS: m/z 571 $[M+H]^+$.

Step 4

(S)-3-(4-(7-chloro-2-oxo-2',3',5',6'-tetrahydrospiro [indoline-3,4'-pyran]-1-yl)phenyl)-2-(2-chloro-6-fluorobenzamide)propionic acid

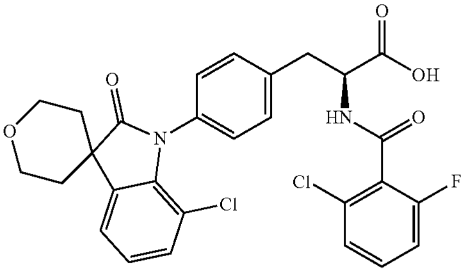 [SMILES: O=C(N[C@@H](Cc1ccc(N2C(=O)C3(CCOCC3)c3cccc(Cl)c32)cc1)C(=O)O)c1c(F)cccc1Cl]

Dissolve (S)-3-(4-(7-chloro-2-oxo-2',3',5',6'-tetrahydrospiro[indoline-3,4'-pyran]-1-yl)phenyl)-2-(2-chloro-6-fluorobenzoylamino) methyl propionate (97 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O$/$CH_3CN$ system containing 0.1% formic acid) to obtain the title compound (54 mg, 57%). ESI-QQQ-MS: m/z 557 $[M+H]^+$. $^1H$ NMR (500 MHz, DMSO-d6): δ 12.87 (brs, 1H), 9.15 (d, J=8.0 Hz, 1H), 7.55 (d, J=7.4 Hz, 1H), 7.47-7.36 (m, 3H), 7.31-7.21 (m, 5H), 7.09 (d, J=7.8 Hz, 1H), 4.70-4.65 (m, 1H), 4.06 (t, J=10.6 Hz, 2H), 3.87-3.79 (m, 2H), 3.22 (dd, J=14.1, 4.3 Hz, 1H), 3.01 (dd, J=14.0, 10.1 Hz, 1H), 2.00-1.93 (m, 2H), 1.87-1.83 (m, 2H).

Example 8: Synthesis of Compound 10

Step 1

(S)-3-(4-(6'-chloro-5'-fluoro-2'-oxospiro[cyclopropane-1,3'-indoline]-1'-yl)phenyl)-2-(triphenylamino) methyl propionate

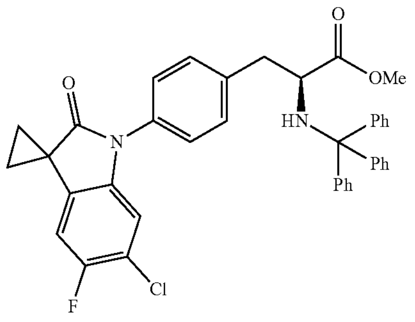 [SMILES: COC(=O)[C@H](Cc1ccc(N2C(=O)C3(CC3)c3cc(F)c(Cl)cc32)cc1)NC(c1ccccc1)(c1ccccc1)c1ccccc1]

Dissolve P-11 (112 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (211 mg, 67%). ESI-QQQ-MS: m/z 631 $[M+H]^+$.

Step 2

(S)-2-amino-3-(4-(6'-chloro-5'-fluoro-2'-oxospiro[cyclopropane-1,3'-indoline]-1'-yl)phenyl)methyl propionate

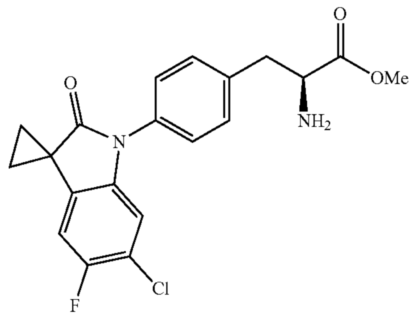 [SMILES: COC(=O)[C@@H](N)Cc1ccc(N2C(=O)C3(CC3)c3cc(F)c(Cl)cc32)cc1]

Dissolve (S)-3-(4-(6'-chloro-5'-fluoro-2'-oxospiro[cyclopropane-1,3'-indoline]-1'-yl)phenyl)-2-(triphenylamino) methyl propionate (158 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (89 mg, 92%). ESI-QQQ-MS: m/z 389 $[M+H]^+$.

Step 3

(S)-3-(4-(6'-chloro-5'-fluoro-2'-oxospiro[cyclopropane-1,3'-indoline]-1'-yl)phenyl)-2-(2-chloro-6-fluorobenzoylamino)methyl propionate

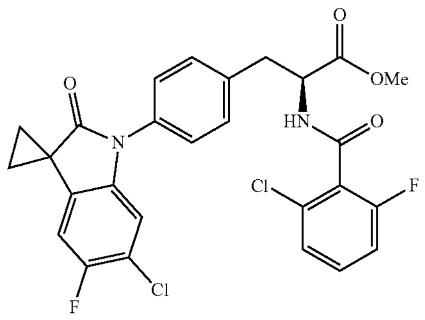 [SMILES: COC(=O)[C@H](Cc1ccc(N2C(=O)C3(CC3)c3cc(F)c(Cl)cc32)cc1)NC(=O)c1c(F)cccc1Cl]

Dissolve (S)-2-amino-3-(4-(6'-chloro-5'-fluoro-2'-oxospiro[cyclopropane-1,3'-indoline]-1'-yl)phenyl)methyl propionate (89 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (113 mg, 90%). ESI-QQQ-MS: m/z 545 $[M+H]^+$.

Step 4

(S)-3-(4-(6'-chloro-5'-fluoro-2'-oxospiro[cyclopropane-1,3'-indoline]-1'-yl)phenyl)-2-(2-chloro-6-fluorobenzamide)propionic acid

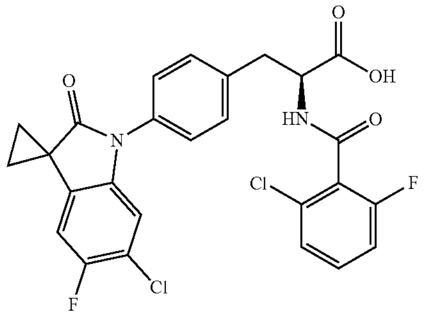 [SMILES: O=C(N[C@@H](Cc1ccc(N2C(=O)C3(CC3)c3cc(F)c(Cl)cc32)cc1)C(=O)O)c1c(F)cccc1Cl]

Dissolve (S)-3-(4-(6'-chloro-5'-fluoro-2'-oxospiro[cyclopropane-1,3'-indoline]-1'-yl)phenyl)-2-(2-chloro-6-fluorobenzamide)methyl propionate (93 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (54 mg, 60%/6). ESI-QQQ-MS: m/z 531 $[M+H]^+$. $^1H$ NMR (500 MHz, DMSO-d6): δ 12.89 (brs, 1H), 9.13 (d, J=8.3 Hz, 1H), 7.51-7.42 (m, 3H), 7.38-7.34 (m, 3H), 7.30 (d, J=8.1 Hz, 1H), 7.24 (t, J=8.6 Hz, 1H), 6.77 (d, J=6.0 Hz, 1H), 4.77-4.73 (m, 1H), 3.26 (d, J=4.1 Hz, 1H), 2.99 (dd, J=13.8, 10.8 Hz, 1H), 1.86-1.81 (m, 2H), 1.72-1.64 (m, 2H).

Example 9: Synthesis of Compound 11

Step 1

(S)-3-(4-(5'-fluoro-2'-oxospiro[cyclopropane-1,3'-indoline]-1'-yl)phenyl)-2-(triphenylamino)methyl propionate

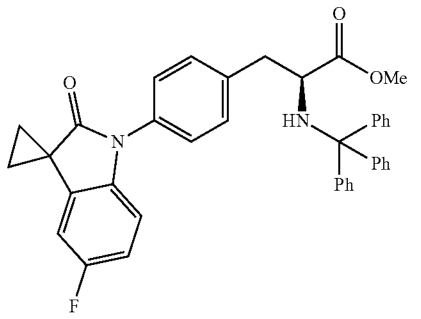 [SMILES: COC(=O)[C@H](Cc1ccc(N2C(=O)C3(CC3)c3cc(F)ccc32)cc1)NC(c1ccccc1)(c1ccccc1)c1ccccc1]

Dissolve P-5 (89 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (197 mg, 66%). ESI-QQQ-MS: m/z 597 $[M+H]^+$.

Step 2

(S)-2-amino-3-(4-(5'-fluoro-2'-oxospiro[cyclopropane-1,3'-indoline]-1'-yl)phenyl)methyl propionate

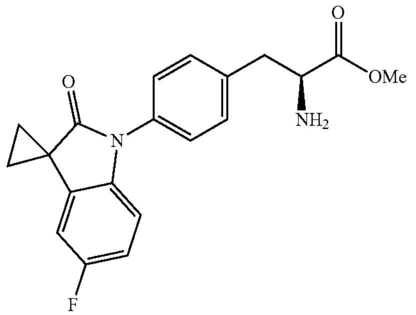 [SMILES: COC(=O)[C@@H](N)Cc1ccc(N2C(=O)C3(CC3)c3cc(F)ccc32)cc1]

Dissolve (S)-3-(4-(5'-fluoro-2'-oxospiro[cyclopropane-1,3'-indoline]-1'-yl)phenyl)-2-(triphenylamino)methyl propionate (149 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (84 mg, 95%). ESI-QQQ-MS: m/z 355 $[M+H]^+$.

Step 3

(S)-2-(2-chloro-6-fluorobenzamide)-3-(4-(5'-fluoro-2'-oxospiro[cyclopropane-1,3'-indoline]-1'-yl) phenyl)methyl propionate

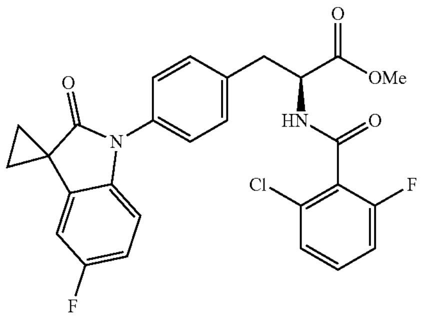 [SMILES: COC(=O)[C@H](Cc1ccc(N2C(=O)C3(CC3)c3cc(F)ccc32)cc1)NC(=O)c1c(F)cccc1Cl]

Dissolve (S)-2-amino-3-(4-(5'-fluoro-2'-oxospiro[cyclopropane-1,3'-indoline]-1'-yl)phenyl)methyl propionate (84 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (107 mg, 88%). ESI-QQQ-MS: m/z 511 $[M+H]^+$.

Step 4

(S)-2-(2-chloro-6-fluorobenzamide)-3-(4-(5'-fluoro-2'-oxospiro[cyclopropane-1,3'-indoline]-1'-yl) phenyl)propionic acid

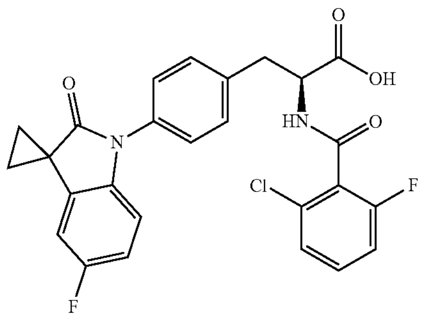 [SMILES: O=C(N[C@@H](Cc1ccc(N2C(=O)C3(CC3)c3cc(F)ccc32)cc1)C(=O)O)c1c(F)cccc1Cl]

Dissolve (S)-2-(2-chloro-6-fluorobenzamide)-3-(4-(5'-fluoro-2'-oxospiro[cyclopropane-1,3'-indoline]-1'-yl) phenyl)methyl propionate (90 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (50 mg, 57%). ESI-QQQ-MS: m/z 497 $[M+H]^+$. $^1H$ NMR (500 MHz, DMSO-d6): δ 12.86 (brs, 1H), 9.17 (d, J=8.3 Hz, 1H), 7.51-7.41 (m, 3H), 7.39-7.23 (m, 4H), 7.13-7.00 (m, 2H), 6.75-6.72 (m, 1H), 4.76-4.71 (m, 1H), 3.25 (dd. J=14.0, 4.5 Hz, 1H), 3.00 (dd, J=14.0, 10.4 Hz, 1H), 1.80-1.76 (m, 2H), 1.68-1.64 (m, 2H).

Example 10: Synthesis of Compound 12

Step 1

(S)-3-(4-(7-chloro-3,3-dimethyl-2-oxoindoline-1-yl) phenyl)-2-(triphenylamino)methyl propionate

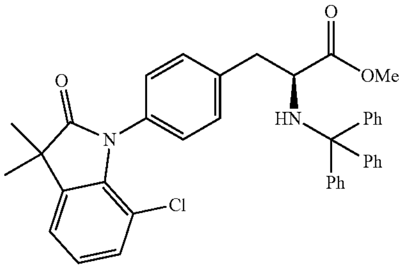 [SMILES: COC(=O)[C@H](Cc1ccc(N2C(=O)C(C)(C)c3cccc(Cl)c32)cc1)NC(c1ccccc1)(c1ccccc1)c1ccccc1]

Dissolve P-13 (97 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (154 mg, 50%). ESI-QQQ-MS: m/z 615 $[M+H]^+$.

(Step 2) (S)-2-amino-3-(4-(7-chloro-3,3-dimethyl-2-oxoindoline-1-yl)phenyl)methyl propionate

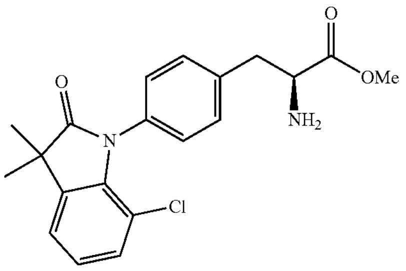 [SMILES: COC(=O)[C@@H](N)Cc1ccc(N2C(=O)C(C)(C)c3cccc(Cl)c32)cc1]

Dissolve (S)-3-(4-(3,3-dimethyl-2-oxoindoline-1-yl)phenyl)-2-(triphenylamino)methyl propionate (154 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (89 mg, 95%). ESI-QQQ-MS: m/z 373 $[M+H]^+$.

Step 3

(S)-2-(2-chloro-6-fluorobenzamide)-3-(4-(7-chloro-3,3-dimethyl-2-oxoindoline-1-yl)phenyl)methyl propionate

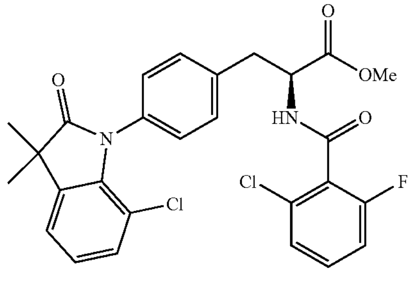 [SMILES: COC(=O)[C@H](Cc1ccc(N2C(=O)C(C)(C)c3cccc(Cl)c32)cc1)NC(=O)c1c(F)cccc1Cl]

Dissolve (S)-2-amino-3-(4-(3,3-dimethyl-2-oxoindoline-1-yl)phenyl)methyl propionate (86 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (114 mg, 94%). ESI-QQQ-MS: m/z 529 $[M+H]^+$.

Step 4

(S)-3-(4-(7-chloro-3,3-dimethyl-2-oxoindoline-1-yl)phenyl)-2-(2-chloro-6-fluorobenzamide)propionic acid

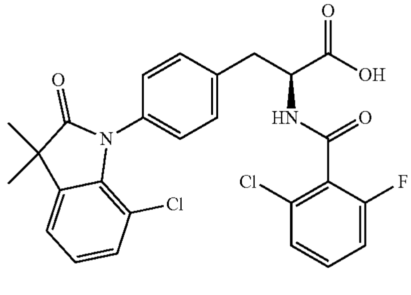 [SMILES: CC1(C)C(=O)N(c2ccc(C[C@H](NC(=O)c3c(F)cccc3Cl)C(=O)O)cc2)c2c(Cl)cccc21]

Dissolve (S)-2-(2-chloro-6-fluorobenzamide)-3-(4-(7-chloro-3,3-dimethyl-2-oxoindoline-1-yl)phenyl)meth yl propionate (90 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (49 mg, 54%). ESI-QQQ-MS: m/z 515 $[M+H]^+$. $^1H$ NMR (500 MHz, DMSO-d6): δ

12.81 (brs, 1H), 9.18 (d, J=8.1 Hz, 1H), 7.47-7.39 (m, 4H), 7.34-7.23 (m, 4H), 7.21-7.19 (m, 1H), 7.11-7.04 (m, 1H), 4.70-4.68 (m, 1H), 3.22 (dd, J=14.1, 4.3 Hz, 1H), 3.00 (dd, J=14.1, 10.3 Hz, 1H), 1.40 (s, 6H).

Example 11: Synthesis of Compound 14

Step 1

(S)-3-(4-(6'-(dimethylamino)-5'-fluoro-2'-oxospiro[cyclopropane-1,3'-indoline]-1'-yl)phenyl)-2-(triphenylamino)methyl propionate

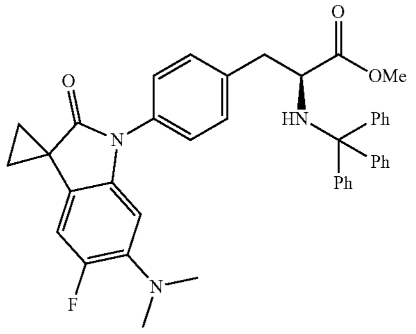 [SMILES: COC(=O)[C@H](Cc1ccc(N2C(=O)C3(CC3)c3cc(F)c(N(C)C)cc32)cc1)NC(c1ccccc1)(c1ccccc1)c1ccccc1]

Dissolve P-16 (110 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (160 mg, 50%). ESI-QQQ-MS: m/z 640 $[M+H]^+$.

(Step 2) (S)-2-amino-3-(4-(6'-(dimethylamino)-5'-fluoro-2'-oxospiro [cyclopropane-1,3'-indoline]-1'-yl)phenyl)methyl propionate

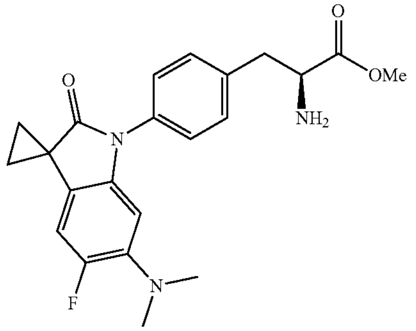 [SMILES: COC(=O)[C@@H](N)Cc1ccc(N2C(=O)C3(CC3)c3cc(F)c(N(C)C)cc32)cc1]

Dissolve (S)-3-(4-(6'-dimethylamino-5'-fluoro-2'-oxospiro[cyclopropane-1,3'-indoline]-1'-yl)phenyl)-2-(triphenylamino)methyl propionate (160 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (94 mg, 95%). ESI-QQQ-MS: m/z 398 $[M+H]^+$.

Step 3

(S)-2-(2-chloro-6-fluorobenzamide)-3-(4-(6'-(dimethylamino)-5'-fluoro-2'-oxospiro[cyclopropane-1,3'-indoline]-1'-yl)phenyl)methyl propionate

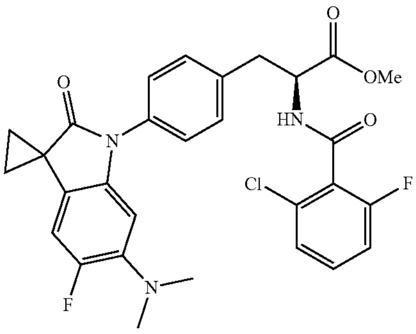

Dissolve (S)-2-amino-3-(4-(6'-(dimethylamino)-5'-fluoro-2-oxospiro[cyclopropane-1,3'-indoline]-1'-yl)phenyl)methyl propionate (91 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (114 mg, 90%). ESI-QQQ-MS: m/z 554 $[M+H]^+$.

Step 4

(S)-2-(2-chloro-6-fluorobenzamide)-3-(4-(6'-(dimethylamino)-5'-fluoro-2'-oxospiro[cyclopropane-1,3'-indoline]-1'-yl)phenyl)propionic acid

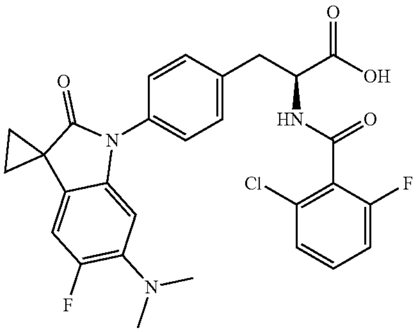 [SMILES: CN(C)c1cc2c(cc1F)C1(CC1)C(=O)N2c1ccc(C[C@H](NC(=O)c2c(F)cccc2Cl)C(=O)O)cc1]

Dissolve (S)-2-(2-chloro-6-fluorobenzamide)-3-(4-(6'-(dimethylamino)-5'-fluoro-2'-oxospiro[cyclopropane-1,3'-indoline]-1'-yl)phenyl)methyl propionate (94 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (38 mg, 42%). ESI-QQQ-MS: m/z 540 $[M+H]^+$. $^1H$ NMR (500 MHz, DMSO-d6): δ 12.97 (brs, 1H), 9.13 (d, J=8.2 Hz, 1H), 7.51-7.18 (m, 7H), 7.01 (d, J=12.2 Hz, 1H), 6.37 (d, J=7.3 Hz, 1H), 4.82-4.68 (m, 1H), 3.25 (d, J=3.9 Hz, 1H), 2.99 (dd, J=13.8, 10.9 Hz, 1H), 2.66 (s, 6H), 1.68-1.64 (m, 2H), 1.58-1.53 (m, 2H).

Example 12: Synthesis of Compound 15

Step 1

(S)-3-(4-(5'-(dimethylamino)-2'-oxospiro[cyclopropane-1,3'-indoline]-1'-yl)phenyl)-2-(triphenylamino) methyl propionate

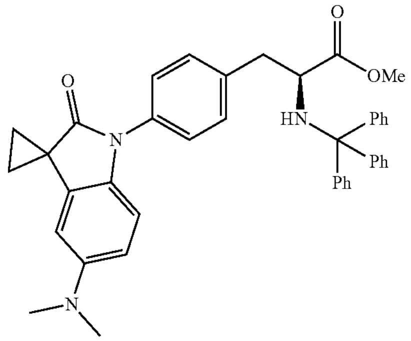 [SMILES: COC(=O)[C@H](Cc1ccc(N2C(=O)C3(CC3)c3cc(N(C)C)ccc32)cc1)NC(c1ccccc1)(c1ccccc1)c1ccccc1]

Dissolve P-15 (101 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (162 mg, 52%). ESI-QQQ-MS: m/z 622 $[M+H]^+$.

Step 2

(S)-2-amino-3-(4-(5'-(dimethylamino)-2'-oxospiro [cyclopropane-1,3'-indoline]-1'-yl)phenyl)methyl propionate

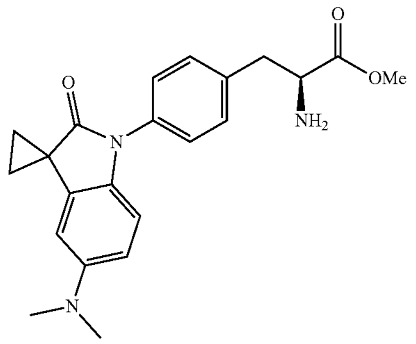 [SMILES: COC(=O)[C@@H](N)Cc1ccc(N2C(=O)C3(CC3)c3cc(N(C)C)ccc32)cc1]

Dissolve (S)-3-(4-(5'-(dimethylamino)-2'-oxospiro[cyclopropane-1,3'-indoline]-1'-yl)phenyl)-2-(triphenylamino) methyl propionate (155 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (89 mg, 94%). ESI-QQQ-MS: m/z 380 $[M+H]^+$.

Step 3

(S)-2-(2-chloro-6-fluorobenzamide)-3-(4-(5'-(dimethylamino)-2'-oxospiro[cyclopropane-1,3'-indoline]-1'-yl)phenyl)methyl propionate

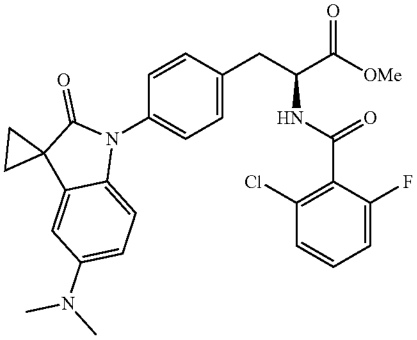 [SMILES: CN(C)c1ccc2c(c1)C1(CC1)C(=O)N2c1ccc(C[C@H](NC(=O)c2c(F)cccc2Cl)C(=O)O)cc1]

Dissolve (S)-2-amino-3-(4-(5'-(dimethylamino)-2'-oxospiro[cyclopropane-1,3'-indoline]-1'-yl)phenyl)methyl propionate (87 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (114 mg, 90%). ESI-QQQ-MS: m/z 536 $[M+H]^+$.

Step 4

(S)-2-(2-chloro-6-fluorobenzamide)-3-(4-(5'-(dimethylamino)-2'-oxospiro[cyclopropane-1,3'-indoline]-1'-yl)phenyl)propionic acid

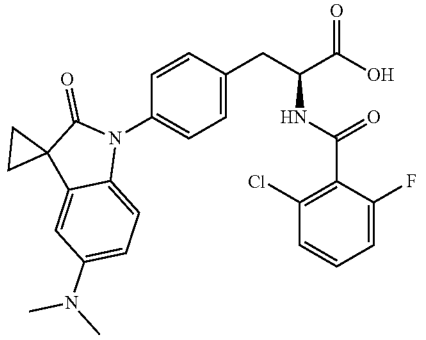

Dissolve (S)-2-(2-chloro-6-fluorobenzamide)-3-(4-(5'-(dimethylamino)-2'-oxospiro[cyclopropane-1,3'-indoline]-1'-yl)phenyl)methyl propionate (94 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (34 mg, 38%). ESI-QQQ-MS: m/z 522 $[M+H]^+$. $^1H$ NMR (500 MHz, DMSO-d6): δ 8.86 (d, J=6.7 Hz, 1H), 7.43 (t, J=8.0 Hz, 3H), 7.34-7.28 (m, 3H), 7.26-7.23 (m, 1H), 6.68 (d, J=8.5 Hz, 1H), 6.60-6.54 (m, 2H), 4.64-4.60 (m, 1H), 3.24 (dd, J=13.7, 3.8 Hz, 1H), 3.01 (dd, J=13.4, 9.6 Hz, 1H), 2.83 (s, 6H), 1.70-1.64 (m, 2H), 1.60-1.54 (m, 2H).

Example 13: Synthesis of Compound 16

(Step 1) (S)-3-(4-(6'-fluoro-2'-oxospiro [cyclopropane-1,3'-indoline]-1'-yl)phenyl)-2-(triphenylamino) methyl propionate

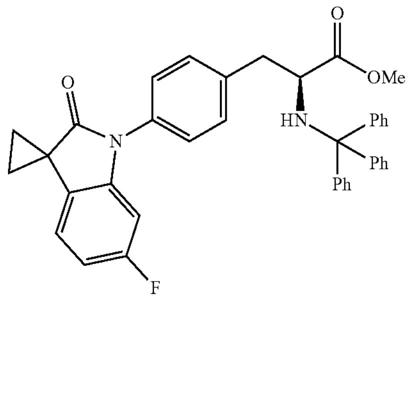 [SMILES: COC(=O)[C@H](Cc1ccc(N2C(=O)C3(CC3)c3ccc(F)cc32)cc1)NC(c1ccccc1)(c1ccccc1)c1ccccc1]

Dissolve P4 (89 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (210 mg, 70%). ESI-QQQ-MS: m/z 597 $[M+H]^+$.

Step 2

(S)-2-amino-3-(4-(6'-fluoro-2'-oxospiro[cyclopropane-1,3'-indoline]-1'-yl)phenyl)methyl propionate

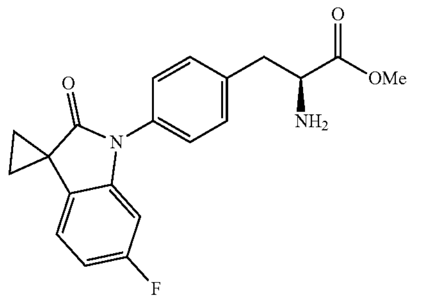 [SMILES: COC(=O)[C@@H](N)Cc1ccc(N2C(=O)C3(CC3)c3ccc(F)cc32)cc1]

Dissolve (S)-3-(4-(6'-fluoro-2'-oxospiro[cyclopropane-1,3'-indoline]-1'-yl)phenyl)-2-(triphenylamino)methyl propionate (149 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (81 mg, 92%). ESI-QQQ-MS: m/z 355 $[M+H]^+$.

Step 3

(S)-2-(2-chloro-6-fluorobenzamide)-3-(4-(6'-fluoro-2'-oxospiro[cyclopropane-1,3'-indoline]-1'-yl) phenyl)methyl propionate

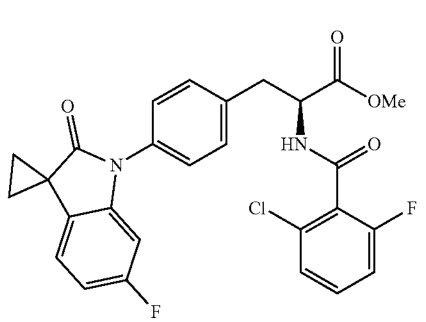 [SMILES: COC(=O)[C@H](Cc1ccc(N2C(=O)C3(CC3)c3ccc(F)cc32)cc1)NC(=O)c1c(F)cccc1Cl]

Dissolve (S)-2-amino-3-(4-(6'-fluoro-2'-oxospiro[cyclopropane-1,3'-indoline]-1'-yl)phenyl)methyl propionate (81 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (105 mg, 90%). ESI-QQQ-MS: m/z 511 $[M+H]^+$.

Step 4

(S)-2-(2-chloro-4-fluorobenzamide)-3-(4-(6'-fluoro-2'-oxospiro[cyclopropane-1,3'-indoline]-1'-yl) phenyl)propionic acid

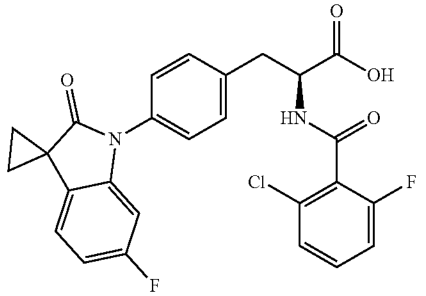 [SMILES: O=C(N[C@@H](Cc1ccc(N2C(=O)C3(CC3)c3ccc(F)cc32)cc1)C(=O)O)c1c(F)cccc1Cl]

Dissolve (S)-2-(2-chloro-6-fluorobenzamide)-3-(4-(6'-fluoro-2'-oxospiro[cyclopropane-1,3'-indoline]-1'-yl) phenyl)methyl propionate (87 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 ml each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (51 mg, 60%). ESI-QQQ-MS: m/z 497 $[M+H]^+$. $^1H$ NMR (500 MHz, DMSO): δ 12.89 (s, 1H), 9.15 (d, J=8.3 Hz, 1H), 7.51-7.42 (m, 3H), 7.38 (d, J=8.3 Hz, 2H), 7.30 (d, J=8.1 Hz, 1H), 7.24 (t, J=8.6 Hz, 1H), 7.16-7.12 (m, 1H), 6.92-6.84 (m, 1H), 6.53 (dd, J=9.4, 2.3 Hz, 1H), 4.77-4.73 (m, 1H), 3.26 (dd, J=14.0, 4.4 Hz, 1H), 3.00 (dd, J=13.9, 10.5 Hz, 1H), 1.75-1.71 (m, 2H), 1.64-1.60 (m, 2H).

Example 14: Synthesis of Compound 17

(Step 1) (S)-3-(4-(7'-fluoro-2'-oxospiro [cyclopropane-1,3'-indoline]-1'-yl)phenyl)-2-(triphenylamino) methyl propionate

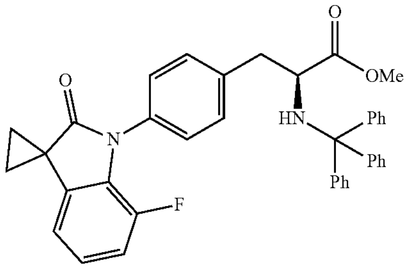 [SMILES: COC(=O)[C@H](Cc1ccc(N2C(=O)C3(CC3)c3cccc(F)c32)cc1)NC(c1ccccc1)(c1ccccc1)c1ccccc1]

Dissolve P-3 (89 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (216 mg, 72%). ESI-QQQ-MS: m/z 597 $[M+H]^+$.

(Step 2) methyl (S)-2-amino-3-(4-(7'-fluoro-2'-oxospiro[cyclopropane-1,3'-indoline]-1'-yl)phenyl) propionate

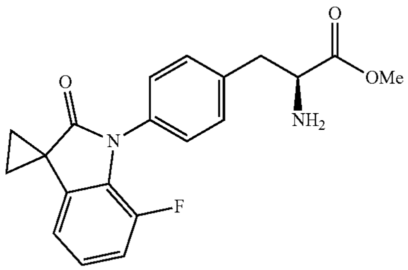 [SMILES: COC(=O)[C@@H](N)Cc1ccc(N2C(=O)C3(CC3)c3cccc(F)c32)cc1]

Dissolve (S)-3-(4-(7'-fluoro-2'-oxospiro[cyclopropane-1,3'-indoline]-1'-yl)phenyl)-2-(triphenylamino)methyl propionate (149 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (82 mg, 91%). ESI-QQQ-MS: m/z 355 $[M+H]^+$.

Step 3

(S)-2-(2-chloro-6-fluorobenzamide)-3-(4-(7'-fluoro-2'-oxospiro[cyclopropane-1,3'-indoline]-1'-yl) phenyl)methyl propionate

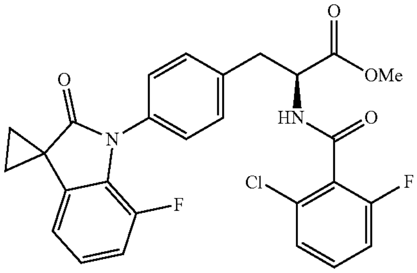 [SMILES: COC(=O)[C@H](Cc1ccc(N2C(=O)C3(CC3)c3cccc(F)c32)cc1)NC(=O)c1c(F)cccc1Cl]

Dissolve (S)-2-amino-3-(4-(7'-fluoro-2'-oxospiro[cyclopropane-1,3'-indoline]-1'-yl)phenyl)methyl propionate (81 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (102 mg, 87%). ESI-QQQ-MS: m/z 511 $[M+H]^+$.

Step 4

(S)-2-(2-chloro-6-fluorobenzamide)-3-(4-(7-fluoro-2'-oxospiro[cyclopropane-1,3'-indoline]-1'-yl) phenyl)propionic acid

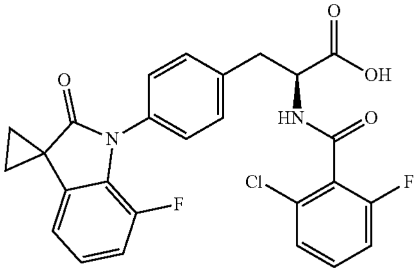 [SMILES: O=C(N[C@@H](Cc1ccc(N2C(=O)C3(CC3)c3cccc(F)c32)cc1)C(=O)O)c1c(F)cccc1Cl]

Dissolve (S)-2-(2-chloro-6-fluorobenzamide)-3-(4-(7-fluoro-2'-oxospiro[cyclopropane-1,3'-indoline]-1'-yl) phenyl)methyl propionate (87 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (53 mg, 62%). ESI-QQQ-MS: m/z 497 $[M+H]^+$. $^1H$ NMR (500

MHz, DMSO): δ 12.85 (s, 1H), 9.18 (d, J=8.1 Hz, 1H), 7.48-7.21 (m, 7H), 7.09-7.05 (m, 2H), 6.98-6.94 (m, 1H), 4.72-4.68 (m, 1H), 3.22 (dd, J=14.1, 4.4 Hz, 1H), 3.00 (dd, J=14.1, 10.3 Hz, 1H), 1.78-1.74 (m, 2H), 1.69-1.65 (m, 2H).

Example 15: Synthesis of Compound 18

Step 1

(S)-3-(4-(6',7'-difluoro-2'-oxospiro[cyclopropane-1,3'-indoline]-1'-yl)phenyl)-2-(triphenylamino)methyl propionate

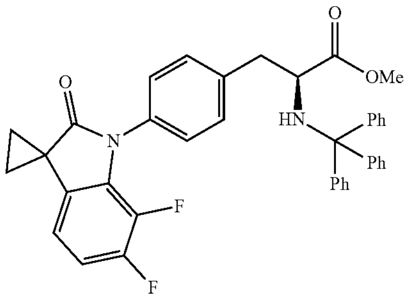 [SMILES: COC(=O)[C@H](Cc1ccc(N2C(=O)C3(CC3)c3ccc(F)c(F)c32)cc1)NC(c1ccccc1)(c1ccccc1)c1ccccc1]

Dissolve P-12 (98 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 361. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (206 mg, 67%). ESI-QQQ-MS: m/z 615 $[M+H]^+$.

Step 2

(S)-2-amino-3-(4-(6',7'-difluoro-2'-oxospiro[cyclopropane-1,3'-indoline]-1'-yl)phenyl)methyl propionate

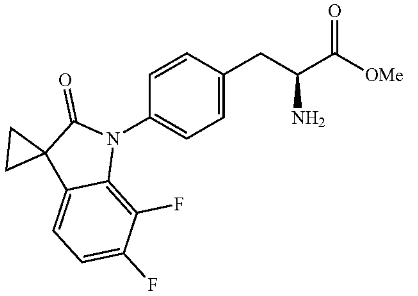 [SMILES: COC(=O)[C@@H](N)Cc1ccc(N2C(=O)C3(CC3)c3ccc(F)c(F)c32)cc1]

Dissolve (S)-3-(4-(6',7'-difluoro-2'-oxospiro[cyclopropane-1,3'-indoline]-1'-yl)phenyl)-2-(triphenylamino)methyl propionate (154 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (87 mg, 94%). ESI-QQQ-MS: m/z 373 $[M+H]^+$.

Step 3

(S)-2-(2-chloro-6-fluorobenzamide)-3-(4-(6',7'-difluoro-2'-oxospiro[cyclopropane-1,3'-indoline]-1'-yl)phenyl)methyl propionate

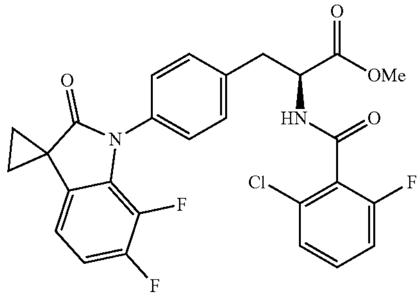 [SMILES: COC(=O)[C@H](Cc1ccc(N2C(=O)C3(CC3)c3ccc(F)c(F)c32)cc1)NC(=O)c1c(F)cccc1Cl]

Dissolve (S)-2-amino-3-(4-(6',7'-difluoro-2'-oxospiro[cyclopropane-1,3'-indoline]-1'-yl)phenyl)methyl propionate (86 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (107 mg, 88%). ESI-QQQ-MS: m/z 529 $[M+H]^+$.

Step 4

(S)-2-(2-chloro-6-fluorobenzamide)-3-(4-(6',7'-difluoro-2'-oxospirino[cyclopropane-1,3'-indoline]-1'-yl)phenyl)propionic acid

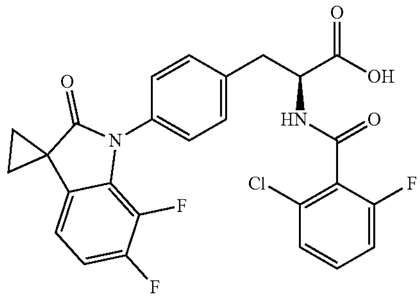 [SMILES: O=C(N[C@@H](Cc1ccc(N2C(=O)C3(CC3)c3ccc(F)c(F)c32)cc1)C(=O)O)c1c(F)cccc1Cl]

Dissolve (S)-2-(2-chloro-6-fluorobenzamide)-3-(4-(6',7'-difluoro-2'-oxospiro[cyclopropane-1,3'-indoline]-1'-yl)phenyl))methyl propionate (90 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (49 mg, 56%). ESI-QQQ-MS: m/z 515 $[M+H]^+$. $^1H$ NMR (500 MHz, DMSO-d6): δ 12.87 (brs, 1H), 9.18 (d, J=8.2 Hz, 1H), 7.47-7.36 (m, 5H), 7.33-7.20 (m, 2H), 7.11-7.06 (m, 11H), 6.97-6.94 (m, 1H), 4.73-4.68 (m, 1H), 3.23 (dd, J=14.1, 4.4 Hz, 1H), 3.01 (dd, J=14.1, 10.3 Hz, 1H), 1.78-1.74 (m, 2H), 1.68-1.64 (m, 2H).

Example 16: Synthesis of Compound 19

Step 1

(S)-3-(4-(2'-oxospiro[cyclopropane-1,3'-pyrrolo[2,3-b]pyridine]-1'(2'H)-yl)phenyl)-2-(triphenylamino) methyl propionate

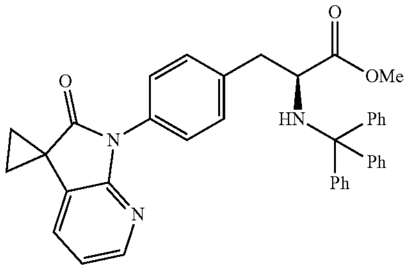 [SMILES: COC(=O)[C@H](Cc1ccc(N2C(=O)C3(CC3)c3cccnc32)cc1)NC(c1ccccc1)(c1ccccc1)c1ccccc1]

Dissolve P-17 (80 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (145 mg, 50%). ESI-QQQ-MS: m/z 580 $[M+H]^+$.

Step 2

(S)-2-amino-3-(4-(2'-oxospiro[cyclopropane-1,3'-pyrrolo[2,3-b]pyridine]-1'(2'H)-yl)phenyl)methyl propionate

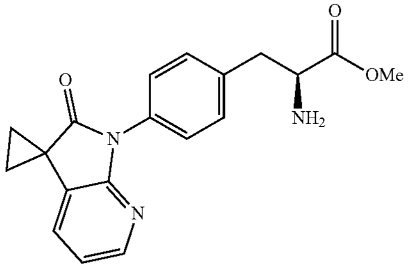 [SMILES: COC(=O)[C@@H](N)Cc1ccc(N2C(=O)C3(CC3)c3cccnc32)cc1]

Dissolve (S)-3-(4-(2'-oxospiro[cyclopropane-1,3-pyrrolo [2,3-b]pyridine]-1'(2'H)-yl)phenyl)-2-(triphenylamino) methyl propionate (145 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (78 mg, 92%). ESI-QQQ-MS: m/z 338 $[M+H]^+$.

Step 3

(S)-2-(2,6-dichlorobenzamido)-3-(4-(2'-oxospiro [cyclopropane-1,3'-pyrrolo[2,3-b]pyridine]-1'(2'H)-yl)phenyl)methyl propionate

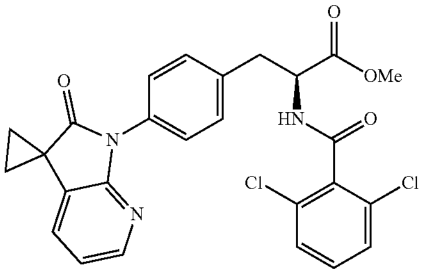 [SMILES: COC(=O)[C@H](Cc1ccc(N2C(=O)C3(CC3)c3cccnc32)cc1)NC(=O)c1c(Cl)cccc1Cl]

Dissolve (S)-2-amino-3-(4-(2'-oxospiro[cyclopropane-1, 3'-pyrrolo[2,3-b]pyridine]-1'(2'H)-yl)phenyl)methyl propionate (78 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (100 mg, 85%). ESI-QQQ-MS: m/z 510 $[M+H]^+$.

Step 4

(S)-2-(2,6-dichlorobenzamido)-3-(4-(2'-oxospiro [cyclopropane-1,3'-pyrrolo[2,3-b]pyridine]-1'(2'H)-yl)phenyl)propionic acid

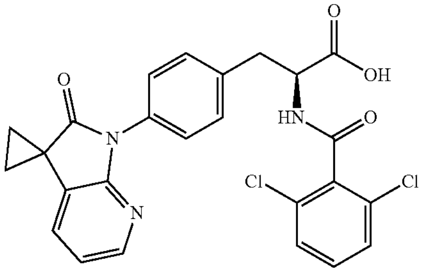 [SMILES: O=C(N[C@@H](Cc1ccc(N2C(=O)C3(CC3)c3cccnc32)cc1)C(=O)O)c1c(Cl)cccc1Cl]

Dissolve (S)-2-(2,6-dichlorobenzamido)-3-(4-(2'-oxospiro[cyclopropane-1,3'-pyrrolo[2,3-b]pyridine]-1'(2'H)-yl)phenyl)methyl propionate (87 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (33 mg, 40%). ESI-QQQ-MS: m/z 496 $[M+H]^+$. $^1H$ NMR (500 MHz, DMSO-d6): δ 8.80 (s, 1H), 8.07 (d, J=4.4 Hz, 1H), 7.51 (d, J=7.0 Hz, 1H), 7.42-7.30 (m, 8H), 7.11-7.01 (m, 1H), 4.68-4.62 (m, 1H), 3.24 (d, J=4.1 Hz, 1H), 3.03 (dd, J=13.3, 9.1 Hz, 1H), 1.82-1.78 (m, 2H), 1.72-1.66 (m, 2H).

Example 17: Synthesis of Compound 20

Step 1

(S)-3-(4-(7'-chloro-2'-oxospiro[cyclopropane-1,3'-indoline]-1'-yl)phenyl)-2-(2,4,6-trichlorobenzoylamino)methyl propionate

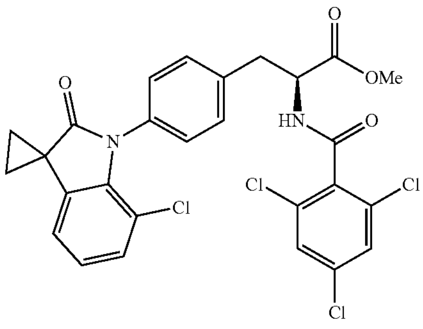 [SMILES: COC(=O)[C@H](Cc1ccc(N2C(=O)C3(CC3)c3cccc(Cl)c32)cc1)NC(=O)c1c(Cl)cc(Cl)cc1Cl]

Dissolve (S)-2-amino-3-(4-(7'-fluoro-2'-oxospiro[cyclopropane-1,3'-indoline]-1'-yl)phenyl)methyl propionate (85 mg, 0.23 mmol, the preparation process is detailed in Example 2) and triethylamine (30 mg, 0.3 mmol) in dichloromethane (2 mL), cool to 0° C., add the intermediate P-34 (61 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (125 mg, 94%). ESI-QQQ-MS: m/z 577 $[M+H]^+$.

Step 2

(S)-3-(4-(7'-chloro-2'-oxospiro[cyclopropane-1,3'-indoline]-1'-yl)phenyl)-2-(2,4,6-trichlorobenzoylamino)propionic acid

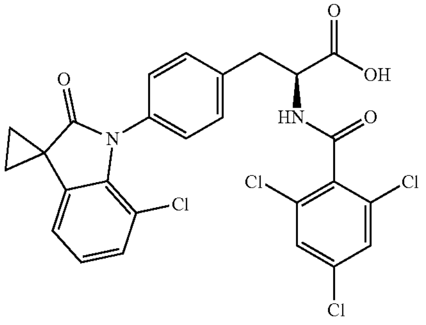 [SMILES: O=C(N[C@@H](Cc1ccc(N2C(=O)C3(CC3)c3cccc(Cl)c32)cc1)C(=O)O)c1c(Cl)cc(Cl)cc1Cl]

Dissolve (S)-3-(4-(7'-chloro-2'-oxospiro[cyclopropane-1,3'-indoline]-1-yl)phenyl)-2-(2,4,6-trichlorobenzoylamino) methyl propionate (98 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (54 mg, 56%). ESI-QQQ-MS: m/z 562 $[M+H]^+$. $^1H$ NMR (500 MHz, DMSO-d6): δ 12.91 (brs, 1H), 9.18 (d, J=8.0 Hz, 1H), 7.67 (s, 2H), 7.44-7.15 (m, 5H), 7.10-7.01 (m, 2H), 4.73-4.69 (m, 1H), 3.26-3.19 (m, 1H), 3.04-2.92 (m, 1H), 1.78-1.74 (m, 2H), 1.68-1.64 (m, 2H).

Example 18: Synthesis of Compound 21

Step 1

(S)-3-(4-(7'-chloro-2'-oxospiro[cyclopropane-1,3'-indoline]-1'-yl)phenyl)-2-(2,6-dichloro-4-(diethylamino)benzoylamino)methyl propionate

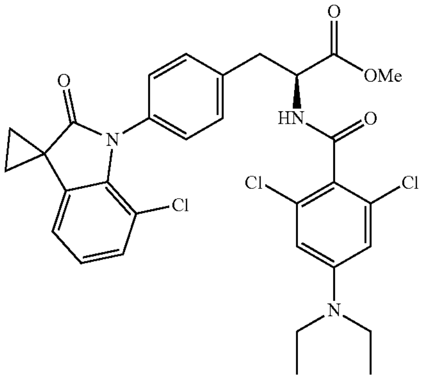 [SMILES: CCN(CC)c1cc(Cl)c(C(=O)N[C@@H](Cc2ccc(N3C(=O)C4(CC4)c4cccc(Cl)c43)cc2)C(=O)OC)c(Cl)c1]

Dissolve (S)-2-amino-3-(4-(7'-fluoro-2-oxospiro[cyclopropane-1,3'-indoline]-1'-yl)phenyl)methyl propionate (85 mg, 0.23 mmol, the preparation process is detailed in Example 2) and triethylamine (30 mg, 0.3 mmol) in dichloromethane (2 mL), cool to 0° C., add the intermediate P-35 (70 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (125 mg, 94%). ESI-QQQ-MS: m/z 614 $[M+H]^+$.

Step 2

(S)-3-(4-(7'-chloro-2'-oxospiro[cyclopropane-1,3'-indoline]-1'-yl)phenyl)-2-(2,6-dichloro-4-(diethylamino)benzoylamino)propionic acid

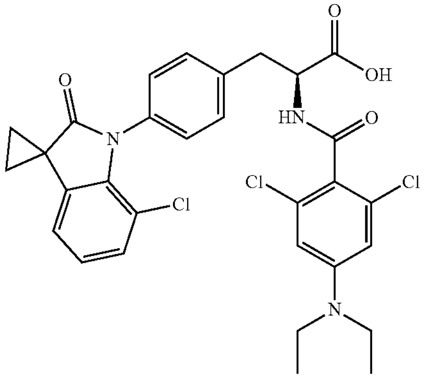 [SMILES: CCN(CC)c1cc(Cl)c(C(=O)N[C@@H](Cc2ccc(N3C(=O)C4(CC4)c4cccc(Cl)c43)cc2)C(=O)O)c(Cl)c1]

Dissolve (S)-3-(4-(7'-chloro-2'-oxospiro[cyclopropane-1,3'-indoline]-1'-yl)phenyl)-2-(2,6-dichloro-4-(diethylamino)benzoylamino)methyl propionate (102 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (54 mg, 56%). ESI-QQQ-MS: m/z 600 $[M+H]^+$. $^1H$ NMR (500 MHz, DMSO-d6): δ 12.67 (brs, 1H), 8.79 (d, J=7.7 Hz, 1H), 7.40 (d, J=8.4 Hz, 2H), 7.26 (d, J=7.3 Hz, 2H), 7.20-7.15 (m, 1H), 7.09-7.01 (m, 2H), 6.57 (s, 2H), 4.64-4.60 (m, 1H), 3.33-3.20 (m, 4H), 3.17 (dd, J=14.1, 4.2 Hz, 1H), 3.00 (dd, J=14.0, 10.1 Hz, 1H), 1.78-1.74 (m, 2H), 1.68-1.64 (m, 2H), 1.05 (t, J=7.0 Hz, 6H).

Example 19: Synthesis of Compound 22

Step 1

(S)-3-(4-(7'-chloro-2'-oxospiro[cyclopropane-1,3'-indoline]-1'-yl)phenyl)-2-(2,6-dichloro-4-morpholinoylbenzoylamino)methyl propionate

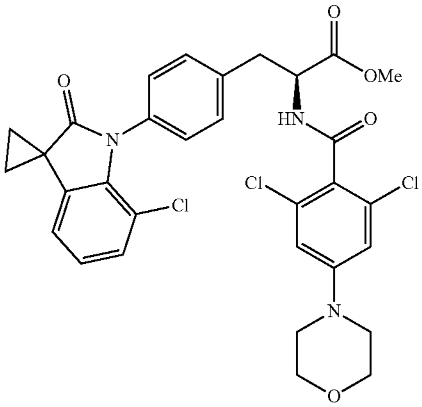 [SMILES: COC(=O)[C@H](Cc1ccc(N2C(=O)C3(CC3)c3cccc(Cl)c32)cc1)NC(=O)c1c(Cl)cc(N2CCOCC2)cc1Cl]

Dissolve (S)-2-amino-3-(4-(7'-chloro-2'-oxospiro[cyclopropane-1,3'-indoline]-1'-yl)phenyl)methyl propionate (85 mg, 0.23 mmol, the preparation process is detailed in Example 2) and triethylamine (30 mg, 0.3 mmol) in dichloromethane (2 mL), cool to 0° C., add the intermediate P-36 (74 mg, 0.25 mmol) dropwise to the reaction system, and the react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (123 mg, 85%). ESI-QQQ-MS: m/z 628 $[M+H]^+$.

Step 2

(S)-3-(4-(7'-chloro-2'-oxospiro[cyclopropane-1,3'-indoline]-1'-yl)phenyl)-2-(2,6-dichloro-4-morpholinobenzoylamino)propionic acid

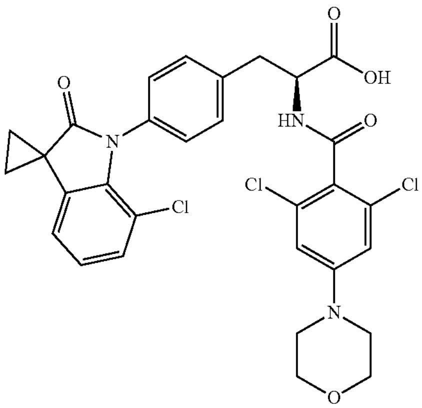 [SMILES: O=C(N[C@@H](Cc1ccc(N2C(=O)C3(CC3)c3cccc(Cl)c32)cc1)C(=O)O)c1c(Cl)cc(N2CCOCC2)cc1Cl]

Dissolve (S)-3-(4-(7'-chloro-2'-oxospiro[cyclopropane-1, 3'-indoline]-1-yl)phenyl)-2-(2,6-dichloro-4-morpholinobenzoylamino)methyl propionate (107 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (54 mg, 52%). ESI-QQQ-MS: m/z 614 $[M+H]^+$. $^1H$ NMR (500 MHz, DMSO-d6): δ 8.54 (s, 1H), 7.40-7.38 (m, 2H), 7.24-7.17 (m, 3H), 7.09-7.02 (m, 2H), 6.93 (s, 2H), 4.59-4.52 (m, 1H), 3.72-3.66 (m, 4H), 3.21 (s, 1H), 3.21-3.17 (m, 4H), 3.04 (dd, J=13.4, 9.1 Hz, 1H), 1.78-1.74 (m, 2H), 1.68-1.64 (m, 2H).

Example 20: Synthesis of Compound 23

Step 1

(2S)-2-(4-(2-oxa-5-azabicyclo[2.2.1]heptan-5-yl)-2,6-dichlorobenzamido)-3-(4-(7'-chloro-2'-oxospiro[cyclopropane-1,3'-indoline]-1'-yl)phenyl)methyl propionate

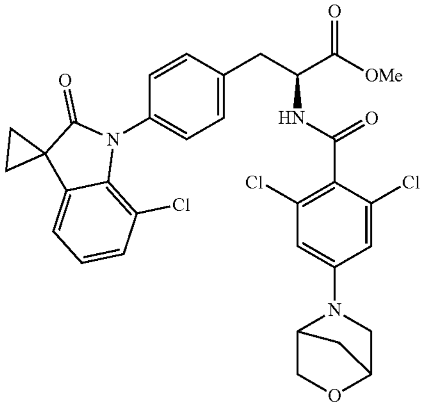 [SMILES: COC(=O)[C@H](Cc1ccc(N2C(=O)C3(CC3)c3cccc(Cl)c32)cc1)NC(=O)c1c(Cl)cc(N2CC3CC2CO3)cc1Cl]

Dissolve (S)-2-amino-3-(4-(7'-chloro-2-oxospiro[cyclopropane-1,3'-indoline]-1'-yl)phenyl) methyl propionate (85 mg, 0.23 mmol, the preparation process is detailed in Example 2) and triethylamine (30 mg, 0.3 mmol) in dichloromethane (2 mL), cool to 0° C., add the intermediate P-37 hept-5-yl (77 mg, 0.25 mmol) dropwise to the reaction system, and the react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (109 mg, 74%). ESI-QQQ-MS: m/z 640 $[M+H]^+$.

Step 2

(2S)-2-(4-(2-oxa-5-azabicyclo[2.2.1]heptan-5-yl)-2,6-dichlorobenzamido)-3-(47'-chloro-2'-oxospiro[cyclopropane-1,3'-indoline]-1'-yl)phenyl)propionic acid

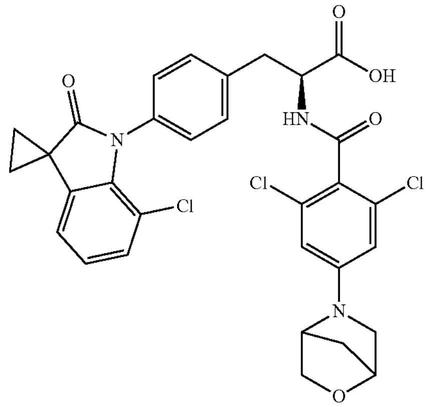 [SMILES: O=C(N[C@@H](Cc1ccc(N2C(=O)C3(CC3)c3cccc(Cl)c32)cc1)C(=O)O)c1c(Cl)cc(N2CC3CC2CO3)cc1Cl]

Dissolve (2S)-methyl 2-(4-(2-oxa-5-azabicyclo[2.2.1]heptan-5-yl)-2,6-dichlorobenzamido)-3-(4-(7'-chloro-2'-oxospiro[cyclopropane-1,3'-indoline]-1'-yl)phenyl)methyl propionate (109 mg, 0.17 mmol) in tetrahydrofuran (2 mL), then add 0.5 mol/L sodium hydroxide solution (0.4 mL, 0.2 mmol), and react at room temperature reaction for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (52 mg, 49%). ESI-QQQ-MS: m/z 626 $[M+H]^+$. $^1H$ NMR (500 MHz, DMSO-d6): δ 12.76 (brs, 1H), 8.81 (d, J=5.9 Hz, 1H), 7.40 (d, J=8.0 Hz, 2H), 7.27-7.17 (m, 3H), 7.11-7.01 (m, 2H), 6.63 (s, 2H), 4.67 (s, 1H), 4.62 (s, 2H), 3.73 (d, J=7.3 Hz, 1H), 3.58 (d, J=7.5 Hz, 1H), 3.45 (d, J=9.4 Hz, 1H), 3.23-3.13 (m, 1H), 3.05-2.95 (m, 2H), 1.91-1.83 (m, 2H), 1.77-1.66 (m, 4H).

Example 21: Synthesis of Compound 24

Step 1

(S)-3-(4-(7'-chloro-2'-oxospiro[cyclopropane-1,3'-indoline]-1-yl)phenyl)-2-(2,6-dichloro-4-(4-morpholinopiperidin-1-yl)benzoylamino)methyl propionate

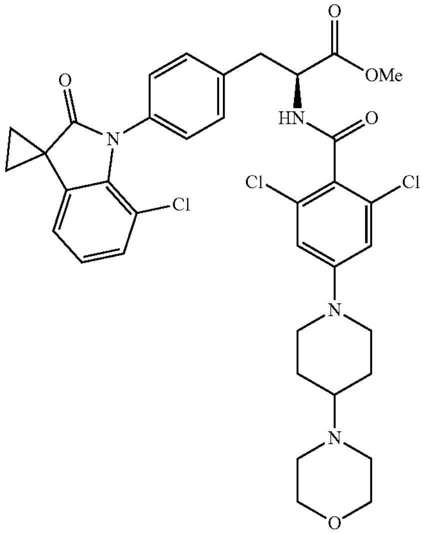 [SMILES: COC(=O)[C@H](Cc1ccc(N2C(=O)C3(CC3)c3cccc(Cl)c32)cc1)NC(=O)c1c(Cl)cc(N2CCC(N3CCOCC3)CC2)cc1Cl]

Dissolve (S)-2-amino-3-(4-(7'-chloro-2'-oxospiro[cyclopropane-1,3'-indoline]-1'-yl)phenyl) methyl propionate (85 mg, 0.23 mmol, the preparation process is detailed in Example 2) and triethylamine (30 mg, 0.3 mmol) in dichloromethane (2 mL), cool to 0° C., add the intermediate P-38 (94 mg, 0.25 mmol) dropwise to the reaction system, and the react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (129 mg, 79%). ESI-QQQ-MS: m/z 711 $[M+H]^+$.

Step 2

(S)-3-(4-(7'-chloro-2'-oxospiro[cyclopropane-1,3'-indoline]-1'-yl)phenyl)-2-(2,6-dichloro-4-(4-morpholinopiperidin-1-yl)benzoylamino)propionic acid

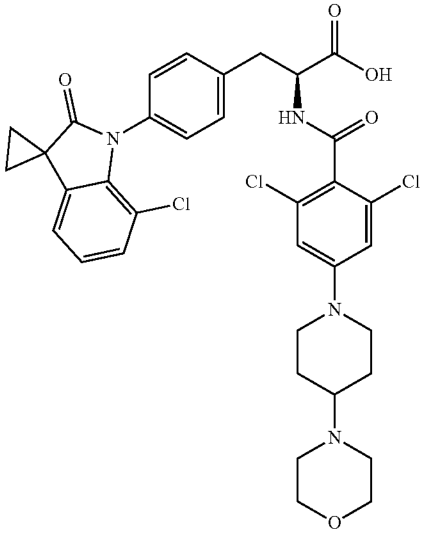 [SMILES: O=C(N[C@@H](Cc1ccc(N2C(=O)C3(CC3)c3cccc(Cl)c32)cc1)C(=O)O)c1c(Cl)cc(N2CCC(N3CCOCC3)CC2)cc1Cl]

Dissolve (S)-3-(4-(7'-chloro-2'-oxospiro[cyclopropane-1,3'-indoline]-1'-yl)phenyl)-2-(2,6-dichloro-4-(4-morpholinopiperidin-1-yl)benzoylamino)methyl propionate (121 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (59 mg, 50%). ESI-QQQ-MS: m/z 696 $[M+H]^+$. $^1H$ NMR (500 MHz, DMSO-d6): δ 12.75 (brs, 1H), 8.87 (d, J=7.7 Hz, 1H), 7.40 (d, J=8.4 Hz, 2H), 7.27-7.25 (m, 2H), 7.20-7.16 (m, 1H), 7.09-7.02 (m, 2H), 6.90 (s, 2H), 4.65-4.61 (m, 1H), 3.82 (d, J=12.9 Hz, 2H), 3.55 (s, 4H), 3.17 (dd, J=14.1, 4.3 Hz, 1H), 3.00 (dd, J=14.0, 10.2 Hz, 1H), 2.76 (t, J=11.9 Hz, 2H), 2.45 (s, 4H), 2.37-2.29 (m, 1H), 1.81-1.75 (m, 4H), 1.67-1.65 (m, 2H), 1.41-1.35 (m, 2H).

Example 22: Synthesis of Compound 25

Step 1

(S)-3-(4-(7-chloro-3-methyl-2-oxo-2,3-dihydro-1H-benzo[d]imidazol-1-yl)phenyl)-2-(triphenylmethylamino)methyl propionate

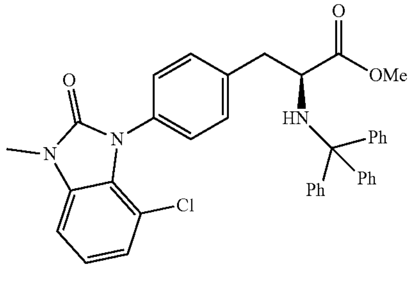 [SMILES: COC(=O)[C@H](Cc1ccc(-n2c(=O)n(C)c3cccc(Cl)c32)cc1)NC(c1ccccc1)(c1ccccc1)c1ccccc1]

Dissolve P-18 (91 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=5:1) to obtain the title compound (180 mg, (0%). ESI-QQQ-MS: m/z 602 $[M+H]^+$.

Step 2

(S)-2-amino-3-(4-(7-chloro-3-methyl-2-oxo-2,3-dihydro-H-benzo[d]imidazol-1-yl)phenyl)methyl propionate

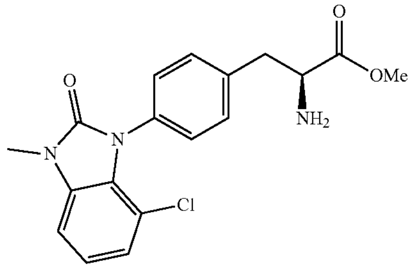

Dissolve (S)-3-(4-(7-fluoro-3-methyl-2-oxo-2,3-dihydro-1H-benzo[d]imidazol-1-yl)phenyl)-2-(triphenylamino) methyl propionate (150 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (85 mg, 95%). ESI-QQQ-MS: m/z 360 $[M+H]^+$.

Step 3

(S)-3-(4-(7-chloro-3-methyl-2-oxo-2,3-dihydro-1H-benzo[d]imidazol-1-yl)phenyl)-2-(2-chloro-6-fluorobenzamide)methyl propionate

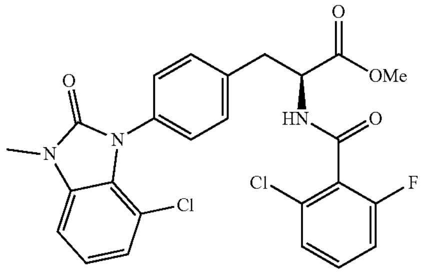

Dissolve (S)-2-amino-3-(4-(7-fluoro-3-methyl-2-oxo-2,3-dihydro-1H-benzo[d]imidazol-1-yl)phenyl) methyl propionate (86 mg, 0.24 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (105 mg, 85%/6). ESI-QQQ-MS: m/z 516 $[M+H]^+$.

Step 4

(S)-3-(4-(7-chloro-3-methyl-2-oxo-2,3-dihydro-1H-benzo-1H-imidazol-1-yl)phenyl)-2-(2-chloro-6-fluorobenzamide)propionic acid

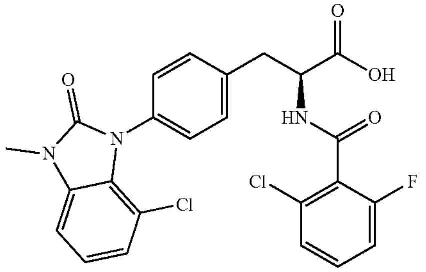

Dissolve (S)-3-(4-(7-chloro-3-methyl-2-oxo-2,3-dihydro-1H-benzo-1H-imidazol-1-yl)phenyl)-2-(2-chloro-6-fluorobenzamide)methyl propionate (88 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated saline solution once, dry over anhydrous sodium sulfate, filter and concentrate with vacuum, and purify the concentrate by RP-HPLC ($H_2O/CH_3CN$ system containing 0.1% formic acid) to obtain the title compound (60 mg, 70%). ESI-QQQ-MS: m/z 502 $[M+H]^+$. $^1H$ NMR (500 MHz, DMSO-d6): δ 12.86 (brs, 1H), 9.19 (d, J=8.1 Hz, 1H), 7.48-7.38 (m, 3H), 7.33-7.22 (m, 5H), 7.12 (t, J=8.0 Hz, 1H), 7.03 (d, J=8.1 Hz, 1H), 4.73-4.68 (m, 1H), 3.39 (s, 3H), 3.23 (dd, J=14.1.4.1 Hz, 1H), 3.02 (dd, J=13.9, 10.5 Hz, 1H).

Example 23: Synthesis of Compound 26

Step 1

(S)-3-(4-(5-chloro-3-cyclopropyl-2-oxo-2,3-dihydro-1H-benzo[d]imidazol-1-yl)phenyl)-2-(triphenylmethylamino)methyl propionate

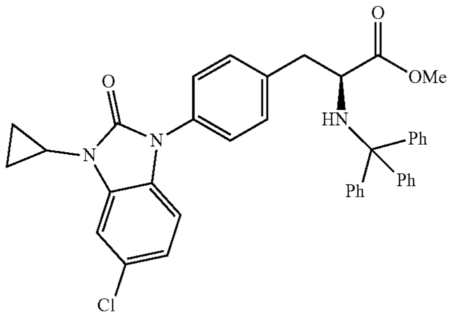 [SMILES: COC(=O)[C@H](Cc1ccc(-n2c(=O)n(C3CC3)c3cc(Cl)ccc32)cc1)NC(c1ccccc1)(c1ccccc1)c1ccccc1]

Dissolve P-19 (104 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol) to reaction system, under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=5:1) to obtain the title compound (198 mg, 63%). ESI-QQQ-MS: m/z 628 $[M+H]^+$.

Step 2

(S)-2-amino-3-(4-(5-chloro-3-cyclopropyl-2-oxo-2,3-dihydro-1H-benzo[d]imidazol-1-yl)phenyl) methyl propionate

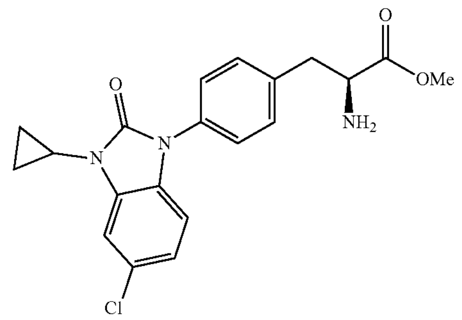 [SMILES: COC(=O)[C@@H](N)Cc1ccc(-n2c(=O)n(C3CC3)c3cc(Cl)ccc32)cc1]

Dissolve (S)-3-(4-(5-chloro-3-cyclopropyl-2-oxo-2,3-dihydro-H-benzo[d]imidazol-1-yl)phenyl)-2-(triphenylamino)methyl propionate (157 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (88 mg, 91%). ESI-QQQ-MS: m/z 386 $[M+H]^+$.

Step 3

(S)-3-(4-(5-chloro-3-cyclopropyl-2-oxo-2,3-dihydro-1H-benzo[d]imidazol-1-yl)phenyl)-2-(2,6-dichlorobenzamido)methyl propionate

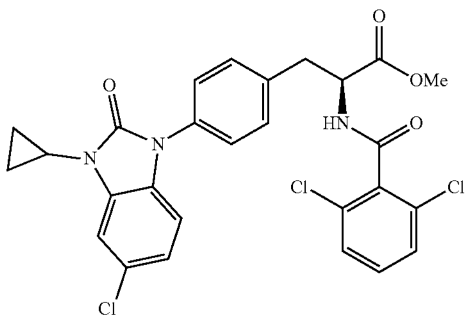 [SMILES: COC(=O)[C@H](Cc1ccc(-n2c(=O)n(C3CC3)c3cc(Cl)ccc32)cc1)NC(=O)c1c(Cl)cccc1Cl]

Dissolve (S)-2-amino-3-(4-(5-chloro-3<cyclopropyl-2-oxo-2,3-dihydro-1H-benzo[d]imidazol-1-yl)phenyl) methyl propionate (88 mg, 0.23 mmol) and triethylamine (30 mg, 0.3 mmol) in dichloromethane (2 mL), cool to 0° C., add 2,6-dichlorobenzoyl chloride (48 mg, 0.25 mmol) dropwise to the reaction system, react at room temperature for 1 h. Add water (5 mL) to the reaction system, stand for layering, extract the water layer twice with dichloromethane (2 mL each time), combine the organic layers, wash the organic layers with water and saturated salt solution once, and dry over anhydrous sodium sulfate, filter and concentrate with vacuum to obtain the title compound (112 mg, 87%). ESI-QQQ-MS: m/z 558 $[M+H]^+$.

Step 4

(S)-3-(4-(5-chloro-3-cyclopropyl-2-oxo-2,3-dihydro-1H-benzo[d]imidazol-1-yl)phenyl)-2-(2,6-dichlorobenzamido)propionic acid

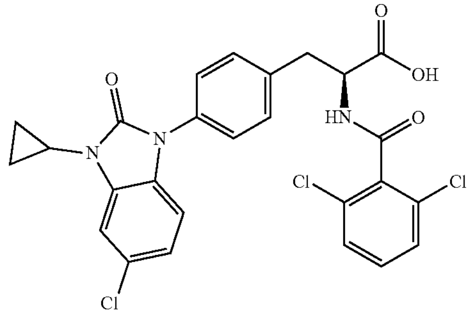 [SMILES: O=C(N[C@@H](Cc1ccc(-n2c(=O)n(C3CC3)c3cc(Cl)ccc32)cc1)C(=O)O)c1c(Cl)cccc1Cl]

Dissolve (S)-3-(4-5-chloro-3-cyclopropyl-2-oxo-2,3-dihydro-1H-benzo[d]imidazol-1-yl)phenyl)-2-(2,6-dichlorobenzamido)methyl propionate (95 mg, 0.17 mmol) in tetrahydrofuran (2 mL), then add 0.5 mol/L sodium hydroxide solution (0.6 mL, 0.29 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated saline solution once, dry over anhydrous sodium sulfate, filter and concentrate with vacuum, and purify the concentrate by RP-HPLC ($H_2O/CH_3CN$ system containing 0.1% formic acid) to obtain the title compound (57 mg, 62%). ESI-QQQ-MS: m/z 544 $[M+H]^+$. $^1H$ NMR (500 MHz, DMSO-d6): δ 12.76 (brs, 1H), 9.13 (d, J=8.4 Hz, 1H), 7.51-7.31 (m, 8H), 7.12-7.10 (m, 1H), 6.90 (d, J=8.4 Hz, 1H), 4.79-4.74 (m, 1H), 3.24 (dd, J=14.0, 4.5 Hz, 1H), 3.03-2.93 (m, 2H), 1.10-1.06 (m, 2H), 0.97-0.93 (m, 2H).

Example 24: Synthesis of Compound 27

Step 1

(S)-3-(4-(6-chloro-3-cyclopropyl-2-oxo-2,3-dihydro-1H-benzo[d]imidazol-1-yl)phenyl)-2-(triphenylmethylamino)methyl propionate

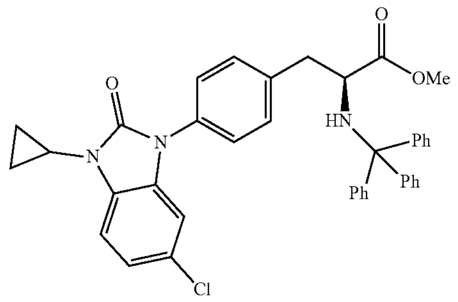 [SMILES: COC(=O)[C@H](Cc1ccc(-n2c(=O)n(C3CC3)c3ccc(Cl)cc32)cc1)NC(c1ccccc1)(c1ccccc1)c1ccccc1]

Dissolve P-20 (104 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=5:1) to obtain the title compound (182 mg, 58%). ESI-QQQ-MS: m/z 628 $[M+H]^+$.

Step 2

(S)-2-amino-3-(4-(6-chloro-3-cyclopropyl-2-oxo-2,3-dihydro-1H-benzo[d]imidazol-1-yl)phenyl) methyl propionate

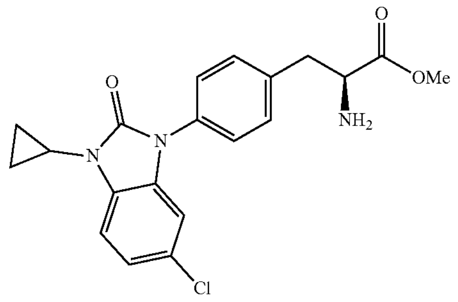 [SMILES: COC(=O)[C@@H](N)Cc1ccc(-n2c(=O)n(C3CC3)c3ccc(Cl)cc32)cc1]

Dissolve (S)-3-(4-(6-chloro-3-cyclopropyl-2-oxo-2,3-dihydro-1H-benzo[d]imidazol-1-yl)phenyl)-2-(triphenylmethylamino)methyl propionate (157 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (91 mg, 94%). ESI-QQQ-MS: m/z 386 $[M+H]^+$.

Step 3

(S)-3-(4-(6-chloro-3-cyclopropyl-2-oxo-2,3-dihydro-1H-benzo[d]imidazol-1-yl)phenyl)-2-(2,6-dichlorobenzamido)methyl propionate

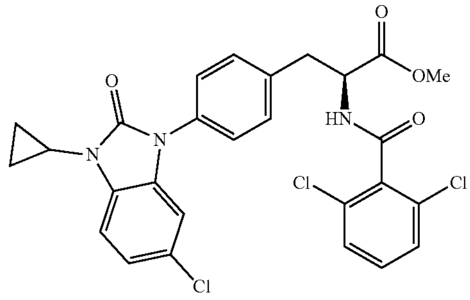 [SMILES: COC(=O)[C@H](Cc1ccc(-n2c(=O)n(C3CC3)c3ccc(Cl)cc32)cc1)NC(=O)c1c(Cl)cccc1Cl]

Dissolve (S)-2-amino-3-(4-(6-chloro-3-cyclopropyl-2-oxo-2,3-dihydro-1H-benzo[d]imidazol-1-yl)phenyl) methyl propionate (89 mg, 0.23 mmol) and triethylamine (30 mg, 0.3 mmol) in dichloromethane (2 mL), cool to 0° C., add 2,6-dichlorobenzoyl chloride (48 mg, 0.25 mmol) dropwise to the reaction system react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (118 mg, 92%). ESI-QQQ-MS: m/z 558 $[M+H]^+$.

Step 4

(S)-3-(4-(6-chloro-3-cyclopropyl-2-oxo-2,3-dihydro-1H-benzo[d]imidazol-1-yl)phenyl)-2-(2,6-dichlorobenzamido)propionic acid

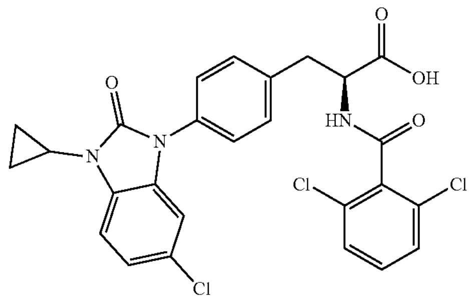 [SMILES: O=C(N[C@@H](Cc1ccc(-n2c(=O)n(C3CC3)c3ccc(Cl)cc32)cc1)C(=O)O)c1c(Cl)cccc1Cl]

Dissolve (S)-3-(4-(6-chloro-3-cyclopropyl-2-oxo-2,3-dihydro-1H-benzo[d]imidazol-1-yl)phenyl)-2-(2,6-dichlorobenzamido)methyl propionate (95 mg, 0.17 mmol) in tetrahydrofuran (2 mL), then add 0.5 mol/L sodium hydroxide solution (0.6 mL, 0.29 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (56 mg, 61%). ESI-QQQ-MS: m/z 544 $[M+H]^+$. $^1H$ NMR (500 MHz, DMSO-d6): δ 12.85 (brs, 1H), 9.12 (d, J=8.4 Hz, 1H), 7.50-7.48 (m, 2H), 7.45-7.38 (m, 5H), 7.30 (d, J=8.3 Hz, 1H), 7.20-7.18 (m, 1H), 6.87 (d, J=1.8 Hz, 1H), 4.80-4.75 (m, 1H), 3.26 (dd, J=14.0, 4.4 Hz, 1H), 3.01-2.95 (m, 2H), 1.09-1.05 (m, 2H), 0.97-0.93 (m, 2H).

Example 25: Synthesis of Compound 28

Step 1

(S)-3-(4-(7-chloro-3-cyclopropyl-2-oxo-2,3-dihydro-1H-benzo[d]imidazol-1-yl)phenyl)-2-(triphenylmethylamino)methyl propionate

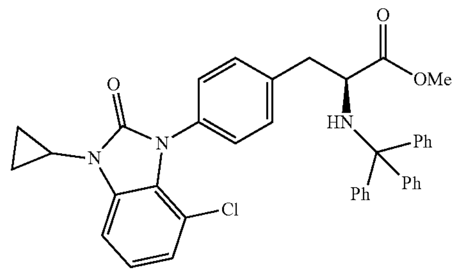 [SMILES: COC(=O)[C@H](Cc1ccc(-n2c(=O)n(C3CC3)c3cccc(Cl)c32)cc1)NC(c1ccccc1)(c1ccccc1)c1ccccc1]

Dissolve P-21 (104 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 361. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=5:1) to obtain the title compound (157 mg, 50%). ESI-QQQ-MS: m/z 628 $[M+H]^+$.

Step 2

(S)-2-amino-3-(4-(7-chloro-3-cyclopropyl-2-oxo-2,3-dihydro-1H-benzo[d]imidazol-1-yl)phenyl) methyl propionate

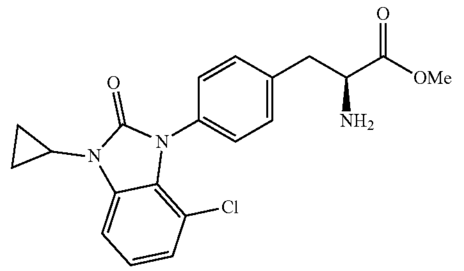 [SMILES: COC(=O)[C@@H](N)Cc1ccc(-n2c(=O)n(C3CC3)c3cccc(Cl)c32)cc1]

Dissolve (S)-3-(4-(7-chloro-3-cyclopropyl-2-oxo-2,3-dihydro-1H-benzo[d]imidazol-1-yl)phenyl)-2-(triphenylamino)methyl propionate (157 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (92 mg, 95%). ESI-QQQ-MS: m/z 386 $[M+H]^+$.

Step 3

(S)-3-(4-(7-chloro-3-cyclopropyl-2-oxo-2,3-dihydro-1H-benzo[d]imidazol-1-yl)phenyl)-2-(2,6-dichlorobenzamido)methyl propionate

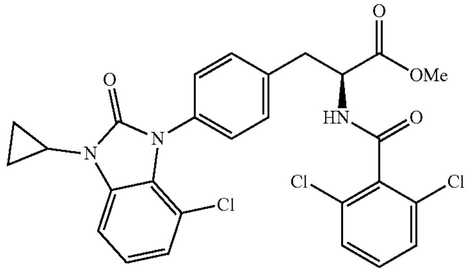 [SMILES: COC(=O)[C@H](Cc1ccc(-n2c(=O)n(C3CC3)c3cccc(Cl)c32)cc1)NC(=O)c1c(Cl)cccc1Cl]

Dissolve (S)-2-amino-3-(4-(7-chloro-3-cyclopropyl-2-oxo-2,3-dihydro-1H-benzo[d]imidazol-1-yl)phenyl) methyl propionate (89 mg, 0.23 mmol) and triethylamine (30 mg, 0.3 mmol) in dichloromethane (2 mL), cool to 0° C., add 2,6-dichlorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (115 mg, 90%). ESI-QQQ-MS: m/z 558 $[M+H]^+$.

Step 4

(S)-3-(4-(7-chloro-3-cyclopropyl-2-oxo-2,3-dihydro-1H-benzo[d]imidazol-1-yl)phenyl)-2-(2,6-dichlorobenzamido)propionic acid

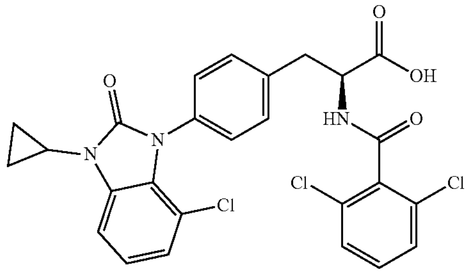 [SMILES: O=C(N[C@@H](Cc1ccc(-n2c(=O)n(C3CC3)c3cccc(Cl)c32)cc1)C(=O)O)c1c(Cl)cccc1Cl]

Dissolve (S)-3-(4-(7-chloro-3-cyclopropyl-2-oxo-2,3-dihydro-1H-benzo[d]imidazol-1-yl)phenyl)-2-(2,6-dichlorobenzamido)methyl propionate (95 mg, 0.17 mmol) in tetrahydrofuran (2 mL), then add 0.5 mol/L sodium hydroxide solution (0.6 mL, 0.29 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (49 mg, 53%). ESI-QQQ-MS: m/z 544 $[M+H]^+$. $^1H$ NMR (500 MHz, DMSO-d6): δ 12.84 (brs, 1H), 9.17 (d, J=8.2 Hz, 1H), 7.47-7.37 (m, 5H), 7.29 (t, J=7.8 Hz, 3H), 7.13 (t, J=8.0 Hz, 1H), 7.04 (d, J=8.1 Hz, 1H), 4.75-4.70 (m, 1H), 3.22 (dd, J=14.1, 4.2 Hz, 1H), 3.06-2.93 (m, 2H), 1.09-1.05 (m, 2H), 0.97-0.92 (m, 2H).

Example 26: Synthesis of Compound 29

Step 1

(S)-3-(4-(7-chloro-3-methyl-2-thio-2,3-dihydro-1H-benzo[d]imidazol-1-yl)phenyl)-2-(triphenylmethyl-amino)methyl propionate

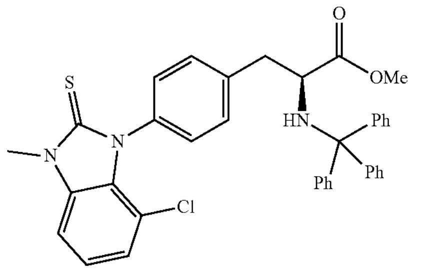 [SMILES: COC(=O)[C@H](Cc1ccc(-n2c(=S)n(C)c3cccc(Cl)c32)cc1)NC(c1ccccc1)(c1ccccc1)c1ccccc1]

Dissolve P-22 (99 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=5:1) to obtain the title compound (173 mg, 56%). ESI-QQQ-MS: m/z 618 $[M+H]^+$.

Step 2

(S)-2-amino-3-(4-(7-chloro-3-methyl-2-thio-2,3-dihydro-1H-benzo[d]imidazol-1-yl)phenyl)methyl propionate

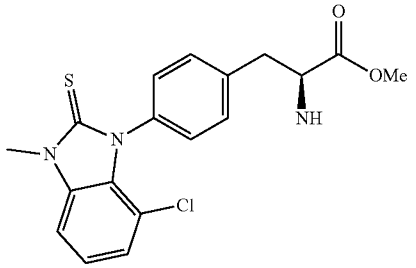 [SMILES: COC(=O)[C@@H](N)Cc1ccc(-n2c(=S)n(C)c3cccc(Cl)c32)cc1]

Dissolve (S)-3-(4-(7-chloro-3-methyl-2-thio-2,3-dihydro-1H-benzo[d]imidazol-1-yl)phenyl)-2-(triphenylamino) methyl propionate (155 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (86 mg, 92%). ESI-QQQ-MS: m/z 376 $[M+H]^+$.

Step 3

(S)-3-(4-(7-chloro-3-methyl-2-thio-2,3-dihydro-1H-benzo[d]imidazol-1-yl)phenyl)-2-(2-chloro-fluorobenzoylamino)methyl propionate

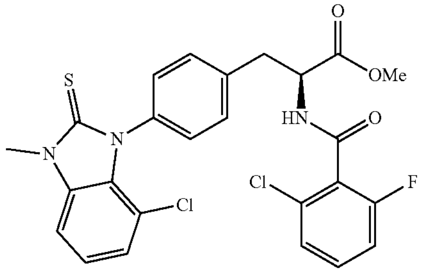

Dissolve (S)-2-amino-3-(4-(7-chloro-3-methyl-2-thio-2,3-dihydro-1H-benzo[d]imidazol-1-yl)phenyl) methyl propionate (86 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (110 mg, 90%). ESI-QQQ-MS: m/z 532 $[M+H]^+$.

Step 4

(S)-3-(4-(7-chloro-3-methyl-2-thio-2,3-dihydro-1H-benzo[d]imidazol-1-yl)phenyl)-2-(2-chloro-6-fluorobenzoylamino)propionic acid

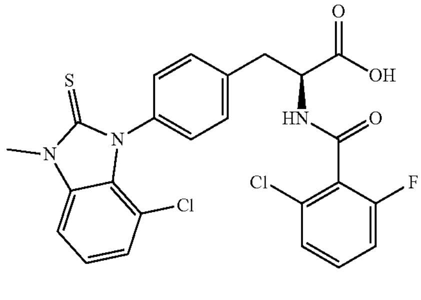 [SMILES: Cn1c(=S)n(-c2ccc(C[C@H](NC(=O)c3c(F)cccc3Cl)C(=O)O)cc2)c2c(Cl)cccc21]

Dissolve (S)-3-(4-(7-chloro-3-methyl-2-thio-2,3-dihydro-1H-benzo[d]imidazol-1-yl)phenyl)-2-(2-chloro-6-fluorobenzoylamino)methyl propionate (91 mg, 0.17 mmol) in tetrahydrofuran (2 mL), then add 0.5 mol/L sodium hydroxide solution (0.6 mL, 0.29 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (48 mg, 55%). ESI-QQQ-MS: m/z 518 $[M+H]^+$. $^1H$ NMR (500 MHz, DMSO-d6): δ 12.88 (brs, 1H), 9.08 (s, 1H), 7.57 (s, 1H), 7.44-7.12 (m, 9H), 4.65-4.63 (m, 1H), 3.76 (s, 3H), 3.16 (dd, J=14.1, 4.1 Hz, 1H), 2.92 (dd, J=13.9, 10.5 Hz, 1H).

Example 27: Synthesis of Compound 30

Step 1

(S)-3-(4-(3-cyclopropyl-7-fluoro-2-oxo-2,3-dihydro-1H-benzo[d]imidazol-1-yl)phenyl)-2-(triphenylmethylamino)methyl propionate

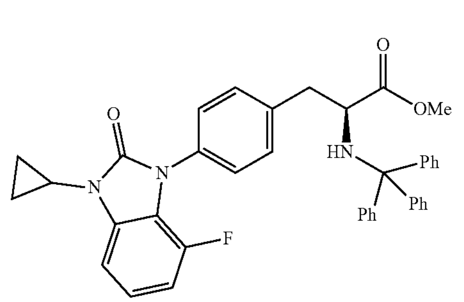 [SMILES: COC(=O)[C@H](Cc1ccc(-n2c(=O)n(C3CC3)c3cccc(F)c32)cc1)NC(c1ccccc1)(c1ccccc1)c1ccccc1]

Dissolve P-28 (96 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (193 mg, 63%/6). ESI-QQQ-MS: m/z 612 $[M+H]^+$.

Step 2

(S)-2-amino-3-(4-(3-cyclopropyl-7-fluoro-2-oxo-2,3-dihydro-1H-benzo[d]imidazol-1-yl)phenyl)m ethyl propionate

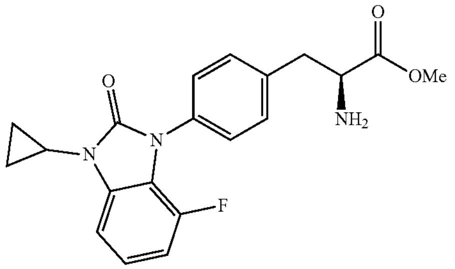 [SMILES: COC(=O)[C@@H](N)Cc1ccc(-n2c(=O)n(C3CC3)c3cccc(F)c32)cc1]

Dissolve (S)-3-(4-(6',7'-difluoro-2'-oxospiro[cyclopropane-1,3'-indoline]-1'-yl)phenyl)-2-(triphenylamino)methyl propionate (153 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (88 mg, 95%). ESI-QQQ-MS: m/z 370 $[M+H]^+$.

Step 3

(S)-2-(2-chloro-6-fluorobenzoylamino)-3-(4-(3-cyclopropyl-7-fluoro-2-oxo-2,3-dihydro-1H-benzo [d]imidazol-1-yl)phenyl)methyl propionate

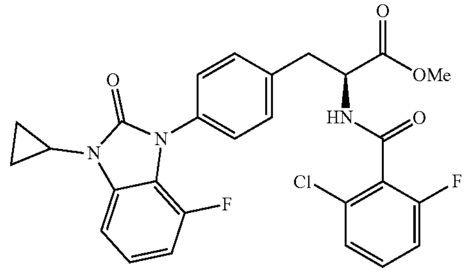 [SMILES: COC(=O)[C@H](Cc1ccc(-n2c(=O)n(C3CC3)c3cccc(F)c32)cc1)NC(=O)c1c(F)cccc1Cl]

Dissolve (S)-2-amino-3-(4-(6',7'-difluoro-2'-oxospiro[cyclopropane-1,3'-indoline]-1'-yl)phenyl))methyl propionate (85 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (109 mg, 90%). ESI-QQQ-MS: m/z 526 $[M+H]^+$.

Step 4

(S)-2-(2-chloro-6-fluorobenzoylamino)-3-(4-(3-cyclopropyl-7-fluoro-2-oxo-2,3-dihydro-1H-benzo[d]imidazol-1-yl)phenyl)propionic acid

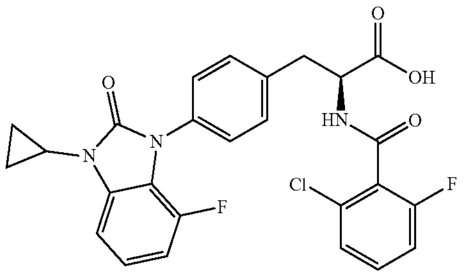 [SMILES: O=C(N[C@@H](Cc1ccc(-n2c(=O)n(C3CC3)c3cccc(F)c32)cc1)C(=O)O)c1c(F)cccc1Cl]

Dissolve (S)-2-(2-chloro-6-fluorobenzoylamino)-3-(4-(6',7'-difluoro-2'-oxospiro[cyclopropane-1,3'-indoline]-1'-yl)phenyl))methyl propionate (89 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (47 mg, 54%). ESI-QQQ-MS: m/z 512 $[M+H]^+$. $^1H$ NMR (500 MHz, DMSO-d6): δ 12.86 (brs, 1H), 9.18 (d, J=8.0 Hz, 1H), 7.48-7.22 (m, 7H), 7.17-7.10 (m, 2H), 6.99-6.82 (m, 1H), 4.71-4.68 (m, 1H), 3.22 (dd, J=14.1.4.2 Hz, 1H), 3.05-2.93 (m, 2H), 1.10-1.04 (m, 2H), 0.97-0.93 (m, 2H).

Example 28: Synthesis of Compound 31

Step 1

(S)-3-(4-(7-chloro-2-oxo-3-(tetrahydro-2H-pyran-4-yl)-2,3-dihydro-1H-benzo[d]imidazol-1-phenyl)-2-(triphenylamino)methyl propionate

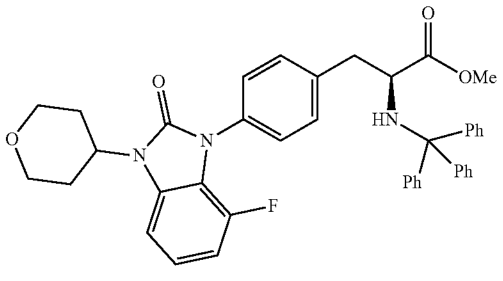 [SMILES: COC(=O)[C@H](Cc1ccc(-n2c(=O)n(C3CCOCC3)c3cccc(F)c32)cc1)NC(c1ccccc1)(c1ccccc1)c1ccccc1]

Dissolve P-23 (126 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 361. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=5:1) to obtain the title compound (175 mg, 0.52%). ESI-QQQ-MS: m/z 672 $[M+H]^+$.

Step 2

(S)-2-amino-3-(4-(7-chloro-2-oxo-3-(tetrahydro-2H-pyran-4-yl)-2,3-dihydro-1H-benzo[d]imidazol-1-yl)phenyl)methyl propionate

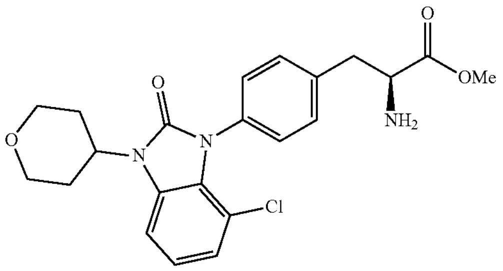 [SMILES: COC(=O)[C@@H](N)Cc1ccc(-n2c(=O)n(C3CCOCC3)c3cccc(Cl)c32)cc1]

Dissolve (S)-3-(4-(7-chloro-2-oxo-3-(tetrahydro-2H-pyran-4-yl)-2,3-dihydro-1H-benzo[d]imidazol-1-phenyl)-2-(triphenylamino)methyl propionate (168 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (102 mg, 95%). ESI-QQQ-MS: m/z 430 $[M+H]^+$.

Step 3

(S)-3-(4-(7-chloro-2-oxo-3-(tetrahydro-2H-pyran-4-yl)-2,3-dihydro-H-benzo[d]imidazol-1-phenyl)-2-(2-chloro-6-fluorobenzoylamino)methyl propionate

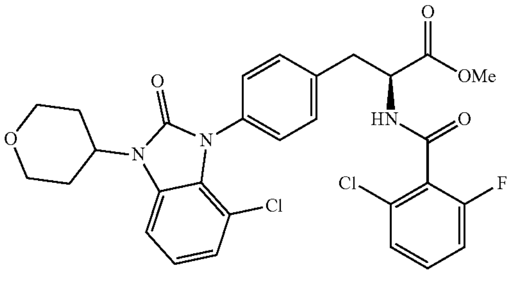 [SMILES: COC(=O)[C@H](Cc1ccc(-n2c(=O)n(C3CCOCC3)c3cccc(Cl)c32)cc1)NC(=O)c1c(F)cccc1Cl]

Dissolve (S)-2-amino-3-(4-(7-chloro-2-oxo-3-(tetrahydro-2H-pyran-4-yl)-2,3-dihydro-1H-benzo[d]imidazol-1-yl) phenyl)methyl propionate (99 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (119 mg, 88%). ESI-QQQ-MS: m/z 586 $[M+H]^+$.

Step 4

(S)-3-(4-(7-chloro-2-oxo-3-(tetrahydro-2H-pyran-4-yl)-2,3-dihydro-1H-benzo[d]imidazol-1-yl)phenyl)-2-(2-chloro-6-fluorobenzoylamino)propionic acid

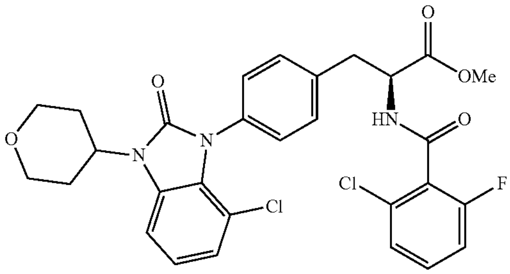 [SMILES: COC(=O)[C@H](Cc1ccc(-n2c(=O)n(C3CCOCC3)c3cccc(Cl)c32)cc1)NC(=O)c1c(F)cccc1Cl]

Dissolve (S)-3-(4-(7-chloro-2-oxo-3-(tetrahydro-2H-pyran-4-yl)-2,3-dihydro-1H-benzo[d]imidazol-1-phenyl)-2-(2-chloro-6-fluorobenzoylamino)methyl propionate (100 mg, 0.17 mmol) in tetrahydrofuran (2 mL), then add 0.5 mol/L sodium hydroxide solution (0.6 mL, 0.29 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (53 mg, 54%). ESI-QQQ-MS: m/z 572 $[M+H]^+$. $^1H$ NMR (500 MHz, DMSO-d6): δ 12.81 (brs, 1H), 9.18 (d, J=7.9 Hz, 1H), 7.56-7.19 (m, 8H), 7.15-7.03 (m, 2H), 4.74-4.68 (m, 1H), 4.55-4.47 (m, 1H), 4.00 (d, J=8.0 Hz, 2H), 3.49 (t, J=11.6 Hz, 2H), 3.26-3.21 (m, 1H), 3.07-2.95 (m, 1H), 2.47-2.42 (m, 2H), 1.76-1.70 (m, 2H).

Example 29: Synthesis of Compound 32

Step 1

(S)-3-(4-(7-chloro-3-(1-methylpiperidin-4-yl)-2-oxo-2,3-dihydro-1H-benzo[d]imidazol-1-yl)phenyl)-2-(triphenylamino)methyl propionate

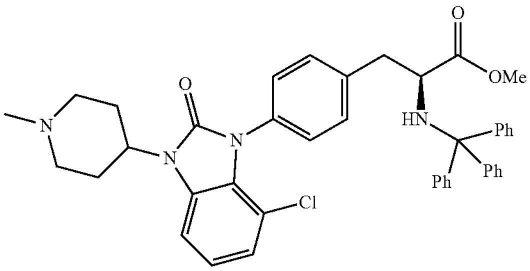 [SMILES: COC(=O)[C@H](Cc1ccc(-n2c(=O)n(C3CCN(C)CC3)c3cccc(Cl)c32)cc1)NC(c1ccccc1)(c1ccccc1)c1ccccc1]

Dissolve P-24 (133 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=5:1) to obtain the title compound (151 mg, 44%). ESI-QQQ-MS: m/z 685 $[M+H]^+$.

Step 2

(S)-2-amino-3-(4-(7-chloro-3-(1-methylpiperidin-4-yl)-2-oxo-2,3-dihydro-1H-benzo[d]imidazol-1-yl) phenyl)methyl propionate

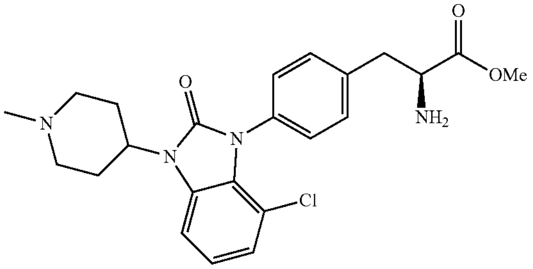 [SMILES: COC(=O)[C@@H](N)Cc1ccc(-n2c(=O)n(C3CCN(C)CC3)c3cccc(Cl)c32)cc1]

Dissolve (S)-3-(4-(7-chloro-3-(1-methylpiperidin-4-yl)-2-oxo-2,3-dihydro-1H-benzo[d]imidazol-1-yl)phenyl)-2-(triphenylamino)methyl propionate (171 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (104 mg, 94%). ESI-QQQ-MS: m/z 443 $[M+H]^+$.

Step 3

(S)-3-(4-(7-chloro-3-(1-methylpiperidin-4-yl)-2-oxo-2,3-dihydro-1H-benzo[d]imidazol-1-yl)phenyl)-2-(2-chloro-6-fluorobenzoylamino)methyl propionate

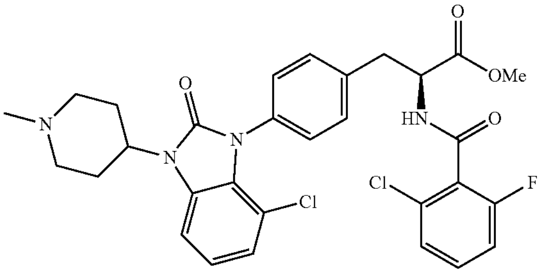

Dissolve (S)-2-amino-3-(4-(7-chloro-3-(1-methylpiperidin-4-yl)-2-oxo-2,3-dihydro-1H-benzo[d]imidazol-1-yl) phenyl)methyl propionate (102 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (117 mg, 85%). ESI-QQQ-MS: m/z 599 $[M+H]^+$.

Step 4

(S)-3-(4-(7-chloro-3-(1-methylpiperidin-4-yl)-2-oxo-2,3-dihydro-1H-benzo[d]imidazol-1-yl)phenyl)-2-(2-chloro-6-fluorobenzoylamino)propionic acid

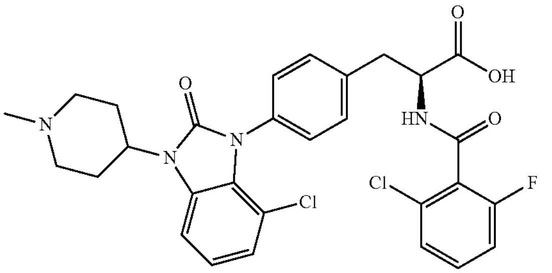 [SMILES: CN1CCC(n2c(=O)n(-c3ccc(C[C@H](NC(=O)c4c(F)cccc4Cl)C(=O)O)cc3)c3c(Cl)cccc32)CC1]

Dissolve (S)-3-(4-(7-chloro-3-(1-methylpiperidin-4-yl)-2-oxo-2,3-dihydro-1H-benzo[d]imidazol-1-yl)phenyl)-2-(2-chloro-6-fluorobenzoylamino)methyl propionate (102 mg, 0.17 mmol) in tetrahydrofuran (2 mL), then add 0.5 mol/L sodium hydroxide solution (0.6 mL, 0.29 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (40 mg, 40%). ESI-QQQ-MS: m/z 585 $[M+H]^+$. $^1H$ NMR (500 MHz, DMSO-d6): δ 9.01 (d, J=7.6 Hz, 1H), 7.48-7.37 (m, 4H), 7.34-7.19 (m, 4H), 7.12-7.00 (m, 2H), 4.70-4.64 (m, 1H), 4.43-4.34 (m, 1H), 3.32-2.95 (m, 6H), 2.60-2.53 (m, 2H), 2.43 (s, 3H), 1.84-1.80 (m, 2H).

Example 30: Synthesis of Compound 33

Step 1

(S)-3-(4-(7-fluoro-3-methyl-2-oxo-2,3-dihydro-1H-benzo[d]imidazol-1-yl)phenyl)-2-(triphenylmethylamino)methyl propionate

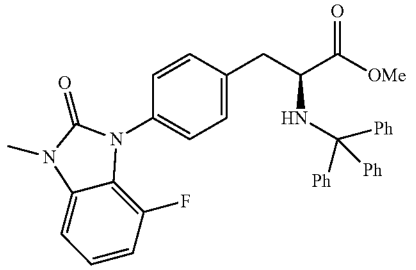 [SMILES: COC(=O)[C@H](Cc1ccc(-n2c(=O)n(C)c3cccc(F)c32)cc1)NC(c1ccccc1)(c1ccccc1)c1ccccc1]

Dissolve P-25 (83 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=5:1) to obtain the title compound (187 mg, 64%). ESI-QQQ-MS: m/z 586 $[M+H]^+$.

Step 2

(S)-2-amino-3-(4-(7-fluoro-3-methyl-2-oxo-2,3-dihydro-1H-benzo[d]imidazol-1-yl)phenyl)methyl propionate

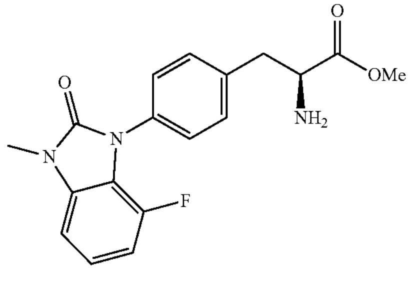 [SMILES: COC(=O)[C@@H](N)Cc1ccc(-n2c(=O)n(C)c3cccc(F)c32)cc1]

Dissolve (S)-3-(4-(7-fluoro-3-methyl-2-oxo-2,3-dihydro-1H-benzo[d]imidazol-1-yl)phenyl)-2-(triphenylamino) methyl propionate (146 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (81 mg, 94%). ESI-QQQ-MS: m/z 344 $[M+H]^+$.

Step 3

(S)-2-(2-chloro-6-fluorobenzoylamino)-3-(4-(7-fluoro-3-methyl-2-oxo-2,3-dihydro-1H-benzo[d]imidazol-1-yl)phenyl)methyl propionate

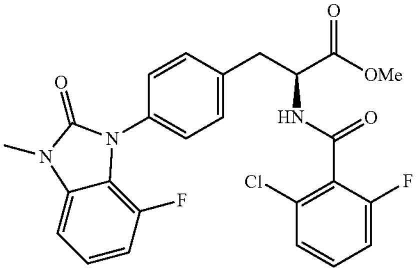 [SMILES: COC(=O)[C@H](Cc1ccc(-n2c(=O)n(C)c3cccc(F)c32)cc1)NC(=O)c1c(F)cccc1Cl]

Dissolve (S)-2-amino-3-(4-(7-fluoro-3-methyl-2-oxo-2,3-dihydro-H-benzo[d]imidazol-1-yl)phenyl) methyl propionate (79 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (103 mg, 90%). ESI-QQQ-MS: m/z 500 $[M+H]^+$.

Step 4

(S)-2-(2-chloro-4-fluorobenzoylamino)-3-(4-(7-fluoro-3-methyl-2-oxo-2,3-dihydro-1H-benzo[d]imidazol-1-yl)phenyl)propionic acid

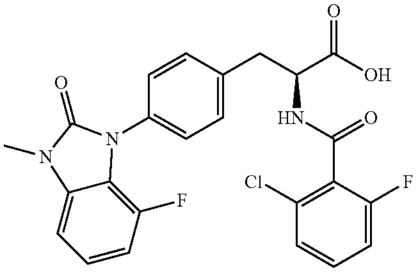 [SMILES: Cn1c(=O)n(-c2ccc(C[C@H](NC(=O)c3c(F)cccc3Cl)C(=O)O)cc2)c2c(F)cccc21]

Dissolve (S)-2-(2-chloro-6-fluorobenzoylamino)-3-(4-(7-fluoro-3-methyl-2-oxo-2,3-dihydro-1H-benzo[d]imidazol-1-yl)phenyl)methyl propionate (85 mg, 0.17 mmol) in tetrahydrofuran (2 mL), then add 0.5 mol/L sodium hydroxide solution (0.6 mL, 0.29 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (56 mg, 68%). ESI-QQQ-MS: m/z 486 $[M+H]^+$. $^1H$ NMR (500 MHz, DMSO-d6): δ 12.84 (brs, 1H), 9.18 (d, J=8.1 Hz, 1H), 7.47-7.36 (m, 5H), 7.33-7.23 (m, 2H), 7.14-7.10 (m, 2H), 6.96-6.88 (m, 1H), 4.73-4.65 (m, 1H), 3.40 (s, 3H), 3.25-3.18 (m, 1H), 3.01 (dd, J=13.9, 10.3 Hz, 1H).

Example 31: Synthesis of Compound 34

Step 1

(S)-3-(4-(5,7-difluoro-3-methyl-2-oxo-2,3-dihydro-1H-benzo[d]imidazol-1-yl)phenyl)-2-(triphenylmethylamino)methyl propionate

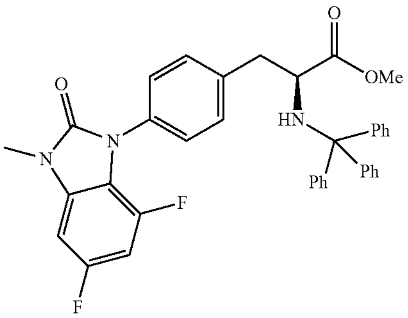 [SMILES: COC(=O)[C@H](Cc1ccc(-n2c(=O)n(C)c3cc(F)cc(F)c32)cc1)NC(c1ccccc1)(c1ccccc1)c1ccccc1]

Dissolve P-26 (92 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=5:1) to obtain the title compound (166 mg, 55%). ESI-QQQ-MS: m/z 604 $[M+H]^+$.

Step 2

(S)-2-amino-3-(4-(5,7-difluoro-3-methyl-2-oxo-2,3-dihydro-1H-benzo[d]imidazol-1-yl)phenyl)methyl propionate

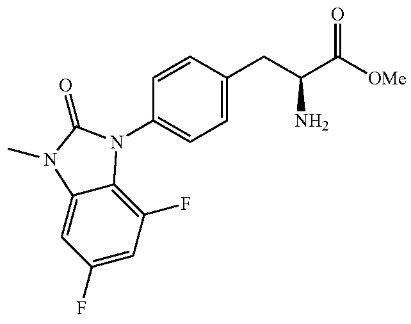 [SMILES: COC(=O)[C@@H](N)Cc1ccc(-n2c(=O)n(C)c3cc(F)cc(F)c32)cc1]

Dissolve (S)-3-(4-(5,7-difluoro-3-methyl-2-oxo-2,3-dihydro-H-benzo[d]imidazol-1-yl)phenyl)-2-(triphenylamino)methyl propionate (151 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (86 mg, 95%). ESI-QQQ-MS: m/z 362 $[M+H]^+$.

Step 3

(S)-2-(2-chloro-6-fluorobenzoylamino)-3-(4-(5,7-difluoro-3-methyl-2-oxo-2,3-dihydro-1H-benzo[d]imidazol-1-yl)phenyl)methyl propionate

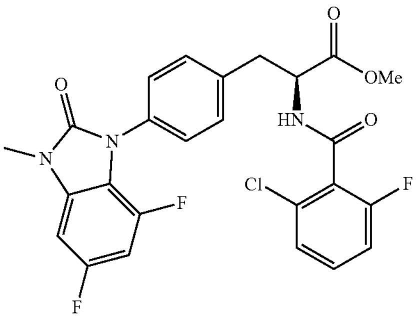 [SMILES: COC(=O)[C@H](Cc1ccc(-n2c(=O)n(C)c3cc(F)cc(F)c32)cc1)NC(=O)c1c(F)cccc1Cl]

Dissolve (S)-2-amino-3-(4-(5,7-difluoro-3-methyl-2-oxo-2,3-dihydro-H-benzo[d]imidazol-1-yl)phenyl) methyl propionate (83 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution one, and dry over anhydrous sodium sulfate, filter and concentrate with vacuum to obtain the title compound (105 mg, 88%). ESI-QQQ-MS: m/z 518 $[M+H]^+$.

Step 4

(S)-2-(2-chloro-6-fluorobenzoylamino)-3-(4-(5,7-difluoro-3-methyl-2-oxo-2,3-dihydro-H-benzo[d]imidazol-1-yl)phenyl)propionic acid

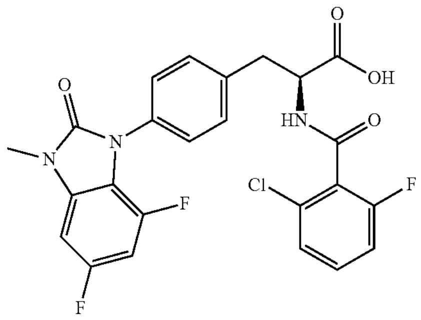 [SMILES: Cn1c(=O)n(-c2ccc(C[C@H](NC(=O)c3c(F)cccc3Cl)C(=O)O)cc2)c2c(F)cc(F)cc21]

Dissolve (S)-2-(2-chloro-6-fluorobenzoylamino)-3-(4-(5,7-difluoro-3-methyl-2-exo-2,3-dihydro-1H-benzo[d]imidazol-1-yl)phenyl)methyl propionate (88 mg, 0.17 mmol) in tetrahydrofuran (2 mL), then add 0.5 mol/L sodium hydroxide solution (0.6 mL, 0.29 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (50 mg, 59%). ESI-QQQ-MS: m/z 504 $[M+H]^+$. $^1H$ NMR (500 MHz, DMSO-d6) 12.52 (brs, 1H), 9.15 (d, J=8.1 Hz, 1H), 7.46-7.16 (m, 8H), 6.99-6.92 (m, 1H), 4.72-4.68 (m, 1H), 3.40-3.36 (m, 4H), 3.25-3.21 (m, 2H), 3.03-2.96 (m, 1H).

Example 32: Synthesis of Compound 35

Step 1

(S)-3-(4-(5,6-dichloro-3-methyl-2-oxo-2,3-dihydro-1H-benzo[d]imidazol-1-yl)phenyl)-2-(triphenylmethylamino)methyl propionate

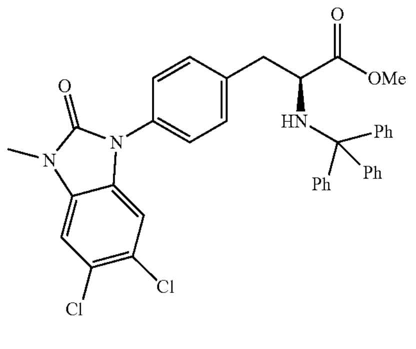 [SMILES: COC(=O)[C@H](Cc1ccc(-n2c(=O)n(C)c3cc(Cl)c(Cl)cc32)cc1)NC(c1ccccc1)(c1ccccc1)c1ccccc1]

Dissolve P-27 (109 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 361. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=5:1) to obtain the title compound (207 mg, 65%). ESI-QQQ-MS: m/z 636 $[M+H]^+$.

Step 2

(S)-2-amino-3-(4-(5,6-dichloro-3-methyl-2-oxo-2,3-dihydro-1H-benzo[d]imidazol-1-yl)phenyl)methyl propionate

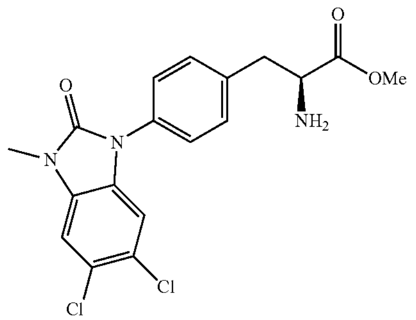 [SMILES: COC(=O)[C@@H](N)Cc1ccc(-n2c(=O)n(C)c3cc(Cl)c(Cl)cc32)cc1]

Dissolve (S)-3-(4-(5,6-dichloro-3-methyl-2-oxo-2,3-dihydro-1H-benzo[d]imidazol-1-yl)phenyl)-2-(triphenylamino)methyl propionate (159 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (94 mg, 95%). ESI-QQQ-MS: m/z 394 $[M+H]^+$.

Step 3

(S)-2-(2-chloro-6-fluorobenzoylamino)-3-(4-(5,6-dichloro-3-methyl-2-oxo-2,3-dihydro-1H-benzo[d]imidazol-1-yl)phenyl)methyl propionate

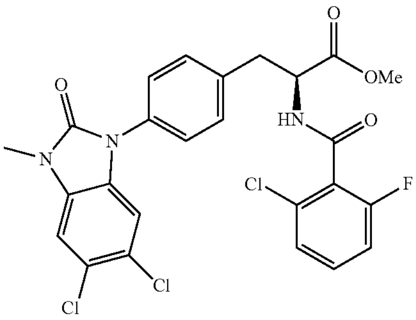 [SMILES: COC(=O)[C@H](Cc1ccc(-n2c(=O)n(C)c3cc(Cl)c(Cl)cc32)cc1)NC(=O)c1c(F)cccc1Cl]

Dissolve (S)-2-amino-3-(4-(5,6-dichloro-3-methyl-2-oxo-2,3-dihydro-1H-benzo[d]imidazol-1-yl)phenyl) methyl propionate (91 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (110 mg, 87%). ESI-QQQ-MS m/z 550 $[M+H]^+$.

Step 4

(S)-2-(2-chloro-6-fluorobenzoylamino)-3-(4-(5,6-dichloro-3-methyl-2-oxo-2,3-dihydro-H-benzo[d]imidazol-1-yl)phenyl)propionic acid

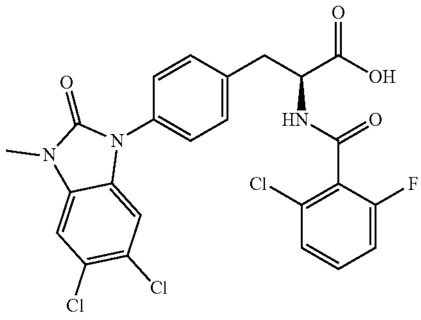 [SMILES: Cn1c(=O)n(-c2ccc(C[C@H](NC(=O)c3c(F)cccc3Cl)C(=O)O)cc2)c2cc(Cl)c(Cl)cc21]

Dissolve (S)-2-(2-chloro-6-fluorobenzoylamino)-3-(4-(5,6-dichloro-3-methyl-2-oxo-2,3-dihydro-H-benzo[d]imidazol-1-yl)phenyl)methyl propionate (94 mg, 0.17 mmol) in tetrahydrofuran (2 mL), then add 0.5 mol/L sodium hydroxide solution (0.6 mL, 0.29 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (54 mg, 59%). ESI-QQQ-MS: m/z 536 $[M+H]^+$. $^1H$ NMR (500 MHz, DMSO-d6): δ 12.87 (s, 1H), 9.14 (d, J=8.3 Hz, 1H), 7.63 (s, 1H), 7.52-7.42 (m, 5H), 7.33-7.21 (m, 2H), 7.05 (s, 1H), 4.77-4.72 (m, 1H), 3.40 (s, 3H), 3.27 (dd, J=14.0, 4.5 Hz, 1H), 3.00 (dd, J=13.9, 10.5 Hz, 1H).

Example 33: Synthesis of Compound 36

Step 1

(S)-3-(4-(6,7-difluoro-3-methyl-2-oxo-2,3-dihydro-H-benzo[d]imidazol-1-yl)phenyl)-2-(triphenylmethylamino)methyl propionate

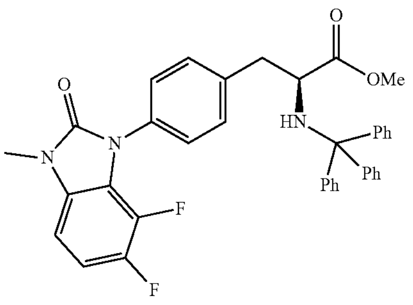 [SMILES: COC(=O)[C@H](Cc1ccc(-n2c(=O)n(C)c3ccc(F)c(F)c32)cc1)NC(c1ccccc1)(c1ccccc1)c1ccccc1]

Dissolve P-29 (92 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (196 mg, 65%). ESI-QQQ-MS: m/z 604 $[M+H]^+$.

Step 2

(S)-2-amino-3-(4-(6,7-difluoro-3-methyl-2-oxo-2,3-dihydro-1H-benzo[d]imidazol-1-yl)phenyl)methyl propionate

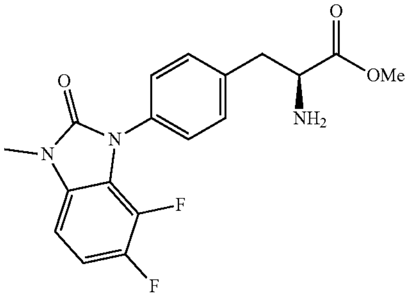 [SMILES: COC(=O)[C@@H](N)Cc1ccc(-n2c(=O)n(C)c3ccc(F)c(F)c32)cc1]

Dissolve (S)-3-(4-(6,7-difluoro-3-methyl-2-oxo-2,3-dihydro-1H-benzo[d]imidazol-1-yl)phenyl)-2-(triphenylamino)methyl propionate (151 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (85 mg, 94%). ESI-QQQ-MS: m/z 362 $[M+H]^+$.

Step 3

(S)-2-(2-chloro-6-fluorobenzoylamino)-3-(4-(6,7-difluoro-3-methyl-2-exo-2,3-dihydro-1H-benzo[d]imidazol-1-yl)phenyl)methyl propionate

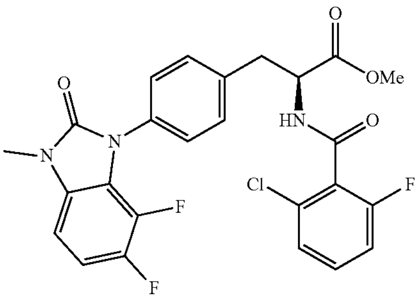 [SMILES: COC(=O)[C@H](Cc1ccc(-n2c(=O)n(C)c3ccc(F)c(F)c32)cc1)NC(=O)c1c(F)cccc1Cl]

Dissolve (S)-2-amino-3-(4-(6,7-difluoro-3-methyl-2-oxo-2,3-dihydro-1H-benzo[d]imidazol-1-yl)phenyl) methyl propionate (83 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (104 mg, 87%). ESI-QQQ-MS: m/z 518 $[M+H]^+$.

Step 4

(S)-2-(2-chloro-6-fluorobenzoylamino)-3-(4-(6,7-difluoro-3-methyl-2-exo-2,3-dihydro-1H-benzo[d]imidazol-1-yl)phenyl)propionic acid

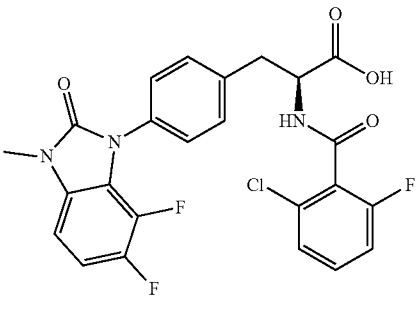 [SMILES: Cn1c(=O)n(-c2ccc(C[C@H](NC(=O)c3c(F)cccc3Cl)C(=O)O)cc2)c2c(F)c(F)ccc21]

Dissolve (S)-2-(2-chloro-6-fluorobenzoylamino)-3-(4-(6,7-difluoro-3-methyl-2-oxo-2,3-dihydro-1H-benzo[d]imidazol-1-yl)phenyl)methyl propionate (88 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (45 mg, 52%). ESI-QQQ-MS: m/z 504 $[M+H]^+$. $^1H$ NMR (500 MHz, DMSO-d6): δ 12.89 (brs, 1H), 9.17 (d, J=8.1 Hz, 1H), 7.47-7.40 (m, 5H), 7.31 (d, J=8.1 Hz, 1H), 7.28-7.15 (m, 2H), 7.09-7.07 (m, 1H), 4.74-4.69 (m, 1H), 3.39 (s, 3H), 3.24 (dd, J=14.1, 4.5 Hz, 1H), 3.01 (dd, J=14.1, 10.3 Hz, 1H).

Example 34: Synthesis of Compound 37

Step 1

(S)-3-(4-(4,5-difluoro-3-methyl-2-oxo-2,3-dihydro-1H-benzo[d]imidazol-1-yl)phenyl)-2-(triphenylmethylamino)methyl propionate

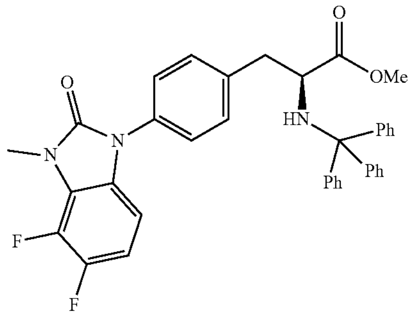 [SMILES: COC(=O)[C@H](Cc1ccc(-n2c(=O)n(C)c3c(F)c(F)ccc32)cc1)NC(c1ccccc1)(c1ccccc1)c1ccccc1]

Dissolve P-30 (92 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=4:1) to obtain the title compound (205 mg, 68%). ESI-QQQ-MS: m/z 604 $[M+H]^+$.

Step 2

(S)-2-amino-3-(4-(4,5-difluoro-3-methyl-2-oxo-2,3-dihydro-1H-benzo[d]imidazol-1-yl)phenyl)methyl propionate

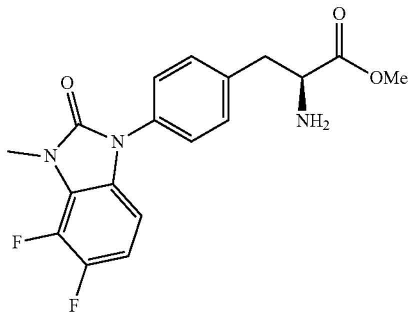 [SMILES: COC(=O)[C@@H](N)Cc1ccc(-n2c(=O)n(C)c3c(F)c(F)ccc32)cc1]

Dissolve (S)-3-(4-(4,5-difluoro-3-methyl-2-oxo-2,3-dihydro-1H-benzo[d]imidazol-1-yl)phenyl)-2-(triphenylamino)methyl propionate (151 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (86 mg, 95%). ESI-QQQ-MS: m/z 362 $[M+H]^+$.

Step 3

(S)-2-(2-chloro-6-fluorobenzoylamino)-3-(4-(4,5-difluoro-3-methyl-2-oxo-2,3-dihydro-1H-benzo[d]imidazol-1-yl)phenyl)methyl propionate

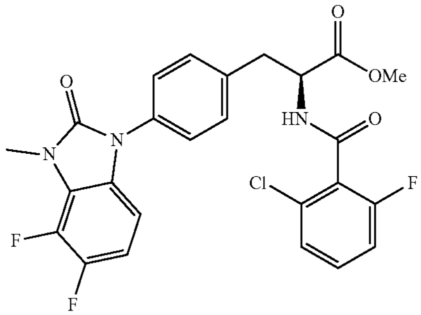 [SMILES: COC(=O)[C@H](Cc1ccc(-n2c(=O)n(C)c3c(F)c(F)ccc32)cc1)NC(=O)c1c(F)cccc1Cl]

Dissolve (S)-2-amino-3-(4-(4,5-difluoro-3-methyl-2-oxo-2,3-dihydro-1H-benzo[d]imidazol-1-yl)phenyl) methyl propionate (83 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (102 mg, 85%). ESI-QQQ-MS: m/z 518 $[M+H]^+$.

Step 4

(S)-2-(2-chloro-6-fluorobenzoylamino)-3-(4-(4,5-difluoro-3-methyl-2-oxo-2,3-dihydro-1H-benzo[d]imidazol-1-yl)phenyl)propionic acid

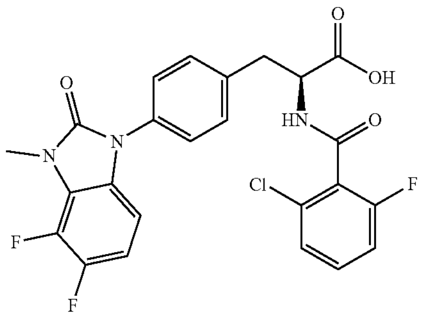 [SMILES: Cn1c(=O)n(-c2ccc(C[C@H](NC(=O)c3c(F)cccc3Cl)C(=O)O)cc2)c2ccc(F)c(F)c21]

Dissolve (S)-2-(2-chloro-6-fluorobenzoylamino)-3-(4-(4,5-difluoro-3-methyl-2-oxo-2,3-dihydro-1H-benzo[d]imidazol-1-yl)phenyl)methyl propionate (88 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (48 mg, 55%). ESI-QQQ-MS: m/z 504 $[M+H]^+$. $^1H$ NMR (500 MHz, DMSO): δ 12.89 (s, 1H), 9.16 (d, J=7.5 Hz, 1H), 7.56-7.37 (m, 5H), 7.32-7.24 (n, 2H), 7.14-7.06 (m, 1H), 6.71 (d, J=6.1 Hz, 1H), 4.76-4.68 (m, 1H), 3.55 (s, 3H), 3.28-3.22 (m, 1H), 3.04-2.96 (m, 1H).

Example 35: Synthesis of Compound 38

Step 1

(S)-3-(4-(7-methoxy-3-methyl-2-oxo-2,3-dihydro-1H-benzo[d]imidazol-1-yl)phenyl)-2-(triphenyl methylamino)methyl propionate

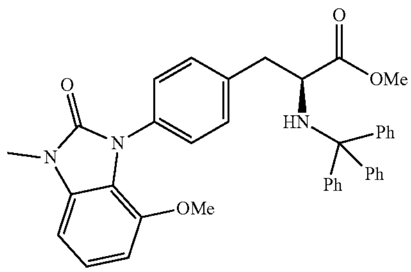 [SMILES: COC(=O)[C@H](Cc1ccc(-n2c(=O)n(C)c3cccc(OC)c32)cc1)NC(c1ccccc1)(c1ccccc1)c1ccccc1]

Dissolve P-31 (89 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=5:1) to obtain the title compound (155 mg, 52%). ESI-QQQ-MS: m/z 598 $[M+H]^+$.

Step 2

(S)-2-amino-3-(4-(7-methoxy-3-methyl-2-oxo-2,3-dihydro-1H-benzo[d]imidazo-1-yl)phenyl)methyl propionate

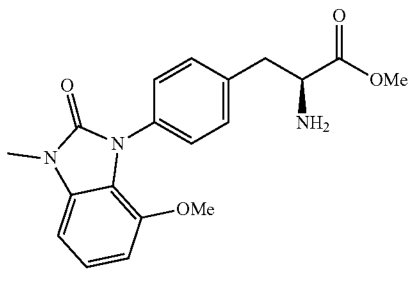 [SMILES: COC(=O)[C@@H](N)Cc1ccc(-n2c(=O)n(C)c3cccc(OC)c32)cc1]

Dissolve (S)-3-(4-(7-methoxy-3-methyl-2-oxo-2,3-dihydro-1H-benzo[d]imidazol-1-yl)phenyl)-2-(triphenyl amino)methyl propionate (149 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (85 mg, 96%). ESI-QQQ-MS: m/z 356 $[M+H]^+$.

Step 3

(S)-2-(2-chloro-6-fluorobenzoylamino)-3-(4-(7-methoxy-3-methyl-2-oxo-2,3-dihydro-1H-benzo[d]imidazol-1-yl)phenyl)methyl propionate

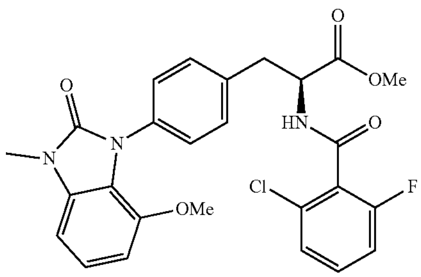 [SMILES: COC(=O)[C@H](Cc1ccc(-n2c(=O)n(C)c3cccc(OC)c32)cc1)NC(=O)c1c(F)cccc1Cl]

Dissolve (S)-2-amino-3-(4-(7-methoxy-3-methyl-2-oxo-2,3-dihydro-1H-benzo[d]imidazol-1-yl)phenyl) methyl propionate (82 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (104 mg, 88%). ESI-QQQ-MS: m/z 512 $[M+H]^+$.

Step 4

(S)-2-(2-chloro-6-fluorobenzoylamino)-3-(4-(7-methoxy-3-methyl-2-oxo-2,3-dihydro-1H-benzo[d]imidazol-1-yl)phenyl)propionic acid

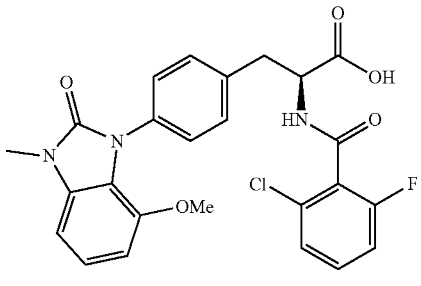 [SMILES: COc1cccc2c1n(-c1ccc(C[C@H](NC(=O)c3c(F)cccc3Cl)C(=O)O)cc1)c(=O)n2C]

Dissolve (S)-2-(2-chloro-6-fluorobenzoylamino)-3-(4-(7-methoxy-3-methyl-2-oxo-2,3-dihydro-1H-benzo[d]imidazol-1-yl)phenyl)methyl propionate (87 mg, 0.17 mmol) in tetrahydrofuran (2 mL), then add 0.5 mol/L sodium hydroxide solution (0.6 mL, 0.29 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (42 mg, 50%). ESI-QQQ-MS: m/z 498 $[M+H]^+$. $^1H$ NMR (500 MHz, DMSO-d6): δ 12.84 (brs, 1H), 9.19 (d, J=8.1 Hz, 1H), 7.47-7.42 (m, 1H), 7.36-7.31 (m, 3H), 7.27-7.25 (m, 3H), 7.11-7.09 (m, 1H), 6.89 (d, J=7.8 Hz, 1H), 6.76 (d, J=8.3 Hz, 1H), 4.72-4.68 (m, 1H), 3.56 (s, 3H), 3.36 (s, 3H), 3.21 (dd, J=14.1, 4.5 Hz, 1H), 3.01 (dd, J=14.0, 10.0 Hz, 1H).

Example 36: Synthesis of Compound 39

Step 1

(S)-3-(4-(6-(dimethylamino)-3-methyl-2-oxo-2,3-dihydro-1H-benzo[d]imidazol-1-yl)phenyl)-2-(triphenylmethylamino)methyl propionate

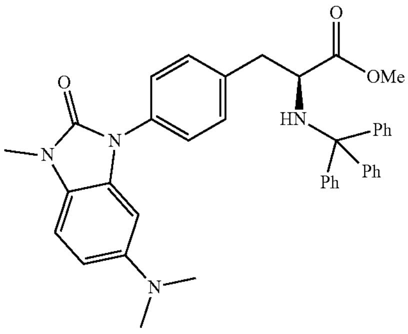 [SMILES: COC(=O)[C@H](Cc1ccc(-n2c(=O)n(C)c3ccc(N(C)C)cc32)cc1)NC(c1ccccc1)(c1ccccc1)c1ccccc1]

Dissolve P-32 (95 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=2:1) to obtain the title compound (147 mg, 48%). ESI-QQQ-MS: m/z 611 $[M+H]^+$.

Step 2

(S)-2-amino-3-(4-(6-(dimethylamino)-3-methyl-2-oxo-2,3-dihydro-1H-benzo[d]imidazol-1-yl)phenyl) methyl propionate

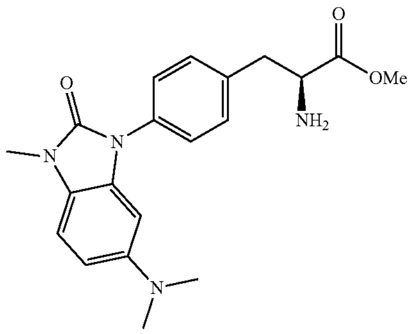 [SMILES: COC(=O)[C@@H](N)Cc1ccc(-n2c(=O)n(C)c3ccc(N(C)C)cc32)cc1]

Dissolve (S)-3-(4-(6-(dimethylamino)-3-methyl-2-oxo-2,3-dihydro-1H-benzo[d]imidazol-1-yl)phenyl)-2-(triphenylamino)methyl propionate (153 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (86 mg, 94%). ESI-QQQ-MS: m/z 369 $[M+H]^+$.

Step 3

(S)-2-(2-chloro-6-fluorobenzoylamino)-3-(4-(6-(dimethylamino)-3-methyl-2-oxo-2,3-dihydro-1H-benzo[d]imidazol-1-yl)phenyl)methyl propionate

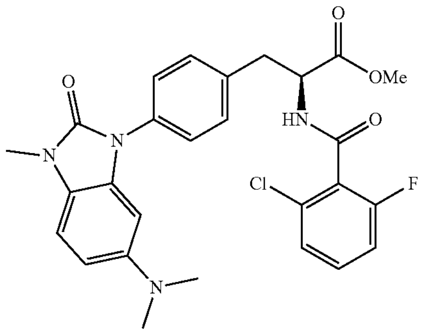

Dissolve (S)-2-amino-3-(4-(6-(dimethylamino)-3-methyl-2-oxo-2,3-dihydro-1H-benzo[d]imidazol-1-yl)phenyl) methyl propionate (85 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (111 mg, 92%). ESI-QQQ-MS: m/z 525 [M+H]$^+$.

Step 4

(S)-2-(2-chloro-6-fluorobenzoylamino)-3-(4-(6-(dimethylamino)-3-methyl-2-oxo-2,3-dihydro-1H-benzo[d]imidazol-1-yl)phenyl)propionic acid

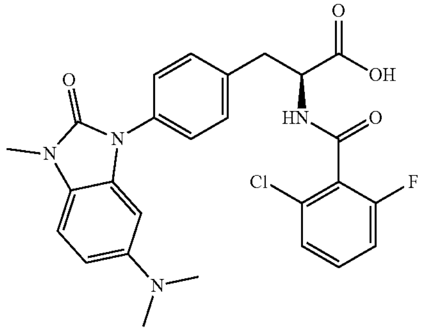 [SMILES: CN(C)c1ccc2c(c1)n(-c1ccc(C[C@H](NC(=O)c3c(F)cccc3Cl)C(=O)O)cc1)c(=O)n2C]

Dissolve (S)-2-(2-chloro-6-fluorobenzoylamino)-3-(4-(6-(dimethylamino)-3-methyl-2-oxo-2,3-dihydro-1H-benzo[d]imidazol-1-yl)phenyl)methyl propionate (89 mg, 0.17 mmol) in tetrahydrofuran (2 mL), then add 0.5 mol/L sodium hydroxide solution (0.6 mL, 0.29 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (37 mg, 42%). ESI-QQQ-MS: m/z 511 [M+H]$^+$. $^1$H NMR (500 MHz, DMSO-d6): δ 12.91 (brs, 1H), 9.18 (d, J=8.3 Hz, 1H), 7.52-7.39 (m, 5H), 7.33-7.09 (m, 3H), 7.02-6.21 (m, 2H), 4.77-4.73 (m, 1H), 3.26 (dd. J=14.1, 4.3 Hz, 1H), 3.00 (dd, J=14.0, 10.6 Hz, 1H), 2.89 (s, 6H), 2.54 (s, 3H).

Example 37: Synthesis of Compound 40

Step 1

(S)-3-(4-(5-(dimethylamino)-3-methyl-2-oxo-2,3-dihydro-1H-benzo[d]imidazol-1-yl)phenyl)-2-(triphenylmethylamino)methyl propionate

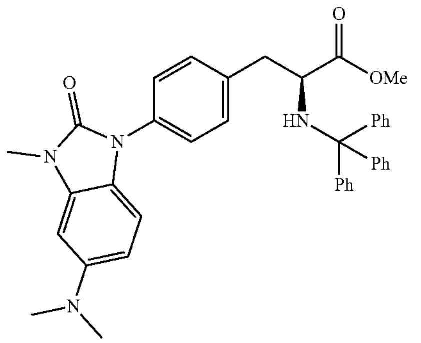 [SMILES: COC(=O)[C@H](Cc1ccc(-n2c(=O)n(C)c3cc(N(C)C)ccc32)cc1)NC(c1ccccc1)(c1ccccc1)c1ccccc1]

Dissolve P-33 (95 mg, 0.5 mmol) and P-1 (274 mg, 0.5 mmol) in anhydrous acetonitrile (3 mL), then add N,N-dimethylglycine hydrochloride (52 mg, 0.375 mmol), cesium carbonate (489 mg, 1.5 mmol) and cuprous iodide (24 mg, 0.125 mmol), under nitrogen protection, heat to 100° C., and react for 36 h. Cool, filter with purified siliceous earth, wash the filter cake twice with acetonitrile (1 mL each time), combine the filtrate, concentrate with vacuum, and purify the concentrate by silica gel column chromatography (petroleum ether/ethyl acetate=2:1) to obtain the title compound (153 mg, 50%). ESI-QQQ-MS: m/z 611 [M+H]$^+$.

Step 2

(S)-2-amino-3-(4-(5-(dimethylamino)-3-methyl-2-oxo-2,3-dihydro-1H-benzo[d]imidazol-1-yl)phenyl) methyl propionate

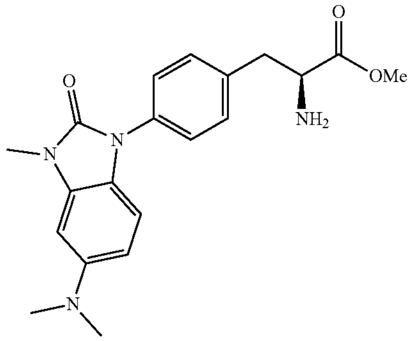 [SMILES: COC(=O)[C@@H](N)Cc1ccc(-n2c(=O)n(C)c3cc(N(C)C)ccc32)cc1]

Dissolve (S)-3-(4-(5-(dimethylamino)-3-methyl-2-oxo-2,3-dihydro-1H-benzo[d]imidazol-1-yl)phenyl)-2-(triphenylamino)methyl propionate (153 mg, 0.25 mmol) in dichloromethane (2 mL), then add trifluoroacetic acid (228 mg, 2 mmol) to the reaction system, and react at room temperature for 1 h. Concentrate with vacuum, add dichloromethane (3 mL) to the concentrate, adjust the pH to 8-9 with saturated sodium bicarbonate solution, stand for layering, extract the aqueous layer twice with dichloromethane, combine the organic layers, and wash the organic layer once with water and saturated salt solution respectively, dry over anhydrous sodium sulfate, filter and concentrate with vacuum to obtain the title compound (87 mg, 95%). ESI-QQQ-MS: m/z 369 [M+H]$^+$.

Step 3

(S)-2-(2-chloro-6-fluorobenzoylamino)-3-(4-(5-(dimethylamino)-3-methyl-2-oxo-2,3-dihydro-1H-benzo[d]imidazol-1-yl)phenyl)methyl propionate

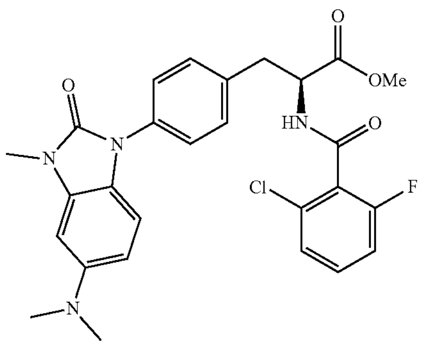 [SMILES: COC(=O)[C@H](Cc1ccc(-n2c(=O)n(C)c3cc(N(C)C)ccc32)cc1)NC(=O)c1c(F)cccc1Cl]

Dissolve (S)-2-amino-3-(4-(5-(dimethylamino)-3-methyl-2-oxo-2,3-dihydro-1H-benzo[d]imidazol-1-yl)phenyl) methyl propionate (85 mg, 0.23 mmol) and triethylamine (30 mg, 0.3 mmol) in dichloromethane (2 mL), cool to 0° C., add 2-chloro-6-fluorobenzoyl chloride (48 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (109 mg, 90%). ESI-QQQ-MS: m/z 525 $[M+H]^+$.

Step 4

(S)-2-(2-chloro-6-fluorobenzoylamino)-3-(4-(5-(dimethylamino)-3-methyl-2-oxo-2,3-dihydro-1H-benzo[d]imidazol-1-yl)phenyl)propionic acid

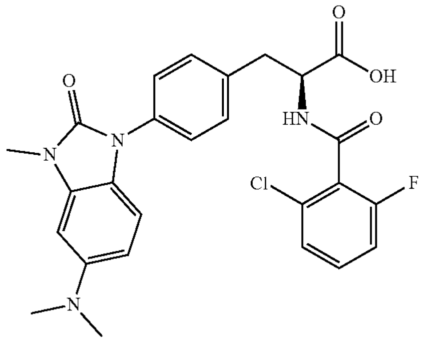 [SMILES: CN(C)c1ccc2c(c1)n(C)c(=O)n2-c1ccc(C[C@H](NC(=O)c2c(F)cccc2Cl)C(=O)O)cc1]

Dissolve (S)-2-(2-chloro-6-fluorobenzoylamino)-3-(4-(5-(dimethylamino)-3-methyl-2-oxo-2,3-dihydro-1H-benzo[d]imidazol-1-yl)phenyl)methyl propionate (89 mg, 0.17 mmol) in tetrahydrofuran (2 mL), then add 0.5 mol/L sodium hydroxide solution (0.6 mL, 0.29 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (35 mg, 40%). ESI-QQQ-MS: m/z 511 $[M+H]^+$. $^1H$ NMR (500 MHz, DMSO-d6): δ 12.93 (brs, 1H), 9.13 (d, J=8.2 Hz, 1H), 7.50-7.36 (m, 5H), 7.35-7.20 (m, 2H), 6.87 (d, J=8.6 Hz, 1H), 6.67 (d, J=2.2 Hz, 1H), 6.47 (dd, J=8.7, 2.3 Hz, 1H), 4.74-4.69 (m, 1H), 3.36 (s, 3H), 3.23 (dd, J=14.0, 4.6 Hz, 1H), 3.00 (dd, J=13.9, 10.2 Hz, 1H), 2.89 (s, 6H).

Example 38: Synthesis of Compound 41

Step 1

(S)-3-(4-(7-chloro-3-methyl-2-oxo-2,3-dihydro-1H-benzo[d]imidazol-1-yl)phenyl)-2-(2,4,6-trichlorobenzamido)methyl propionate

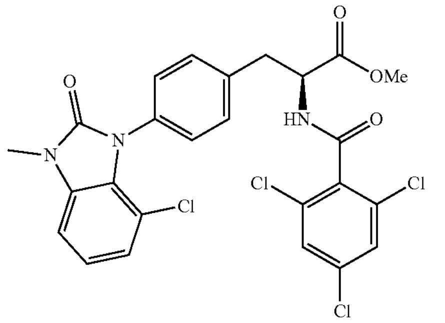 [SMILES: COC(=O)[C@H](Cc1ccc(-n2c(=O)n(C)c3cccc(Cl)c32)cc1)NC(=O)c1c(Cl)cc(Cl)cc1Cl]

Dissolve (S)-2-amino-3-(4-(7-chloro-3-methyl-2-oxo-2,3-dihydro-1H-benzo[d]imidazol-1-yl)phenyl) methyl propionate (83 mg, 0.23 mmol, the preparation process is detailed in Example 22) and triethylamine (30 mg, 0.3 mmol) in dichloromethane (2 mL), cool to 0° C., add intermediate P-34 (61 mg, 0.25 mmol) dropwise to the reaction system, react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (124 mg, 95%). ESI-QQQ-MS: m/z 566 $[M+H]^+$.

Step 2

(S)-3-(4-(7-chloro-3-methyl-2-oxo-2,3-dihydro-1H-benzo[d]imidazol-1-yl)phenyl)-2-(2,4,6-trichlorobenzamido)propionic acid

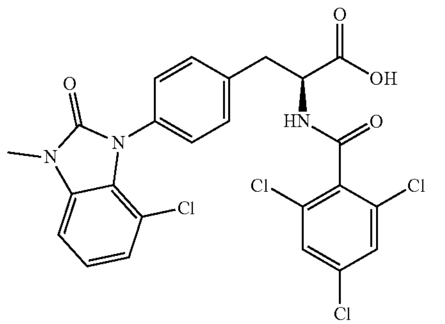 [SMILES: Cn1c(=O)n(-c2ccc(C[C@H](NC(=O)c3c(Cl)cc(Cl)cc3Cl)C(=O)O)cc2)c2c(Cl)cccc21]

Dissolve (S)-3-(4-(7-chloro-3-methyl-2-oxo-2,3-dihydro-1H-benzo[d]imidazol-1-yl)phenyl)-2-(2,4,6-trichlorobenzamido)methyl propionate (96 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (51 mg, 54%). ESI-QQQ-MS: m/z 552 $[M+H]^+$. $^1H$ NMR (500 MHz, DMSO-d6): δ 9.05 (d, J=7.8 Hz, 1H), 7.66 (s, 2H), 7.35 (dd, J=58.9, 8.0 Hz, 4H), 7.23 (d, J=7.8 Hz, 1H), 7.15-6.99 (m, 2H), 4.70-4.64 (m, 1H), 3.39 (s, 3H), 3.24 (dd, J=13.9, 3.8 Hz, 1H), 3.01 (dd, J=13.8, 10.0 Hz, 1H).

Example 39: Synthesis of Compound 42

Step 1

(S)-3-(4-(7-chloro-3-methyl-2-oxo-2,3-dihydro-1H-benzo[d]imidazol-1-yl)phenyl)-2-(2,6-dichloro-4-morpholinylbenzoylamino)methyl propionate

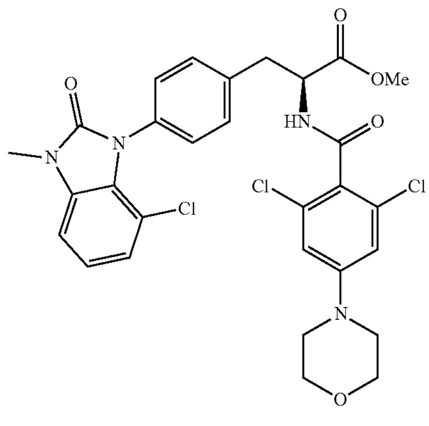 [SMILES: COC(=O)[C@H](Cc1ccc(-n2c(=O)n(C)c3cccc(Cl)c32)cc1)NC(=O)c1c(Cl)cc(N2CCOCC2)cc1Cl]

Dissolve (S)-2-amino-3-(4-(7'-chloro-2'-oxospiro[cyclopropane-1,3'-indoline]-1'-yl)phenyl) methyl propionate (83 mg, 0.23 mmol, the preparation process is detailed in Example 22) and triethylamine (30 mg, 0.3 mmol) in dichloromethane (2 mL), cool to 0° C., add the intermediate P-36 (74 mg, 0.25 mmol) dropwise to the reaction system, and the react at room temperature for 1 h. Add water (5 mL) to the reaction system, stand for layering, extract the aqueous layer twice with dichloromethane (2 mL each time), combine the organic layers, wash the organic layers with water and saturated salt solution once, and dry over anhydrous sodium sulfate, filter and concentrate with vacuum to obtain the title compound (113 mg, 80%). ESI-QQQ-MS: m/z 617 $[M+H]^+$.

Step 2

(S)-3-(4-(7-chloro-3-methyl-2-oxo-2,3-dihydro-1H-benzo[d]imidazol-1-yl)phenyl)-2-(2,6-dichloro-4-morpholinylbenzylamino)propionic acid

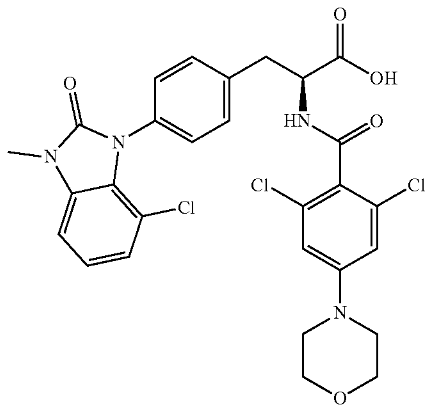 [SMILES: Cn1c(=O)n(-c2ccc(C[C@H](NC(=O)c3c(Cl)cc(N4CCOCC4)cc3Cl)C(=O)O)cc2)c2c(Cl)cccc21]

Dissolve (S)-3-(4-(7-chloro-3-methyl-2-oxo-2,3-dihydro-1H-benzo[d]imidazol-1-yl)phenyl)-2-(2,6-dichloro-4-morpholinylbenzoylamino)methyl propionate (105 mg, 0.17 mmol) in tetrahydrofuran (2 mL), then add 0.5 mol/L sodium hydroxide solution (0.4 mL, 0.2 mmol) to the reaction system, and react at room temperature for 2 h. Adjust the pH of the reaction system to 1-2 with 2 mol/L dilute hydrochloric acid, extract three times with dichloromethane (2 mL each time), combine the organic layers, wash the organic layers with water and saturated salt solution once, dry over anhydrous sodium sulfate, filter and concentrate with vacuum, and purify the concentrate by RP-HPLC ($H_2O/CH_3CN$ system containing 0.1% formic acid) to obtain the title compound (45 mg, 44%). ESI-QQQ-MS: m/z 603 $[M+H]^+$. $^1H$ NMR (500 MHz, DMSO-d6): δ 12.77 (brs, 1H), 8.91 (d, J=7.5 Hz, 1H), 7.43-7.41 (m, 2H), 7.31-7.22 (m, 3H), 7.16-7.01 (m, 2H), 6.93 (s, 2H), 4.68-4.64 (m, 1H), 3.70-3.68 (m, 4H), 3.39 (s, 3H), 3.21 (s, 1H), 3.19-3.17 (m, 4H), 3.04-2.99 (m, 1H).

Example: MADCAM-1/α4β7 Integrin Binding Inhibition Activity Evaluation Test (α4β7-MADCAM-1 ELISA)

Coat the 96-well microplate (Costar) with 50 μL of recombinant human MAdCAM-1 (R&D Systems) solution per well, and incubate overnight (12-18 hours) at 4° C. Wash three times with 150 μL of TBS buffer per well. Block plate with 150 μL per well with blocking buffer for 1 h at 37° C. Wash three times with 150 μL of TBS buffer per well. Dilute the recombinant human integrin α4β7 (R&D Systems) with TBS buffer containing 0.1% bovine serum albumin (BSA), then add to the 96 well plate with 50 μL per well. Add 1 μL of test compound or DMSO, cover, incubate at room temperature for 2 h, wash three times with 150 μL of TBS buffer per well. Dilute the anti-β7 antibody (R&D Systems) with 0.1% BSA TBS buffer, then add to the 96 well plate with 50 μL per well, cover, incubate at room temperature for 1 h, wash three times with 150 μL of TBS buffer per well. Add 50 μL of streptavidin-HRP (R&D Systems) per well, incubate at room temperature for 20 min, wash three times with 150 μL of TBS buffer per well. Add 50 μL of TMB substrate solution (Sigma) per well, incubate at room temperature for 5-30 min, and add 25 μL of stop solution per well to stop the reaction. Finally, measure absorbance at 450 nm with microplate reader (SpectraMax 340PC. Molecular Devices). Repeat the test to find the binding rate of cells at each concentration when the absorbance of the well without the test substance is used as 100%, and calculate the concentration $IC_{50}$ that causes 50% binding inhibition and summarize the results in Table 1.

It should be stated that, as a test compound, the free form of the compound synthesized in the above examples is used.

TABLE 1

Results of MAdCAM-1/α4β7 Integrin Binding Inhibition Activity

| Compound No. | $IC_{50}$ (nM) α4β7 |
|---|---|
| Example 1 | 14.29 |
| Example 2 | 2.57 |
| Example 3 | 5.48 |
| Example 4 | 2.54 |
| Example 5 | 2.87 |
| Example 6 | 5.81 |
| Example 7 | 16.11 |
| Example 8 | 17.59 |
| Example 9 | 95.48 |
| Example 10 | 38.84 |
| Example 11 | 3.05 |
| Example 12 | 4.15 |
| Example 13 | 8.02 |
| Example 14 | 6.21 |
| Example 15 | 5.62 |
| Example 16 | 0.75 |
| Example 17 | 64.21 |
| Example 19 | 11.41 |
| Example 20 | 4.15 |
| Example 21 | 23.75 |
| Example 22 | 1.19 |
| Example 23 | 143.4 |
| Example 24 | 5.67 |
| Example 25 | 7.50 |
| Example 26 | 160.1 |
| Example 27 | 8.81 |
| Example 28 | 10.89 |
| Example 29 | 18.14 |
| Example 30 | 1.83 |
| Example 31 | 5.34 |
| Example 32 | 4.19 |
| Example 33 | 2.70 |
| Example 34 | 10.46 |
| Example 35 | 0.45 |
| Example 36 | 1.51 |
| Example 37 | 5.09 |
| Example 38 | 27.91 |
| Example 39 | 3.65 |

As described above, the novel N-(benzoyl)-phenylalanine compounds of the present invention have excellent α4β7 integrin binding inhibitory activity. Therefore, the novel N-(benzoyl)-phenylalanine compounds of the present invention can provide therapeutic agents or prophylactic agents for α4β7-dependent autoimmune diseases and inflammatory bowel diseases (Crohn's disease and ulcerative colitis).

The compounds of the present invention have a high blood concentration or bioavailability when administered orally, and are useful as oral administration formulations.

In addition, the compounds of the present invention have good stability in acidic and alkaline solutions and can be used for the development of various dosage forms.

In addition to those examples described herein, according to the foregoing description, a variety of modifications of the present invention will be obvious to those skilled in the art. Such modification intentions also fall within the scope of the attached claims. Each reference cited in this application (including all patents, patent applications, journal articles, books, and any other publications) is incorporated herein by reference in its entirety.

The invention claimed is:

1. A compound as shown in general formula (1) or a pharmaceutically acceptable salt, ester, solvate, optical isomer, tautomer, isotope marker, or prodrug thereof, (1)

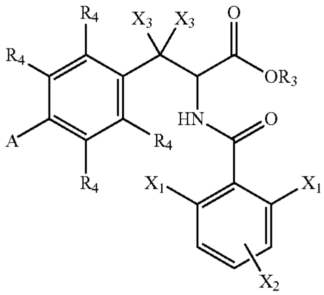

wherein:

$R_3$ is hydrogen;

each $R_4$ is independently hydrogen;

each $X_1$ is independently fluorine, chlorine, or bromine;

$X_2$ is hydrogen, halogen, di ($C_{1-6}$ alkyl) amino, or 3-7-membered heterocyclic alkyl;

each $X_3$ is independently hydrogen;

A is a group as shown in general formula (2-1), (2-2), or (2-3), (2-1)

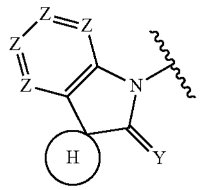

(2-2)

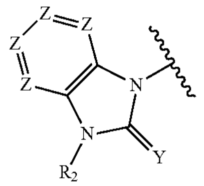

(2-3)

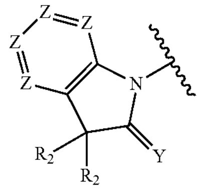

ring H is $C_{3-6}$ cyclic alkylene or 3-7 membered heterocyclic alkylene;

Y is O or S;

each Z is independently $CR_1$ or N;

if present, each $R_1$ is independently hydrogen, halogen, $C_{1-6}$ alkoxy, or di ($C_{1-6}$ alkyl) amino;

if present, each $R_2$ is independently $C_{1-6}$ alkyl, $C_{3-6}$ cyclic alkyl or 3-7 membered heterocyclic alkyl.

2. The compound or the pharmaceutically acceptable salt, ester, solvate, optical isomer, tautomer, isotope marker, or prodrug thereof according to claim 1, wherein each $X_1$ is independently fluorine or chlorine.

3. The compound or the pharmaceutically acceptable salt, ester, solvate, optical isomer, tautomer, isotope marker, or prodrug thereof according to claim 1, wherein $X_2$ is hydrogen or 3-7 membered heterocyclic alkyl.

4. The compound or the pharmaceutically acceptable salt, ester, solvate, optical isomer, tautomer, isotope marker, or prodrug thereof according to claim 1, wherein:

A is a group as shown in the general formula (2-1-1) or (2-1-1'), (2-1-1)

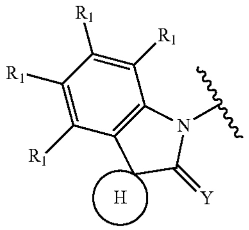

(2-1-1')

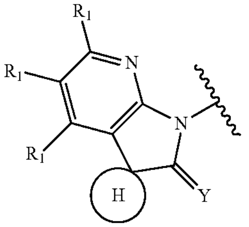

ring H is $C_{3-6}$ cyclic alkylene or 3-7-membered heterocyclic alkylene;

Y is O or S;

when A is a group as shown in general formula (2-1-1), two of the four $R_1$ are independently halogen, $C_{1-6}$ alkoxy, or di ($C_{1-6}$ alkyl) amino, and the rest are hydrogen;

alternatively, one of the four $R_1$ is halogen, $C_{1-6}$ alkoxy, or di ($C_{1-6}$ alkyl) amino, and the rest are hydrogen;

alternatively, all four $R_1$ are hydrogen;

when A is a group as shown in general formula (2-1-1'), two of the three $R_1$ are independently halogen, $C_{1-6}$ alkoxy, or di ($C_{1-6}$ alkyl) amino, and one is hydrogen;

alternatively, one of the three $R_1$ is halogen, $C_{1-6}$ alkoxy, or di ($C_{1-6}$ alkyl) amino, and the rest are hydrogen;

alternatively, all three $R_1$ are hydrogen.

5. The compound or the pharmaceutically acceptable salt, ester, solvate, optical isomer, tautomer, isotope marker, or prodrug thereof according to claim 1, wherein:

A is a group as shown in general formula (2-2-1), (2-2-1)

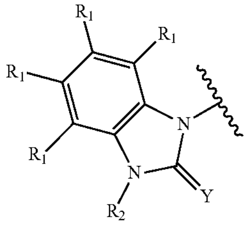

Y is O or S;

two of the four $R_1$ are independently halogen, $C_{1-6}$ alkoxy, or di ($C_{1-6}$ alkyl) amino, and the rest are hydrogen;

alternatively, one of the four $R_1$ is halogen, $C_{1-6}$ alkoxy, or di ($C_{1-6}$ alkyl) amino, and the rest are hydrogen;

$R_2$ is $C_{1-6}$ alkyl, $C_{3-6}$ cyclic alkyl or 3-7-membered heterocyclic alkyl.

6. The compound or the pharmaceutically acceptable salt, ester, solvate, optical isomer, tautomer, isotope marker, or prodrug thereof according to claim 1, wherein:

A is a group as shown in general formula (2-3-1), (2-3-1)

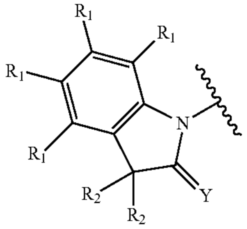

Y is O or S;

one of the four $R_1$ is halogen, $C_{1-6}$ alkoxy, or di ($C_{1-6}$ alkyl) amino, and the rest are hydrogen;

each $R_2$ is independently $C_{1-6}$ alkyl, $C_{3-6}$ cyclic alkyl or 3-7-membered heterocyclic alkyl.

7. A compound or pharmaceutically acceptable salt, ester, solvate, optical isomer, tautomer, isotope marker, or prodrug thereof having a structure selected from the group consisting of:

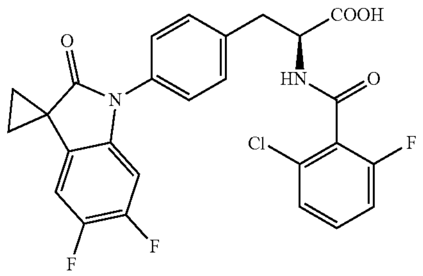

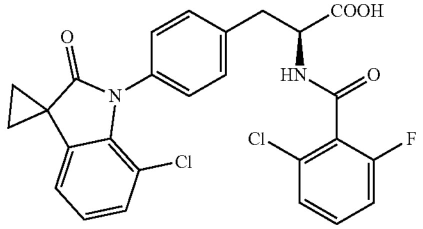

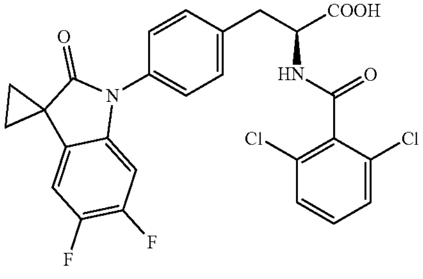

-continued
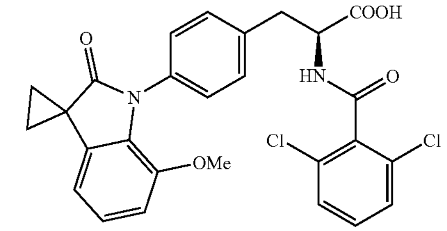
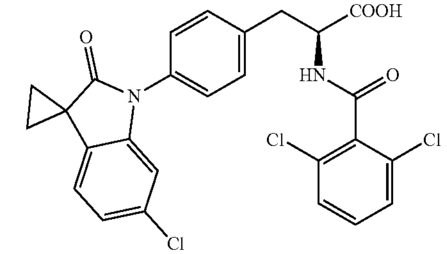
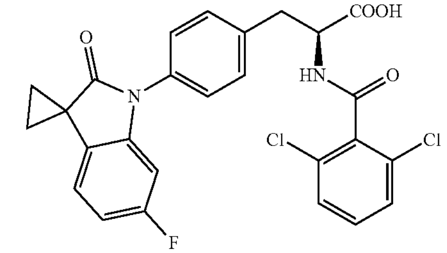
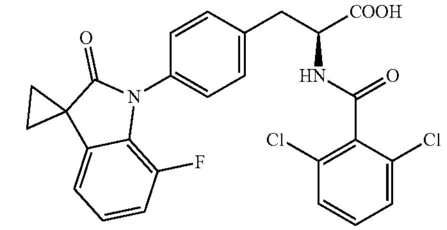
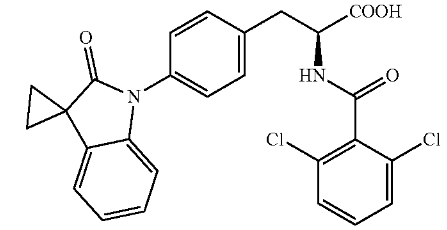
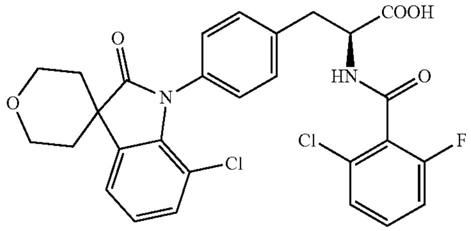
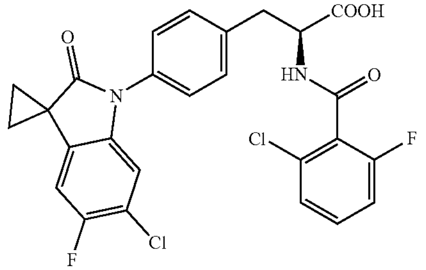
-continued
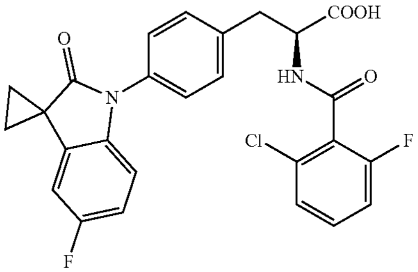
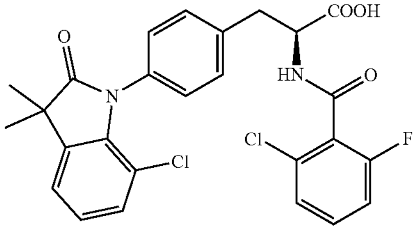
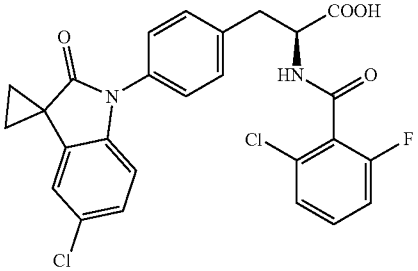
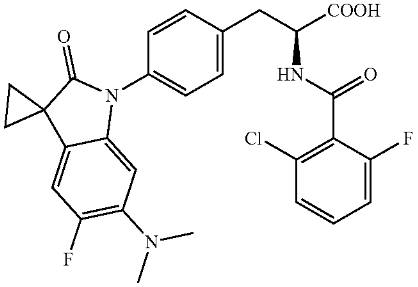
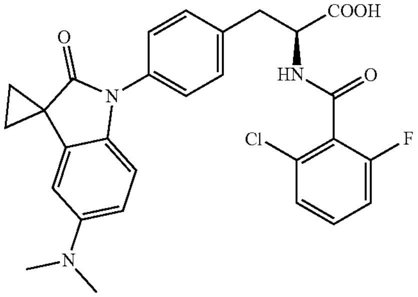
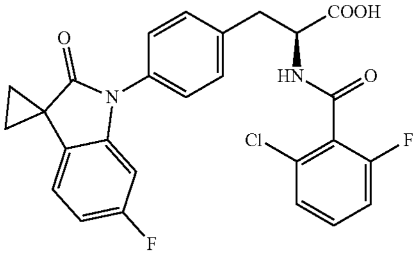

-continued
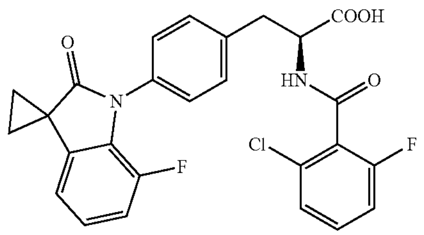
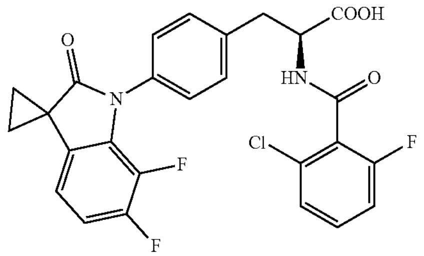
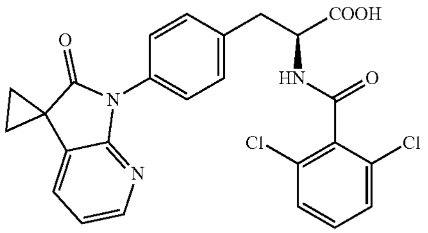
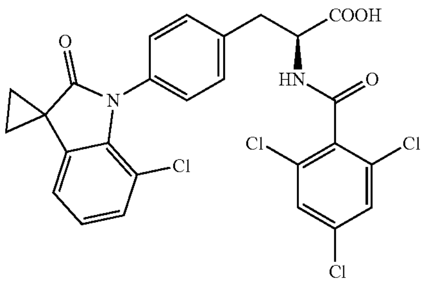
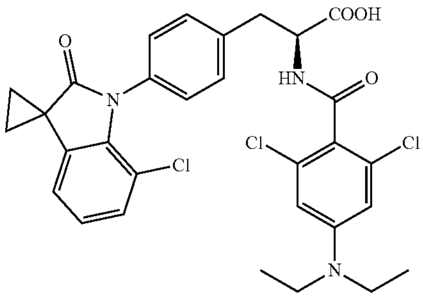
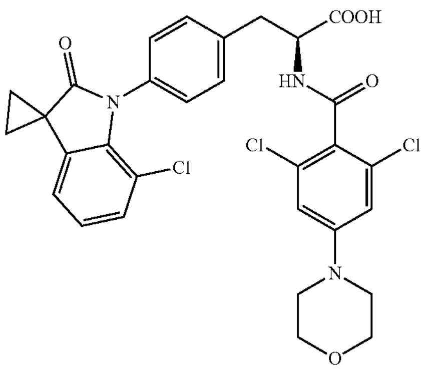
-continued
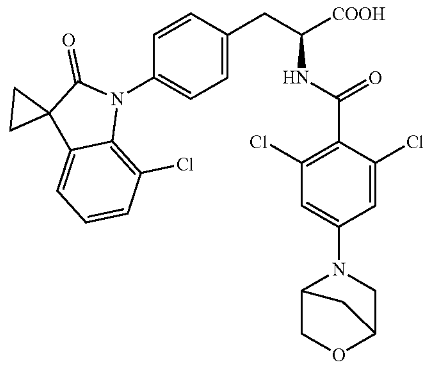
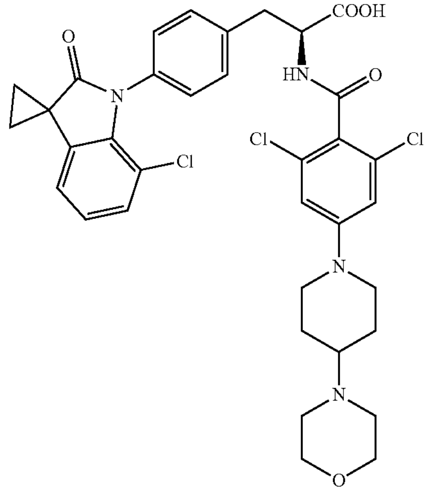
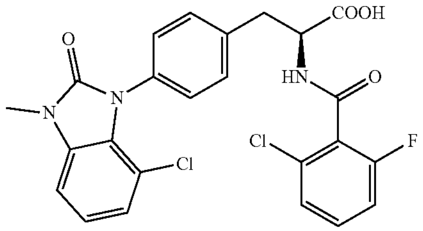
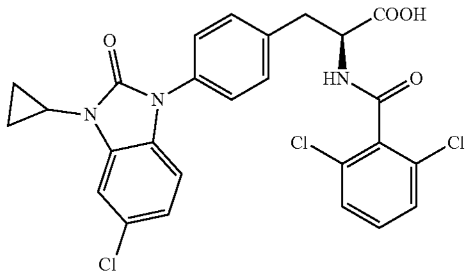
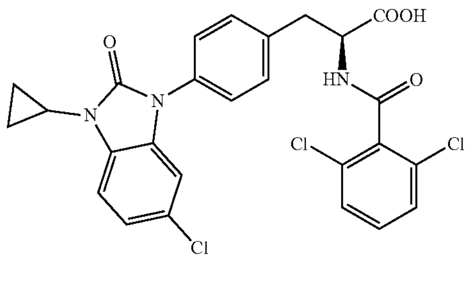

-continued
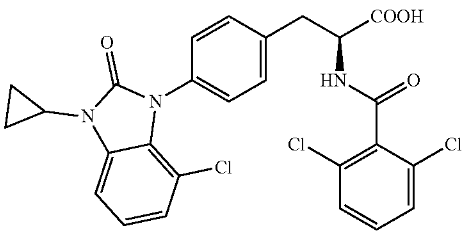
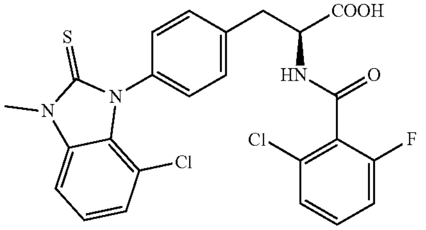
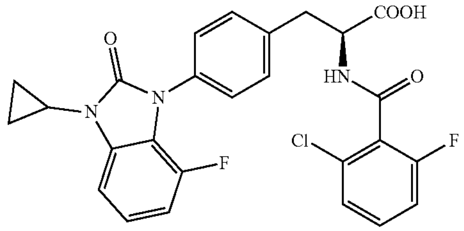
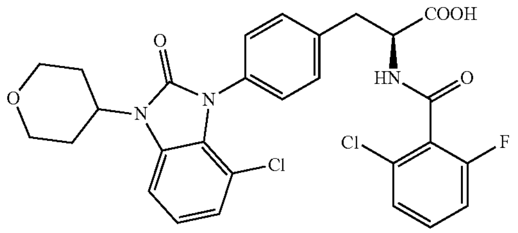
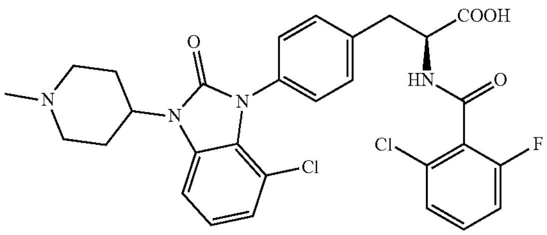
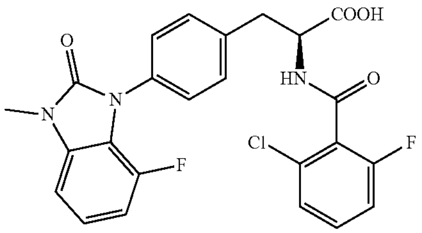
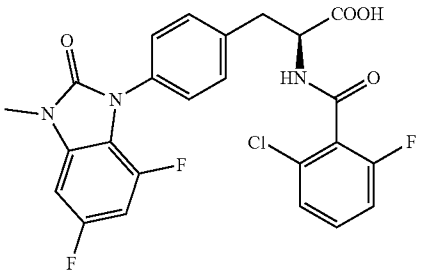
-continued
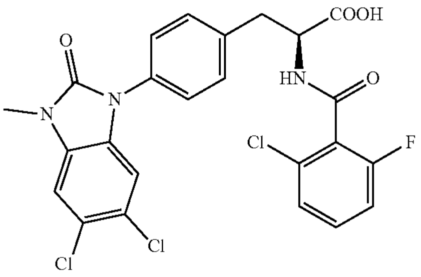
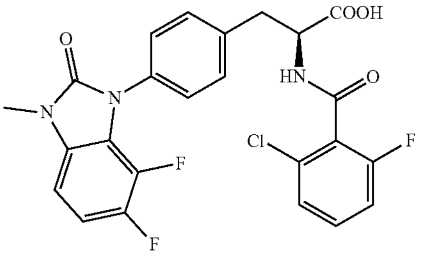
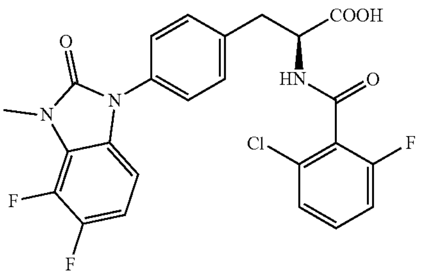
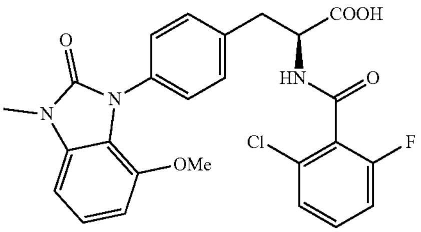
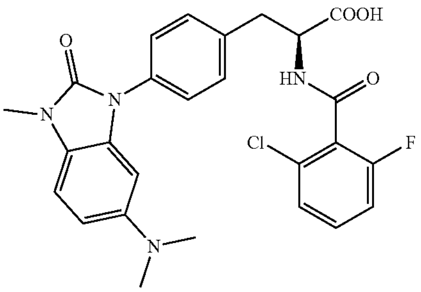
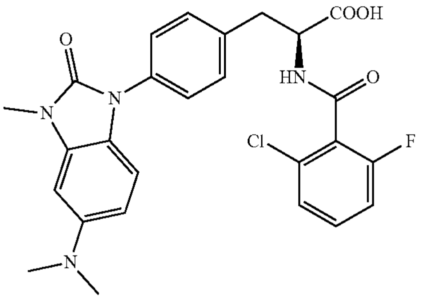

-continued

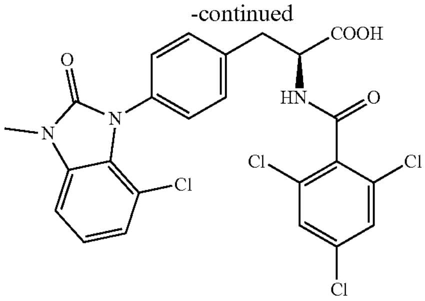

and

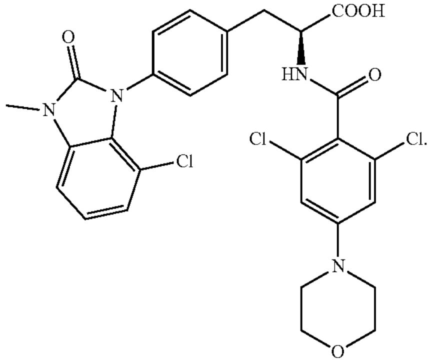

8. A pharmaceutical composition comprising the compound or the pharmaceutically acceptable salt, ester, solvate, optical isomer, tautomer, isotope marker, or prodrug thereof according to claim 1.

9. A pharmaceutical composition comprising the compound or the pharmaceutically acceptable salt, ester, solvate, optical isomer, tautomer, isotope marker, or prodrug thereof according to claim 7.

10. The compound or the pharmaceutically acceptable salt, ester, solvate, optical isomer, tautomer, isotope marker, or prodrug thereof according to claim 1, wherein

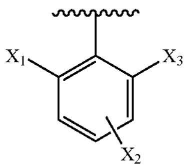

is selected from the group consisting of:

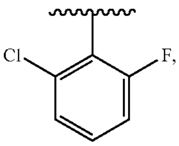

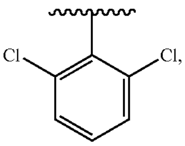

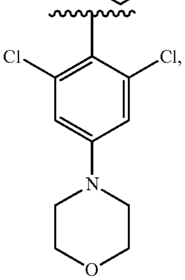

and

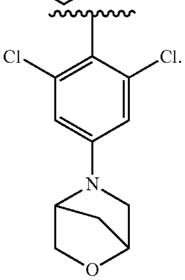

11. The compound or the pharmaceutically acceptable salt, ester, solvate, optical isomer, tautomer, isotope marker, or prodrug thereof according to claim 4, wherein

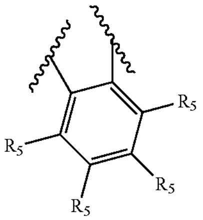

is selected from the group consisting of:

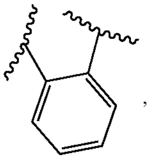

,

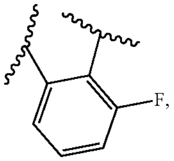

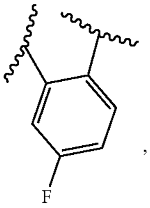

,

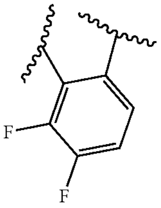

,

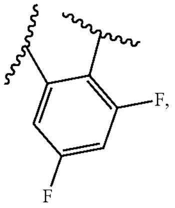

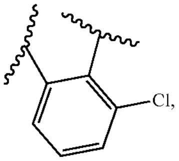

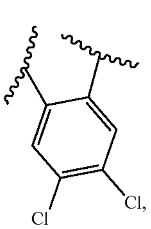

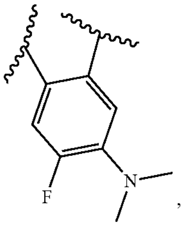

,

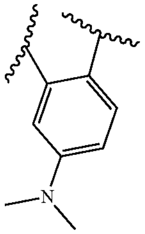

, and

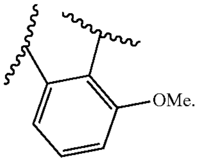

12. The compound or the pharmaceutically acceptable salt, ester, solvate, optical isomer, tautomer, isotope marker, or prodrug thereof according to claim 5, wherein

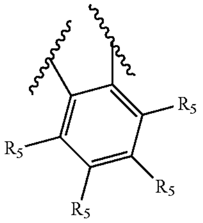

is selected from the group consisting of:
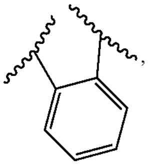,
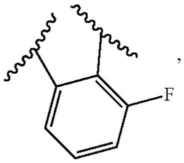,
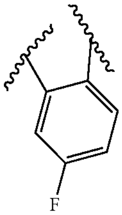,
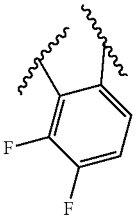,
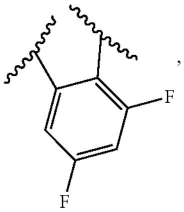,
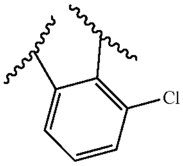,
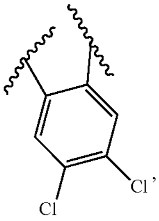
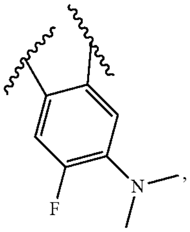
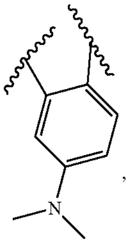, and
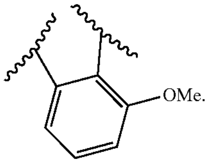
13. The compound or the pharmaceutically acceptable salt, ester, solvate, optical isomer, tautomer, isotope marker, or prodrug thereof according to claim 6, wherein
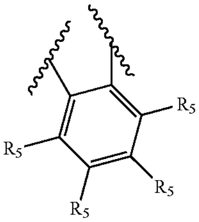
is selected from the group consisting of:
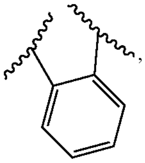,
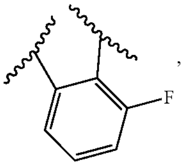,
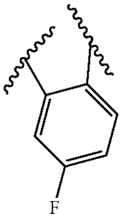,
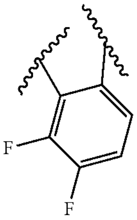,
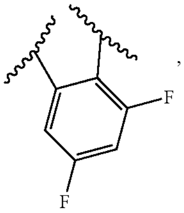,
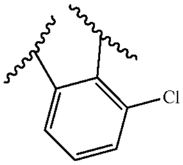,
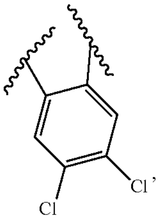
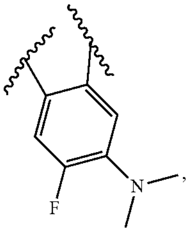
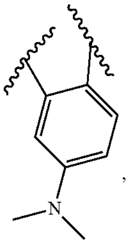, and
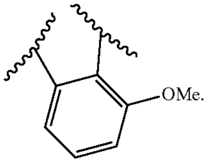
* * * * *